US012799545B2

United States Patent
(12) United States Patent
Yang et al.

(10) Patent No.: US 12,799,545 B2
(45) Date of Patent: Nov. 17, 2026

(54) METHODS AND COMPOSITIONS FOR SUPERSENSITIVE AND SPECIFIC DETECTION OF CITRUS GREENING AND PHYTOPLASMA PATHOGENS

(71) Applicant: THE PENN STATE RESEARCH FOUNDATION, University Park, PA (US)

(72) Inventors: Yinong Yang, State College, PA (US); Matthew S. Wheatley, Ithaca, NY (US); Qin Wang, State College, PA (US)

(73) Assignee: THE PENN STATE RESEARCH FOUNDATION, University Park, PA (US)

( * ) Notice: Subject to any disclaimer, the term of this patent is extended or adjusted under 35 U.S.C. 154(b) by 423 days.

(21) Appl. No.: 18/311,427

(22) Filed: May 3, 2023

(65) Prior Publication Data

US 2023/0357869 A1 Nov. 9, 2023

Related U.S. Application Data

(60) Provisional application No. 63/364,081, filed on May 3, 2022.

(51) Int. Cl.

| | |
|---|---|
| ***C12Q 1/6895*** | (2018.01) |
| ***C12N 9/22*** | (2006.01) |
| ***C12N 15/11*** | (2006.01) |

(52) U.S. Cl.

CPC ............. *C12Q 1/6895* (2013.01); *C12N 9/22* (2013.01); *C12N 15/11* (2013.01); *C12N 2310/20* (2017.05)

(58) Field of Classification Search

None

See application file for complete search history.

(56) References Cited

U.S. PATENT DOCUMENTS 10,253,365 B1 * 4/2019 Doudna ............... C12Q 1/6876

OTHER PUBLICATIONS

Chen et al. ("CRISPR-Cas12a target binding unleashes indiscriminate single-stranded DNase activity" 2018 Science 360:436-439, of record IDS May 10, 2024). (Year: 2018).*

Verosloff et al. ("PLANT-Dx: A Molecular Diagnostic for Point-of-Use Detection of Plant Pathogens" 2019 ACS Synth. Biol. 8: 902-905). (Year: 2019).*

(Continued)

*Primary Examiner* — Matthew R Keogh

*Assistant Examiner* — Rebecca Stephens

(74) *Attorney, Agent, or Firm* — McKee, Voorhees & Sease, PLC

(57) ABSTRACT

The embodiments disclosed herein utilize type V CRISPR/Cas effector proteins to provide robust diagnostic assays with attomolar sensitivity. Embodiments disclosed herein can detect DNA targets from bacterial plant pathogens and can differentiate targets from non-targets based on single base pair differences. Such embodiments are useful in multiple scenarios involving bacterial plant pathogens such as *Candidatus Liberibacter asiaticus* and *Candidatus Phytoplasma trifolii* responsible for citrus greening and potato purple top, respectively.

9 Claims, 13 Drawing Sheets

Specification includes a Sequence Listing.

nrdB Amplicon - 247 bps

CATCATGCGAGATGAATCACTGCATCTCAATTTTGGTATTGATGTCATCAACCAAATTAAAAT
CGAAAACCCCCATCTTTGGACAAAAGAGTTCCAACAAAAAAGTCGCACCATGCTCCATGAA
GCTACCCTCCTCGAAATCGCCTATGCACATGAAACAATGCCAAAAGGGTTCGTGGGGTTAA
ATGCTCCCTCATGTGAACAATATATGCAGTTCATCGCCAATCGTCGTTGTCACCAAATCGGT

(56) References Cited

OTHER PUBLICATIONS

Zheng et al. ("Unusual Five Copies and Dual Forms of nrdB in "Candidatus Liberibacter asiaticus": Biological Implications and PCR Detection Application" 2016 Scientific Reports 6:39020 (9 total pages, DOI: 10.1038/srep39020). (Year: 2016).*

Aman R, Mahas A, Marsic T, Hassan N, Mahfouz MM. Efficient, rapid, and sensitive detection of plant RNA viruses with one-pot RT-RPA-CRISPR/Cas12a assay. Frontiers in microbiology. Dec. 17, 2020;11:610872.

Chen JS, Ma E, Harrington LB, Da Costa M, Tian X, Palefsky JM, Doudna JA. CRISPR-Cas12a target binding unleashes indiscriminate single-stranded DNase activity. Science. Apr. 27, 2018;360(6387):436-9.

Gootenberg JS, Abudayyeh OO, Kellner MJ, Joung J, Collins JJ, Zhang F. Multiplexed and portable nucleic acid detection platform with Cas13, Cas12a, and Csm6. Science. Apr. 27, 2018;360(6387):439-44.

Jiao J, Kong K, Han J, Song S, Bai T, Song C, Wang M, Yan Z, Zhang H, Zhang R, Feng J. Field detection of multiple RNA viruses/viroids in apple using a CRISPR/Cas12a-based visual assay. Plant biotechnology journal. Feb. 2021;19(2):394-405.

Kang H, Peng Y, Hua K, Deng Y, Bellizzi M, Gupta DR, Mahmud NU, Urashima AS, Paul SK, Peterson G, Zhou Y. Rapid detection of wheat blast pathogen Magnaporthe oryzae Triticum pathotype using genome-specific primers and Cas 12a-mediated technology. Engineering. Sep. 1, 2021;7(9):1326-35.

Wheatley MS, Duan YP, Yang Y. Highly sensitive and rapid detection of citrus Huanglongbing pathogen ('Candidatus Liberibacter asiaticus') using Cas12a-based methods. Phytopathology®. Dec. 29, 20219;111(12):2375-82.

Wheatley MS, Yang Y. Versatile applications of the CRISPR/Cas toolkit in plant pathology and disease management. Phytopathology®. Jul. 30, 2021;111(7):1080-90.

Zetsche B, Gootenberg JS, Abudayyeh OO, Slaymaker IM, Makarova KS, Essletzbichler P, Volz SE, Joung J, Van Der Oost J, Regev A, Koonin EV. Cpf1 is a single RNA-guided endonuclease of a class 2 CRISPR-Cas system. cell. Oct. 22, 2015;163(3):759-71.

Zhang YM, Zhang Y, Xie K. Evaluation of CRISPR/Cas12a-based DNA detection for fast pathogen diagnosis and GMO test in rice. Molecular Breeding. Jan. 2020;40(1):11.

* cited by examiner

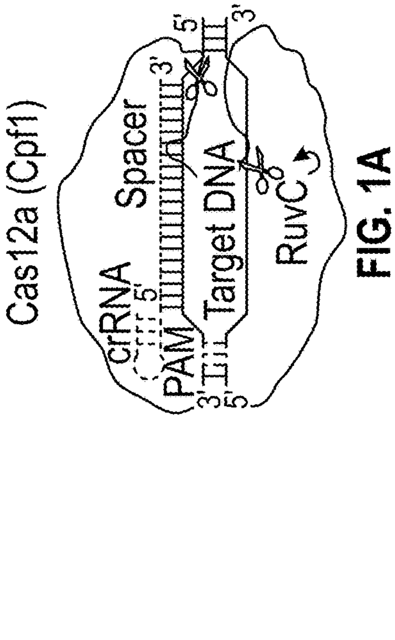
FIG. 1A
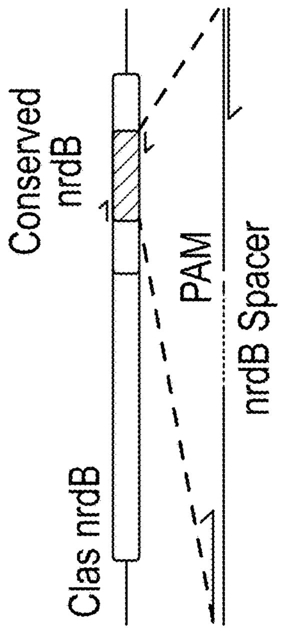
FIG. 1B
nrdB Amplicon - 247 bps
```
CATCATGCGAGATGAATCACTGCATCTCAATTTGGTATTGATGTCATCAACCAAATTAAAAT
CGAAAACCCCCATCTTTGGACAAAAGAGTTCCAACAAAAAAGTCGCACCATGCTCCATGAA
GCTACCCTCCTCGAAAATCGCCTATGCACATGAAACAATGCCAAAAGGTTCGTGGGTTAA
ATGCTCCCTCATGTGAACAATATATGCAGTTCATCGCCAATCGTCGTTGTCACCAAATCGGT
```
FIG. 1C
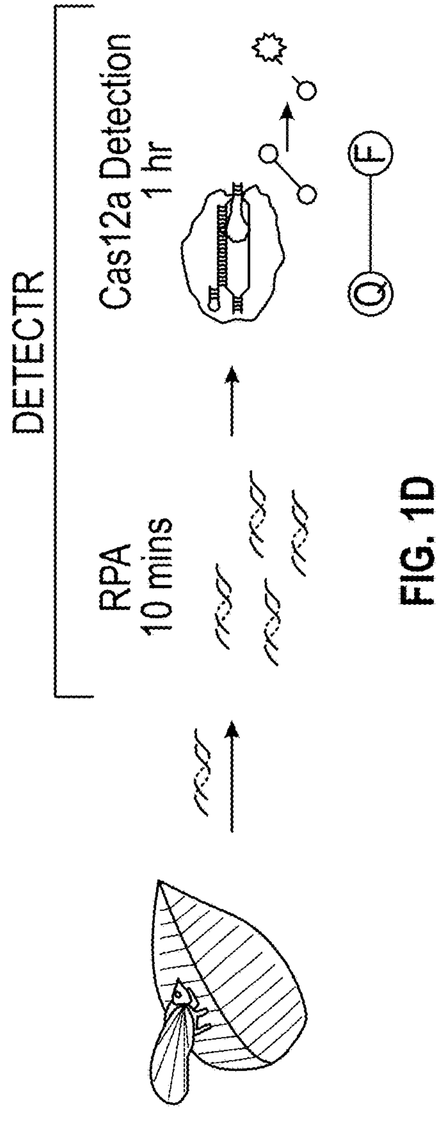
FIG. 1D

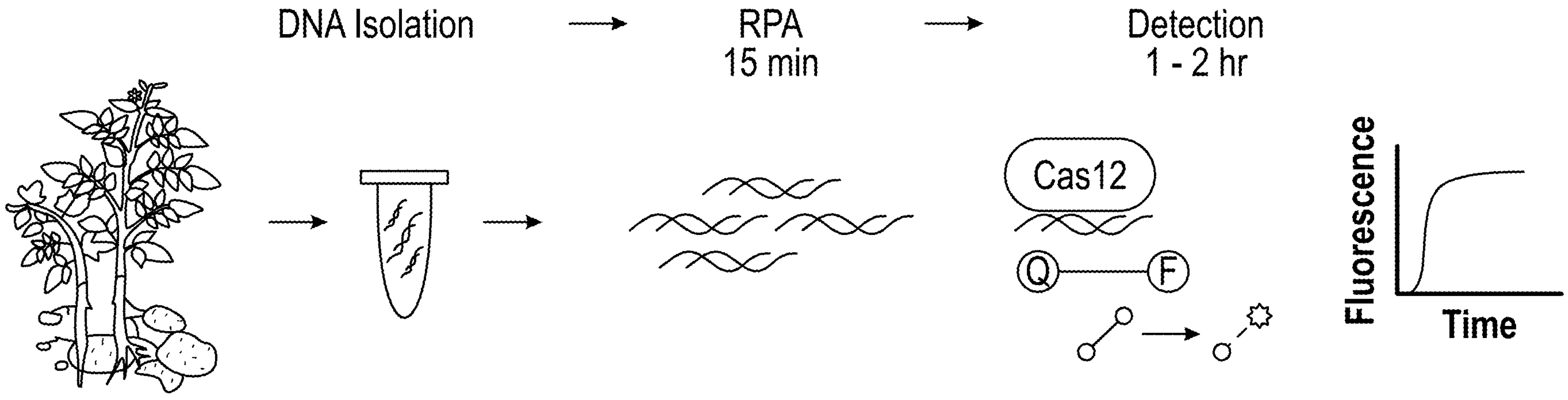
FIG. 7A
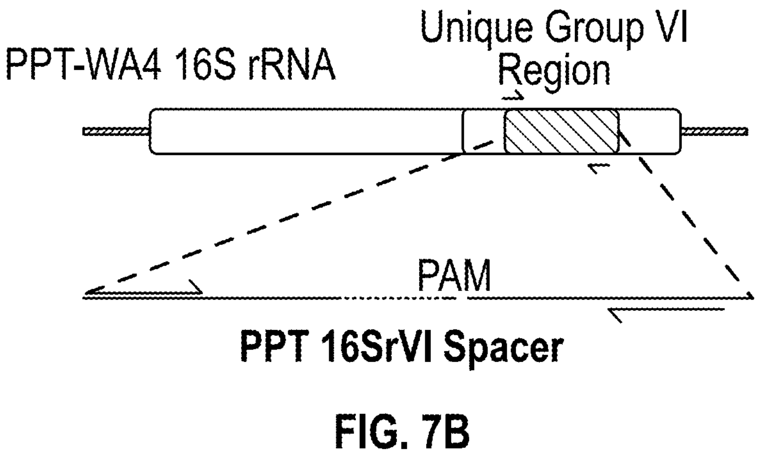
FIG. 7B
PPT 16S-23S ITS Amplicon - 156 bp
TGATAAGCGTGAGGTCGGTGGTTCAAGT
CCATTTAGGCCCACCAAAAAAAGGTCCT
GCTTAAGAAGTTCTTTGAAAAGTAGGTA
AACATGCTTTAAAATTTTCATAAAGTTG
AAGGAAGTAAGGGCATATAGTGGATGCC
TTGGCACTAAGA
FIG. 7C

METHODS AND COMPOSITIONS FOR SUPERSENSITIVE AND SPECIFIC DETECTION OF CITRUS GREENING AND PHYTOPLASMA PATHOGENS

CROSS REFERENCE TO RELATED APPLICATIONS

This application claims priority to provisional application U.S. Ser. No. 63/364,081, filed May 3, 2022, which is incorporated herein by reference in its entirety.

GRANT REFERENCE

This invention was made with government support under Cooperative Agreement No. 58-8042-9-026 awarded by the United States Department of Agriculture/ARS and under Hatch Act Project No. PEN04659 awarded by the United States Department of Agriculture/NIFA. The Government has certain rights in the invention.

SEQUENCE LISTING XML

The instant application contains a sequence listing, which has been submitted in XML file format by electronic submission and is hereby incorporated by reference in its entirety. The XML file, created on Apr. 26, 2023, is named P13904US01.xml and is 21,343 bytes in size.

TECHNICAL FIELD

The present disclosure generally relates to the field of biotechnology and plant disease diagnostics.

BACKGROUND

Citrus greening, also known as Huanglongbing (HLB), is the most devastating disease that threatens worldwide citrus production, which is valued at roughly $17 billion from the sale of fresh fruit and juices. HLB is caused primarily by *Candidatus Liberibacter asiaticus* (CLas), a phloem-limited, fastidious, gram-negative bacterium that is transmitted via insect vectors such as citrus psyllids or through the grafting of infected tissues. Since it reached Florida in 2005, HLB has decimated that state's citrus trees, reducing production by more than 70%. The disease has now spread to California, Georgia, Louisiana, and Texas, and poses a great threat to the $3.35 billion US citrus industry. Phytoplasmas are a group of cell wall-less phytopathogenic bacteria that infect many agriculturally important plant species such as tomato, potato, and grapevine. For example, *Candidatus Phytoplasma trifolii* is responsible for repeated outbreaks of potato purple top (PPT) and potato witches' broom (PWB) that occurred along the Pacific Coast of the United States since 2002, inflicting significant economic losses.

SUMMARY

In order to manage citrus greening and phytoplasma diseases, it is critical to develop highly specific and supersensitive methods for detection and quarantine of infected crops and insect vectors to minimize crop loss and prevent disease transmission. Although various technologies such as electron microscopy, serology, DNA probes, ELISA, and quantitative PCR (qPCR) have been used to diagnose citrus greening and phytoplasma diseases, it is still challenging to rapidly and reliably detect at early infection stage with these techniques due to the low titer of these pathogens within infected plants.

The CRISPR/Cas (Clustered Regularly Interspersed Short Palindromic Repeats/CRISPR associated) system has been adapted as a molecular diagnostic tool besides its conventional applications in genome editing. Due to its ease of use and supersensitivity, Cas12-based detection facilitates the early detection of citrus greening and phytoplamsal pathogens with high-throughput and field-deployable capabilities. The methods enable ultrasensitive detection of nucleic acids from citrus greening or phytoplasmal pathogens at the attomolar level (approximately 100 to 1000 times greater sensitivity than conventional qPCR). Because of their compatibility with fluorescence microplate reader and lateral flow immunostrip, the Cas12-based methods facilitate both high-throughput and field-deployable diagnostics for early detection of citrus greening and phytoplasmal pathogens.

Provided are compositions and methods for detecting a target DNA (double stranded or single stranded) in a sample. In certain embodiments, a subject method includes: (a) contacting the sample with: (i) a type V CRISPR/Cas effector protein (e.g., a Cas12 protein such as Cas12a, Cas12b, Cas12c, Cas12d, Cas12e); (ii) a guide RNA (comprising a region that binds to the type V CRISPR/Cas effector protein, and a spacer sequence that hybridizes with the target DNA); and (iii) a reporter oligonucleotide that is single stranded (i.e., a "single stranded DNA reporter oligonucleotide") and does not hybridize with the spacer sequence of the guide RNA; and (b) detecting a signal produced by cleavage (by the type V CRISPR/Cas effector protein) of the single stranded DNA reporter oligonucleotide. In certain embodiments, the single stranded DNA reporter oligonucleotide includes a fluorescence-emitting dye pair (e.g., a fluorescence-emitting dye pair is a fluorescence resonance energy transfer (FRET) pair, a quencher/fluor pair). In certain embodiments, the target DNA is from a bacterial plant pathogen (e.g., *Candidatus liberibacter* spp., *Candidatus phytoplasma* spp.). In certain embodiments, the contacting is inside of a cell such as a plant cell.

Also provided are compositions (e.g., kits) for practicing the subject methods.

In certain embodiments, the compositions may further comprise nucleic acid amplification components. The nucleic acid amplification components may comprise specific primers. In certain embodiments, sample nucleic acids are amplified to obtain a DNA template containing the target DNA, which could be targeted by guide RNAs. The nucleic acid may be DNA and amplified by any method described herein.

In certain embodiments, the guide RNAs are designed to bind to one or more target DNA molecules that are diagnostic for a plant bacterial disease. In certain embodiments, the disease is an infection caused by *Candidatus liberibacter* spp. (e.g., citrus greening) or *Candidatus phytoplasma* spp. (e.g., potato purple top, potato witches' broom). In certain embodiments, the guide RNAs may be designed to bind to one or more target molecules comprising single nucleotide polymorphisms (SNP) in the genome of a bacterial plant pathogen.

A diagnostic device comprising one or more individual discrete volumes, each individual discrete volume comprising a type V CRISPR/Cas effector protein, one or more guide RNAs designed to bind to corresponding DNA target molecule, and optionally further comprising nucleic acid amplification components is also provided. In certain embodiments, the individual discrete volumes are droplets, or the individual discrete volumes are defined on a solid substrate, or the individual discrete volumes are microwells, or the individual discrete volumes are spots defined on a substrate, such as a paper substrate.

These and other aspects, objects, features, and advantages of the example embodiments will become apparent to those having ordinary skill in the art upon consideration of the following detailed description of illustrated example embodiments.

While multiple embodiments are disclosed, still other embodiments will become apparent to those skilled in the art from the following detailed description, which shows and describes illustrative embodiments. Accordingly, the figures and detailed description are to be regarded as illustrative in nature and not restrictive.

BRIEF DESCRIPTION OF THE FIGURES

The following drawings form part of the specification and are included to further demonstrate certain embodiments. In some instances, embodiments can be best understood by referring to the accompanying figures in combination with the detailed description presented herein. The description and accompanying figures may highlight a certain specific example, or a certain embodiment. However, one skilled in the art will understand that portions of the example or embodiment may be used in combination with other examples or embodiments.

FIG. 1A-D is a diagram of CLas DETECTR assay. FIG. 1A shows CRISPR/Cas12a (Cpf1) with spacer of crRNA bound to target dsDNA proximal to PAM. The RuvC nuclease domain becomes active upon correct base-pairing of spacer and target sequence, leading to the cleavage of both strands of the dsDNA target (scissors) and the generation of a 5' staggered, 5 bp overhang. After activation of Cas12a, the RuvC domain remains active with ssDNase activity (arrow). FIG. 1B is a diagram of CLas nrdB and conserved five-copy number region with RPA primer location, nrdB spacer, and PAM. FIG. 1C shows nrdB amplicon for CLas DETECTR assay with primer location, protospacer, and PAM (SEQ ID NO: 19). FIG. 1D is a schematic of CLas DETECTR assay, which includes DNA amplification by RPA and subsequent Cas12a detection based on trans-cleavage of ssDNA reporters.

FIG. 2A shows RPA testing of primer combinations for nrdB target amplification from CLas positive citrus genomic DNA. Each primer combination was used to amplify the nrdB target from SO1, a CLas positive sweet orange DNA sample. The RPA reaction proceeded for 10 minutes at 37° C. After column purification, the DNA concentration was measured prior to being run on 1.5% TAE agarose gel. Lane 1: RPA F1/RPA R1; Lane 2: RPA F1/RPA R2; Lane 3: RPA F1/RPA R3. Molecular weight size marker was included in the form of a 100 bp DNA ladder. FIG. 2B shows in vitro cleavage of nrdB target fragment (amplified with the RPA F1/RPA R3 primer pair) by Cas12a and nrdB crRNA. UD, undigested; D, digested by Cas12a and nrdB crRNA.

FIG. 4A shows sensitivity of DETECTR vs Cas12a without RPA. Note the CLas DETECTR assay enables robust detection of CLas nucleic acids at attomolar sensitivity. NC: negative control. Error bars represent mean±s.d. when n=3 replicates. FIG. 4B shows sensitivity of real-time qPCR for nrdB DNA detection. ND: not detected. Error bars represent mean±s.d. when n=3 replicates. qPCR experiments were performed three times with similar results.

FIG. 7A-C is an illustration of DETECTR assay for specific detection of PPT 16S-23S rDNA ITS target. FIG. 7A is a schematic of the DETECTR assay process, which includes isothermal amplification with RPA, the activation of Cas12a after initial target DNA cleavage, and subsequent indiscriminate cleavage of fluorescent reporter oligos. FIG. 7B is a diagram of PPT WA4 16S rDNA and 16S-23S ITS with the unique group VI sequence chosen to design the cRNA spacer. The PPT 16S-23S rDNA ITS amplicon is indicated with the RPA primer binding sites shown with arrows. FIG. 7C shows the sequence of PPT 16S-23S rDNA ITS amplicon (SEQ ID NO: 20).

FIG. 8A shows RPA testing of primer combinations for PPT 16S-23S rDNA ITS target amplification. After RPA amplification and column purification, the reaction products were loaded onto 1.5% TAE agarose gel for analysis. Efficient amplification was observed from three RPA primer combinations. RPA F2/R3 combination (lane 3) was selected for subsequent assays. M, 100 bp molecular weight marker. FIG. 8B shows in vitro cleavage of the target plasmid (4.8 kb size) by Cas12a and crRNA. M, 1 kb molecular weight marker; UD, undigested, open circle plasmid which exhibited slower mobility in agarose gel; Cas12a, digested with crRNA/Cas12a which produced a 4.8 kb linear fragment due to the single cut); Cas12a and BsaI, digested with crRNA/Cas12a and BsaI, which produced two fragments with expected sizes (1.4 kb and 3.4 kb, respectively) due to two cuts.

FIG. 11A shows the PPT 16S-23S rDNA ITS DETECTR assay carried out using DNA samples from plants infected with group 16SrVI (including A, D and F subgroups), 16SrI, or 16SrIII phytoplasmas. Error bars indicate the mean of the highest fluorescent value over 2 hr±SD when n=3 replicates. A two tailed t-test was done to provide p-values of infected samples compared to negative control, where * p≤0.05 and  p≤0.005. FIG. 11B shows time course depicting the assay specificity for group 16SrVI vs. group 16SrI and 16SrIII strains. FIG. 11**C shows time course depicting the assay specificity for 16SrVI subgroup A (WA4 and WA8) vs. subgroup D (BLL) and F (CPS). WA8, BLL and CPS all contain a single mismatch (MM) in the crRNA spacer, resulting in delayed accumulation of the fluorescent reporter signal over time. NC, negative control (disease-free potato DNA).

DETAILED DESCRIPTION

Figure 2A:
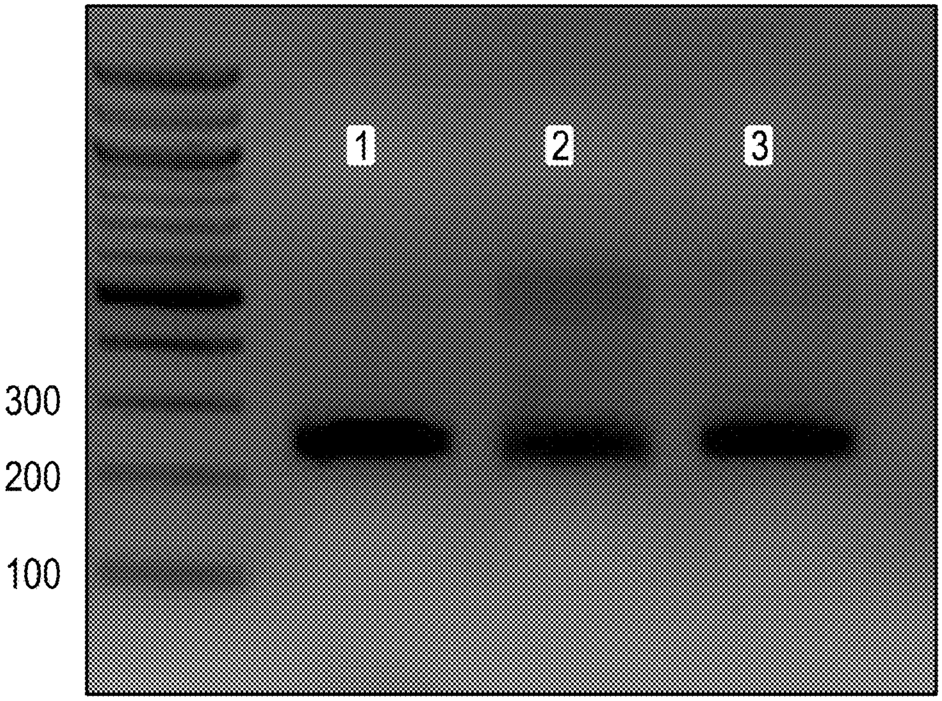
FIG. 2A-B shows evaluation of RPA primers and in vitro DNA cleavage efficiency.

So that the present disclosure may be more readily understood, certain terms are first defined. Unless defined otherwise, all technical and scientific terms used herein have the same meaning as commonly understood by one of ordinary skill in the art to which embodiments of the disclosure pertain. Many methods and materials similar, modified, or equivalent to those described herein can be used in the practice of the embodiments of the present disclosure without undue experimentation, the preferred materials and methods are described herein. In describing and claiming the embodiments of the present disclosure, the following terminology will be used in accordance with the definitions set out below.

It is to be understood that all terminology used herein is for the purpose of describing particular embodiments only, and is not intended to be limiting in any manner or scope. For example, as used in this specification and the appended claims, the singular forms "a," "an" and "the" can include plural referents unless the content clearly indicates otherwise. Similarly, the word "or" is intended to include "and" unless the context clearly indicate otherwise. The word "or" means any one member of a particular list and includes any combination of members of that list. Further, all units, prefixes, and symbols may be denoted in its SI accepted form.

Unless otherwise stated, nucleic acid sequences in the text of this disclosure are given, when read from left to right, in the 5' to 3' direction. One of skill in the art would be aware that a given DNA sequence is understood to define a corresponding RNA sequence which is identical to the DNA sequence except for replacement of the thymine (T) nucleotides of the DNA with uracil (U) nucleotides. Thus, providing a specific DNA sequence is understood to define the exact RNA equivalent. A given first polynucleotide sequence, whether DNA or RNA, further defines the sequence of its exact complement (which can be DNA or RNA), a second polynucleotide that hybridizes perfectly to the first polynucleotide by forming Watson-Crick base-pairs. For DNA:DNA duplexes (hybridized strands), base-pairs are adenine:thymine or guanine:cytosine; for DNA:RNA duplexes, base-pairs are adenine:uracil or guanine:cytosine.

Provided are polynucleotides that have at least about or at least 40%, 45%, 50%, 51%, 52%, 53%, 54%, 55%, 56%, 57%, 58%, 59%, 60%, 61%, 62%, 63%, 64%, 65%, 66%, 67%, 68%, 69%, 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99% or greater sequence identity compared to a reference nucleotide sequence, such as a nucleotide sequence disclosed in the sequence listing herein, using one of the alignment programs described herein using standard parameters, as well as nucleotide substitutions, deletions, insertions, fragments thereof, and combinations thereof.

The terms "polynucleotide", "polynucleotide sequence", "nucleic acid sequence", "nucleic acid fragment", and "isolated nucleic acid fragment" are used interchangeably herein. These terms encompass nucleotide sequences and the like. A polynucleotide may be a polymer of RNA or DNA that is single- or double-stranded, that optionally contains synthetic, non-natural or altered nucleotide bases. A polynucleotide in the form of a polymer of DNA may be comprised of one or more segments of cDNA, genomic DNA, synthetic DNA, or mixtures thereof. Nucleotides (usually found in their 5'-monophosphate form) are referred to by a single letter designation as follows: "A" for adenylate or deoxyadenylate (for RNA or DNA, respectively), "C" for cytidylate or deoxycytidylate, "G" for guanylate or deoxyguanylate, "U" for uridylate, "T" for deoxythymidylate, "R" for purines (A or G), "Y" for pyrimidines (C or T), "K" for G or T, "H" for A or C or T, "I" for inosine, and "N" for any nucleotide.

An "isolated polynucleotide" generally refers to a polymer of ribonucleotides (RNA) or deoxyribonucleotides (DNA) that is single- or double-stranded, optionally containing synthetic, non-natural or altered nucleotide bases, that is no longer in its natural environment and have been placed in a difference environment by the hand of man, for example in vitro. An isolated polynucleotide in the form of DNA may be comprised of one or more segments of cDNA, genomic DNA or synthetic DNA.

The term "oligonucleotide" refers to a polynucleotide of between 4 and 100 nucleotides of single- or double-stranded nucleic acid (e.g., DNA, RNA, or a modified nucleic acid). Oligonucleotides are also known as "oligomers" or "oligos" and can be isolated from genes, transcribed (in vitro and/or in vivo), or chemically synthesized.

A "recombinant" nucleic acid molecule (or DNA) is used herein to refer to a nucleic acid sequence (or DNA) that is in a recombinant plant host cell. In some embodiments, an "isolated" or "recombinant" nucleic acid is free of sequences (preferably protein encoding sequences) that naturally flank the nucleic acid (i.e., sequences located at the 5' and 3' ends of the nucleic acid) in the genomic DNA of the organism from which the nucleic acid is derived.

A transcription regulatory element or sequence, or a regulatory element or sequence generally refers to a transcriptional regulatory element involved in regulating the transcription of a nucleic acid molecule such as a gene or a target gene. The regulatory element is a nucleic acid and may include a promoter, an enhancer, an intron, a 5'-untranslated region (5'-UTR, also known as a leader sequence), or a 3'-UTR or a combination thereof. A regulatory element may act in "cis" or "trans", and generally it acts in "cis", i.e. it activates expression of genes located on the same nucleic acid molecule, e.g. a chromosome, where the regulatory element is located. The nucleic acid molecule regulated by a regulatory element does not necessarily have to encode a functional peptide or polypeptide, e.g., the regulatory element can modulate the expression of a short interfering RNA or an anti-sense RNA.

"Promoter" generally refers to a nucleic acid fragment capable of controlling transcription of another nucleic acid fragment. A promoter generally includes a core promoter (also known as minimal promoter) sequence that includes a minimal regulatory region to initiate transcription, that is a transcription start site. Generally, a core promoter includes a TATA box and a GC rich region associated with a CAAT box or a CCAAT box. These elements act to bind RNA polymerase II to the promoter and assist the polymerase in locating the RNA initiation site. Some promoters may not have a TATA box or CAAT box or a CCAAT box, but instead may contain an initiator element for the transcription initiation site. A core promoter is a minimal sequence required to direct transcription initiation and generally may not include enhancers or other UTRs. Promoters may be derived in their entirety from a native gene, or be composed of different elements derived from different promoters found in nature, or even comprise synthetic DNA segments. It is understood by those skilled in the art that different promoters may direct the expression of a gene in different tissues or cell types, or at different stages of development, or in response to different environmental conditions. Core promoters are often modified to produce artificial, chimeric, or hybrid promoters, and can further be used in combination with other regulatory elements, such as cis-elements, 5'UTRs, enhancers, or introns, that are either heterologous to an active core promoter or combined with its own partial or complete regulatory elements.

The term "cis-element" generally refers to transcriptional regulatory element that affects or modulates expression of an operably linked transcribable polynucleotide, where the transcribable polynucleotide is present in the same DNA sequence. A cis-element may function to bind transcription factors, which are trans-acting polypeptides that regulate transcription.

The termination region may be native with the transcriptional initiation region, may be native with the operably linked DNA sequence of interest, may be native with the plant host or may be derived from another source (i.e., foreign or heterologous to the promoter, the sequence of interest, the plant or any combination thereof).

In certain embodiments, the sequences include one or more contiguous nucleotides. "Contiguous nucleotides" is used herein to refer to nucleotide residues that are immediately adjacent to one another.

Provided are nucleotide constructs comprising sequences described herein. The use of the term "nucleotide constructs" herein is not intended to limit the embodiments to nucleotide constructs comprising DNA. Nucleotide constructs particularly polynucleotides and oligonucleotides composed of ribonucleotides and combinations of ribonucleotides and deoxyribonucleotides may also be employed in the methods disclosed herein. The nucleotide constructs, nucleic acids, and nucleotide sequences of the embodiments additionally encompass all complementary forms of such constructs, molecules, and sequences. Further, the nucleotide constructs, nucleotide molecules, and nucleotide sequences of the embodiments encompass all nucleotide constructs, molecules, and sequences which can be employed in the methods of the embodiments for transforming plants including, but not limited to, those comprised of deoxyribonucleotides, ribonucleotides, and combinations thereof. Such deoxyribonucleotides and ribonucleotides include both naturally occurring molecules and synthetic analogues. The nucleotide constructs, nucleic acids, and nucleotide sequences of the embodiments also encompass all forms of nucleotide constructs including, but not limited to, single-stranded forms, double-stranded forms, hairpins, stem-and-loop structures and the like.

To determine the percent identity of two amino acid sequences or of two nucleic acids, the sequences are aligned for optimal comparison purposes. The percent identity between the two sequences is a function of the number of identical positions shared by the sequences (i.e., percent identity=number of identical positions/total number of positions (e.g., overlapping positions).times.100). In one embodiment, the two sequences are the same length. In another embodiment, the percent identity is calculated across the entirety of the reference sequence. The percent identity between two sequences can be determined using techniques like those described below, with or without allowing gaps. In calculating percent identity, typically exact matches are counted. A gap, (a position in an alignment where a residue is present in one sequence but not in the other) is regarded as a position with non-identical residues.

The determination of percent identity between two sequences can be accomplished using a mathematical algorithm. A non-limiting example of a mathematical algorithm utilized for the comparison of two sequences is the algorithm incorporated into the BLASTN and BLASTX programs. Karlin and Altschul (1990) Proc. Nat'l. Acad. Sci. USA 87:2264, Altschul et al. (1990) J. Mol. Biol. 215:403, and Karlin and Altschul (1993) Proc. Nat'l. Acad. Sci. USA 90:5873-5877. BLAST nucleotide searches can be performed with the BLASTN program, score=100, word length=12, to obtain nucleotide sequences homologous to nucleic acid molecules disclosed herein. BLAST protein searches can be performed with the BLASTX program, score=50, word length=3, to obtain amino acid sequences homologous to polypeptides disclosed herein. To obtain gapped alignments for comparison purposes, Gapped BLAST (in BLAST 2.0) can be utilized as described in Altschul et al. (1997) Nucleic Acids Res. 25:3389. Alternatively, PSI-Blast can be used to perform an iterated search that detects distant relationships between molecules. See Altschul et al. (1997) supra. When utilizing BLAST, Gapped BLAST, and PSI-Blast programs, the default parameters of the respective programs (e.g., BLASTX and BLASTN) can be used. Alignment may also be performed manually by inspection.

Another non-limiting example of a mathematical algorithm utilized for the comparison of sequences is the ClustalW algorithm (Higgins et al. (1994) Nucleic Acids Res. 22:4673-4680). ClustalW compares sequences and aligns the entirety of the amino acid or DNA sequence, and thus can provide data about the sequence conservation of the entire amino acid sequence. The ClustalW algorithm is used in several commercially available DNA/amino acid analysis software packages, such as the ALIGNX module of the Vector NTI Program Suite (Invitrogen Corporation, Carlsbad, Calif). After alignment of amino acid sequences with ClustalW, the percent amino acid identity can be assessed. A non-limiting example of a software program useful for analysis of ClustalW alignments is GENEDOC™. GENEDOC™ (Karl Nicholas) allows assessment of amino acid (or DNA) similarity and identity between multiple proteins. Another non-limiting example of a mathematical algorithm utilized for the comparison of sequences is the algorithm of Myers and Miller (1988) CABIOS 4(1):11-17. Such an algorithm is incorporated into the ALIGN program (version 2.0), which is part of the GCG Wisconsin Genetics Software Package, Version 10 (available from Accelrys, Inc., San Diego, Calif, USA). When utilizing the ALIGN program for comparing amino acid sequences, a PAM120 weight residue table, a gap length penalty of 12, and a gap penalty of 4 can be used. Unless otherwise stated, GAP Version 10, which uses the algorithm of Needleman and Wunsch (1970) J. Mol. Biol. 48(3):443-453, will be used to determine sequence identity or similarity using the following parameters: % identity and % similarity for a nucleotide sequence using GAP Weight of 50 and Length Weight of 3, and the nwsgapdna.cmp scoring matrix; % identity or % similarity for an amino acid sequence using GAP weight of 8 and length weight of 2, and the BLOSUM62 scoring program. Equivalent programs may also be used. By "equivalent program" is intended any sequence comparison program that, for any two sequences in question, generates an alignment having identical nucleotide residue matches and an identical percent sequence identity when compared to the corresponding alignment generated by GAP Version 10.

As is well known to those skilled in molecular biology, similarity of two nucleic acids can be characterized by their tendency to hybridize. Provided are nucleic acids that hybridize to those sequences disclosed herein under stringent conditions. As used herein the terms "stringent conditions" or "stringent hybridization conditions" are intended to refer to conditions under which a probe or nucleic acid will hybridize (anneal) to a particular sequence to a detectably greater degree than to other sequences (e.g. at least 2-fold over background).

By "hybridizable" or "complementary" or "substantially complementary" it is meant that a nucleic acid (e.g. RNA, DNA) comprises a sequence of nucleotides that enables it to non-covalently bind, i.e. form Watson-Crick base pairs and/or G/U base pairs, "anneal", or "hybridize," to another nucleic acid in a sequence-specific, antiparallel, manner (i.e., a nucleic acid specifically binds to a complementary nucleic acid) under the appropriate in vitro and/or in vivo conditions of temperature and solution ionic strength. Standard Watson-Crick base-pairing includes: adenine/adenosine) (A) pairing with thymidine/thymidine (T), A pairing with uracil/uridine (U), and guanine/guanosine) (G) pairing with cytosine/cytidine (C). In addition, for hybridization between two RNA molecules (e.g., dsRNA), and for hybridization of a DNA molecule with an RNA molecule (e.g., when a DNA target nucleic acid base pairs with a guide RNA, etc.): G can also base pair with U. For example, G/U base-pairing is partially responsible for the degeneracy (i.e., redundancy) of the genetic code in the context of tRNA anti-codon base-pairing with codons in mRNA. Thus, in the context of this disclosure, a G (e.g., of a protein-binding segment (e.g., dsRNA duplex) of a guide RNA molecule; of a target nucleic acid (e.g., target DNA) base pairing with a guide RNA) is considered complementary to both a U and to C. For example, when a G/U base-pair can be made at a given nucleotide position of a protein-binding segment (e.g., dsRNA duplex) of a guide RNA molecule, the position is not considered to be non-complementary, but is instead considered to be complementary.

Hybridization requires that the two nucleic acids contain complementary sequences, although mismatches between bases are possible. The conditions appropriate for hybridization between two nucleic acids depend on the length of the nucleic acids and the degree of complementarity, variables well known in the art. The greater the degree of complementarity between two nucleotide sequences, the greater the value of the melting temperature (Tm) for hybrids of nucleic acids having those sequences. Typically, the length for a hybridizable nucleic acid is 8 nucleotides or more (e.g., 10 nucleotides or more, 12 nucleotides or more, 15 nucleotides or more, 20 nucleotides or more, 22 nucleotides or more, 25 nucleotides or more, or 30 nucleotides or more).

It is understood that the sequence of a polynucleotide need not be 100% complementary to that of its target nucleic acid to be specifically hybridizable. Moreover, a polynucleotide may hybridize over one or more segments such that intervening or adjacent segments are not involved in the hybridization event (e.g., a loop structure or hairpin structure, a 'bulge', and the like). A polynucleotide can comprise 60% or more, 65% or more, 70% or more, 75% or more, 80% or more, 85% or more, 90% or more, 95% or more, 98% or more, 99% or more, 99.5% or more, or 100% sequence complementarity to a target region within the target nucleic acid sequence to which it will hybridize. For example, an antisense nucleic acid in which 18 of 20 nucleotides of the antisense compound are complementary to a target region, and would therefore specifically hybridize, would represent 90 percent complementarity. The remaining noncomplementary nucleotides may be clustered or interspersed with complementary nucleotides and need not be contiguous to each other or to complementary nucleotides. Percent complementarity between particular stretches of nucleic acid sequences within nucleic acids can be determined using any convenient method.

The terms "peptide," "polypeptide," and "protein" are used interchangeably herein, and refer to a polymeric form of amino acids of any length, which can include coded and non-coded amino acids, chemically or biochemically modified or derivatized amino acids, and polypeptides having modified peptide backbones.

"Binding" as used herein (e.g., with reference to an DNA-binding domain of a polypeptide, binding to a target nucleic acid, and the like) refers to a non-covalent interaction between macromolecules (e.g., between a protein and a nucleic acid; between a guide RNA and a target nucleic acid; and the like). While in a state of non-covalent interaction, the macromolecules are said to be "associated" or "interacting" or "binding" (e.g., when a molecule X is said to interact with a molecule Y, it is meant the molecule X binds to molecule Y in a non-covalent manner). Not all components of a binding interaction need be sequence-specific (e.g., contacts with phosphate residues in a DNA backbone), but some portions of a binding interaction may be sequence-specific. Binding interactions are generally characterized by a dissociation constant ($K_d$) of less than $10^{-6}$ M, less than $10^{-7}$ M, less than $10^{-8}$M, less than $10^{-9}$ M, less than $10^{-10}$ M, less than $10^{-11}$ M, less than $10^{-12}$ M, less than $10^{-13}$ M, less than $10^{-14}$ M, or less than $10^{-15}$ M. "Affinity" refers to the strength of binding, increased binding affinity being correlated with a lower $K_d$.

By "binding domain" it is meant a protein domain that is able to bind non-covalently to another molecule. A binding domain can bind to, for example, an DNA molecule (a DNA-binding domain) and/or a protein molecule (a protein-binding domain). In the case of a protein having a protein-binding domain, it can, in certain embodiments, bind to itself (to form homodimers, homotrimers, etc.) and/or it can bind to one or more regions of a different protein or proteins.

Any given component, or combination of components can be unlabeled, or can be detectably labeled with a label moiety. In certain embodiments, when two or more components are labeled, they can be labeled with label moieties that are distinguishable from one another.

"Plant" as used herein refers to whole plants, plant organs (e.g., leaves, stems, roots, etc.), seeds, plant cells, propagules, embryos and progeny of the same. Plant cells can be differentiated or undifferentiated (e.g. callus, suspension culture cells, protoplasts, leaf cells, root cells, phloem cells and pollen).

Type V CRISPR/Cas proteins, e.g., Cas12 proteins such as Cpf1 (Cas12a) and C2c1 (Cas12b) can promiscuously cleave non-targeted single stranded DNA (ssDNA) once activated by detection of a target DNA (double or single stranded). Once a type V CRISPR/Cas effector protein (e.g., a Cas12 protein such as Cas12a, Cas12b, Cas12c, Cas12d, Cas12e) is activated by a guide RNA, which occurs when the guide RNA hybridizes to a target sequence of a target DNA (i.e., the sample includes the targeted DNA), the protein becomes a nuclease that promiscuously cleaves ssDNAs (i.e., the nuclease cleaves non-target ssDNAs, i.e., ssDNAs to which the spacer sequence of the guide RNA does not hybridize). Thus, when the target DNA is present in the sample (e.g., above a threshold amount), the result is cleavage of ssDNAs in the sample, which can be detected using any convenient detection method (e.g., using a labeled single stranded DNA reporter oligonucleotide).

Provided are compositions and methods for detecting a target DNA (double stranded or single stranded) in a sample. In certain embodiments, a reporter oligonucleotide is used that is single stranded (ssDNA) and does not hybridize with the spacer sequence of the guide RNA (i.e., the ssDNA reporter oligonucleotide is a non-target ssDNA). Such methods can include (a) contacting the sample with: (i) a type V CRISPR/Cas effector protein (e.g., a Cas12 protein); (ii) a guide RNA comprising: a region that binds to the type V CRISPR/Cas effector protein, and a spacer sequence that hybridizes with the target DNA; and (iii) a reporter oligonucleotide that is single stranded and does not hybridize with the spacer sequence of the guide RNA; and (b) detecting a signal produced by cleavage of the single stranded DNA reporter oligonucleotide by the type V CRISPR/Cas effector protein, thereby detecting the target DNA. As noted above, once a subject Type V CRISPR/Cas effector protein (e.g., a Cas12 protein such as Cas12a, Cas12b, Cas12c, Cas12d, Cas12e) is activated by a guide RNA, which occurs when the sample includes a target DNA to which the guide RNA hybridizes (i.e., the sample includes the targeted target DNA), the Type V CRISPR/Cas effector protein (e.g., a Cas12 protein such as Cas12a, Cas12b, Cas12c, Cas12d, Cas12e) is activated and functions as an endoribonuclease that non-specifically cleaves ssDNAs (including non-target ssDNAs) present in the sample. Thus, when the targeted target DNA is present in the sample (e.g., above a threshold amount), the result is cleavage of ssDNA (including non-target ssDNA) in the sample, which can be detected using any convenient detection method (e.g., using a labeled ssDNA reporter oligonucleotide).

The contacting step of a subject method can be carried out in a composition comprising divalent metal ions. The contacting step can be carried out in an acellular environment, e.g., outside of a cell. The contacting step can be carried out inside a cell. The contacting step can be carried out in a cell in vitro. The contacting step can be carried out in a cell ex vivo. The contacting step can be carried out in a cell in vivo.

The guide RNA can be provided as RNA or as a nucleic acid encoding the guide RNA (e.g., a DNA such as a recombinant expression vector). The Type V CRISPR/Cas effector protein (e.g., a Cas12 protein such as Cas12a, Cas12b, Cas12c, Cas12d, Cas12e) can be provided as a protein or as a nucleic acid encoding the protein (e.g., an mRNA, a DNA such as a recombinant expression vector). In certain embodiments, two or more (e.g., 3 or more, 4 or more, 5 or more, or 6 or more) guide RNAs can be provided by (e.g., using a precursor guide RNA array, which can be cleaved by the Type V CRISPR/Cas effector protein into individual ("mature") guide RNAs).

In certain embodiments (e.g., when contacting with a guide RNA and a Type V CRISPR/Cas effector protein (e.g., a Cas12 protein such as Cas12a, Cas12b, Cas12c, Cas12d, Cas12e)), the sample is contacted for 2 hours or less (e.g., 1.5 hours or less, 1 hour or less, 40 minutes or less, 30 minutes or less, 20 minutes or less, 10 minutes or less, or 5 minutes or less, or 1 minute or less) prior to the measuring step. For example, in certain embodiments, the sample is contacted for 40 minutes or less prior to the measuring step. In certain embodiments, the sample is contacted for 20 minutes or less prior to the measuring step. In certain embodiments, the sample is contacted for 10 minutes or less prior to the measuring step. In certain embodiments, the sample is contacted for 5 minutes or less prior to the measuring step. In certain embodiments, the sample is contacted for 1 minute or less prior to the measuring step. In certain embodiments, the sample is contacted for from 50 seconds to 60 seconds prior to the measuring step. In certain embodiments, the sample is contacted for from 40 seconds to 50 seconds prior to the measuring step. In certain embodiments, the sample is contacted for from 30 seconds to 40 seconds prior to the measuring step. In certain embodiments, the sample is contacted for from 20 seconds to 30 seconds prior to the measuring step. In certain embodiments, the sample is contacted for from 10 seconds to 20 seconds prior to the measuring step.

A method of the present disclosure for detecting a target DNA (single-stranded or double-stranded) in a sample can detect a target DNA with a high degree of sensitivity. In certain embodiments, a method of the present disclosure can be used to detect a target DNA present in a sample comprising a plurality of DNAs (including the target DNA and a plurality of non-target DNAs), where the target DNA is present at one or more copies per $10^7$ non-target DNAs (e.g., one or more copies per $10^6$ non-target DNAs, one or more copies per $10^5$ non-target DNAs, one or more copies per 104 non-target DNAs, one or more copies per $10^3$ non-target DNAs, one or more copies per $10^2$ non-target DNAs, one or more copies per 50 non-target DNAs, one or more copies per 20 non-target DNAs, one or more copies per 10 non-target DNAs, or one or more copies per 5 non-target DNAs). In certain embodiments, a method of the present disclosure can be used to detect a target DNA present in a sample comprising a plurality of DNAs (including the target DNA and a plurality of non-target DNAs), where the target DNA is present at one or more copies per $10^{18}$ non-target DNAs (e.g., one or more copies per $10^{15}$ non-target DNAs, one or more copies per $10^{12}$ non-target DNAs, one or more copies per $10^{9}$ non-target DNAs, one or more copies per $10^{6}$ non-target DNAs, one or more copies per $10^{5}$ non-target DNAs, one or more copies per $10^{4}$ non-target DNAs, one or more copies per $10^{3}$ non-target DNAs, one or more copies per $10^{2}$ non-target DNAs, one or more copies per 50 non-target DNAs, one or more copies per 20 non-target DNAs, one or more copies per 10 non-target DNAs, or one or more copies per 5 non-target DNAs).

In certain embodiments, a method of the present disclosure can detect a target DNA present in a sample, where the target DNA is present at from one copy per $10^{7}$ non-target DNAs to one copy per 10 non-target DNAs (e.g., from 1 copy per $10^{7}$ non-target DNAs to 1 copy per $10^{2}$ non-target DNAs, from 1 copy per $10^{7}$ non-target DNAs to 1 copy per $10^{3}$ non-target DNAs, from 1 copy per $10^{7}$ non-target DNAs to 1 copy per $10^{4}$ non-target DNAs, from 1 copy per $10^{7}$ non-target DNAs to 1 copy per $10^{5}$ non-target DNAs, from 1 copy per $10^{7}$ non-target DNAs to 1 copy per $10^{6}$ non-target DNAs, from 1 copy per $10^{6}$ non-target DNAs to 1 copy per 10 non-target DNAs, from 1 copy per $10^{6}$ non-target DNAs to 1 copy per $10^{2}$ non-target DNAs, from 1 copy per $10^{6}$ non-target DNAs to 1 copy per $10^{3}$ non-target DNAs, from 1 copy per $10^{6}$ non-target DNAs to 1 copy per $10^{4}$ non-target DNAs, from 1 copy per $10^{6}$ non-target DNAs to 1 copy per $10^{5}$ non-target DNAs, from 1 copy per $10^{5}$ non-target DNAs to 1 copy per 10 non-target DNAs, from 1 copy per $10^{5}$ non-target DNAs to 1 copy per $10^{2}$ non-target DNAs, from 1 copy per $10^{5}$ non-target DNAs to 1 copy per $10^{3}$ non-target DNAs, or from 1 copy per $10^{5}$ non-target DNAs to 1 copy per $10^{4}$ non-target DNAs).

In certain embodiments, a method of the present disclosure can detect a target DNA present in a sample, where the target DNA is present at from one copy per $10^{18}$ non-target DNAs to one copy per 10 non-target DNAs (e.g., from 1 copy per $10^{18}$ non-target DNAs to 1 copy per $10^{2}$ non-target DNAs, from 1 copy per $10^{15}$ non-target DNAs to 1 copy per $10^{2}$ non-target DNAs, from 1 copy per $10^{12}$ non-target DNAs to 1 copy per $10^{2}$ non-target DNAs, from 1 copy per $10^{9}$ non-target DNAs to 1 copy per $10^{2}$ non-target DNAs, from 1 copy per $10^{7}$ non-target DNAs to 1 copy per $10^{2}$ non-target DNAs, from 1 copy per $10^{7}$ non-target DNAs to 1 copy per $10^{3}$ non-target DNAs, from 1 copy per $10^{7}$ non-target DNAs to 1 copy per $10^{4}$ non-target DNAs, from 1 copy per $10^{7}$ non-target DNAs to 1 copy per $10^{5}$ non-target DNAs, from 1 copy per $10^{7}$ non-target DNAs to 1 copy per $10^{6}$ non-target DNAs, from 1 copy per $10^{6}$ non-target DNAs to 1 copy per 10 non-target DNAs, from 1 copy per $10^{6}$ non-target DNAs to 1 copy per $10^{2}$ non-target DNAs, from 1 copy per $10^{6}$ non-target DNAs to 1 copy per $10^{3}$ non-target DNAs, from 1 copy per $10^{6}$ non-target DNAs to 1 copy per $10^{4}$ non-target DNAs, from 1 copy per $10^{6}$ non-target DNAs to 1 copy per $10^{5}$ non-target DNAs, from 1 copy per $10^{5}$ non-target DNAs to 1 copy per 10 non-target DNAs, from 1 copy per $10^{5}$ non-target DNAs to 1 copy per $10^{2}$ non-target DNAs, from 1 copy per $10^{5}$ non-target DNAs to 1 copy per $10^{3}$ non-target DNAs, or from 1 copy per $10^{5}$ non-target DNAs to 1 copy per $10^{4}$ non-target DNAs).

In certain embodiments, a method of the present disclosure can detect a target DNA present in a sample, where the target DNA is present at from one copy per $10^{7}$ non-target DNAs to one copy per 100 non-target DNAs (e.g., from 1 copy per $10^{7}$ non-target DNAs to 1 copy per $10^{2}$ non-target DNAs, from 1 copy per $10^{7}$ non-target DNAs to 1 copy per $10^{3}$ non-target DNAs, from 1 copy per $10^{7}$ non-target DNAs to 1 copy per $10^{4}$ non-target DNAs, from 1 copy per $10^{7}$ non-target DNAs to 1 copy per $10^{5}$ non-target DNAs, from 1 copy per $10^{7}$ non-target DNAs to 1 copy per $10^{6}$ non-target DNAs, from 1 copy per $10^{6}$ non-target DNAs to 1 copy per 100 non-target DNAs, from 1 copy per $10^{6}$ non-target DNAs to 1 copy per $10^{2}$ non-target DNAs, from 1 copy per $10^{6}$ non-target DNAs to 1 copy per $10^{3}$ non-target DNAs, from 1 copy per $10^{6}$ non-target DNAs to 1 copy per $10^{4}$ non-target DNAs, from 1 copy per $10^{6}$ non-target DNAs to 1 copy per $10^{5}$ non-target DNAs, from 1 copy per $10^{5}$ non-target DNAs to 1 copy per 100 non-target DNAs, from 1 copy per $10^{5}$ non-target DNAs to 1 copy per $10^{2}$ non-target DNAs, from 1 copy per $10^{5}$ non-target DNAs to 1 copy per $10^{3}$ non-target DNAs, or from 1 copy per $10^{5}$ non-target DNAs to 1 copy per $10^{4}$ non-target DNAs).

In certain embodiments, the threshold of detection, for a subject method of detecting a target DNA in a sample, is 10 nM or less. The term "threshold of detection" is used herein to describe the minimal amount of target DNA that must be present in a sample in order for detection to occur. Thus, as an illustrative example, when a threshold of detection is 10 nM, then a signal can be detected when a target DNA is present in the sample at a concentration of 10 nM or more. In certain embodiments, a method of the present disclosure has a threshold of detection of 5 nM or less. In certain embodiments, a method of the present disclosure has a threshold of detection of 1 nM or less. In certain embodiments, a method of the present disclosure has a threshold of detection of 0.5 nM or less. In certain embodiments, a method of the present disclosure has a threshold of detection of 0.1 nM or less. In certain embodiments, a method of the present disclosure has a threshold of detection of 0.05 nM or less. In certain embodiments, a method of the present disclosure has a threshold of detection of 0.01 nM or less. In certain embodiments, a method of the present disclosure has a threshold of detection of 0.005 nM or less. In certain embodiments, a method of the present disclosure has a threshold of detection of 0.001 nM or less. In certain embodiments, a method of the present disclosure has a threshold of detection of 0.0005 nM or less. In certain embodiments, a method of the present disclosure has a threshold of detection of 0.0001 nM or less. In certain embodiments, a method of the present disclosure has a threshold of detection of 0.00005 nM or less. In certain embodiments, a method of the present disclosure has a threshold of detection of 0.00001 nM or less. In certain embodiments, a method of the present disclosure has a threshold of detection of 10 pM or less. In certain embodiments, a method of the present disclosure has a threshold of detection of 1 pM or less. In certain embodiments, a method of the present disclosure has a threshold of detection of 500 fM or less. In certain embodiments, a method of the present disclosure has a threshold of detection of 250 fM or less. In certain embodiments, a method of the present disclosure has a threshold of detection of 100 fM or less. In certain embodiments, a method of the present disclosure has a threshold of detection of 50 fM or less. In certain embodiments, a method of the present disclosure has a threshold of detection of 500 aM (attomolar) or less. In certain embodiments, a method of the present disclosure has a threshold of detection of 250 aM or less.

In certain embodiments, a method of the present disclosure has a threshold of detection of 100 aM or less. In certain embodiments, a method of the present disclosure has a threshold of detection of 50 aM or less. In certain embodiments, a method of the present disclosure has a threshold of detection of 10 aM or less. In certain embodiments, a method of the present disclosure has a threshold of detection of 1 aM or less.

In certain embodiments, the threshold of detection (for detecting the target DNA in a subject method), is in a range of from 500 fM to 1 nM (e.g., from 500 fM to 500 pM, from 500 fM to 200 pM, from 500 fM to 100 pM, from 500 fM to 10 pM, from 500 fM to 1 pM, from 800 fM to 1 nM, from 800 fM to 500 pM, from 800 fM to 200 pM, from 800 fM to 100 pM, from 800 fM to 10 pM, from 800 fM to 1 pM, from 1 pM to 1 nM, from 1 pM to 500 pM, from 1 pM to 200 pM, from 1 pM to 100 pM, or from 1 pM to 10 pM) (where the concentration refers to the threshold concentration of target DNA at which the target DNA can be detected). In certain embodiments, a method of the present disclosure has a threshold of detection in a range of from 800 fM to 100 pM. In certain embodiments, a method of the present disclosure has a threshold of detection in a range of from 1 pM to 10 pM. In certain embodiments, a method of the present disclosure has a threshold of detection in a range of from 10 fM to 500 fM, e.g., from 10 fM to 50 fM, from 50 fM to 100 fM, from 100 fM to 250 fM, or from 250 fM to 500 fM.

In certain embodiments, the minimum concentration at which a target DNA can be detected in a sample is in a range of from 500 fM to 1 nM (e.g., from 500 fM to 500 pM, from 500 fM to 200 pM, from 500 fM to 100 pM, from 500 fM to 10 pM, from 500 fM to 1 pM, from 800 fM to 1 nM, from 800 fM to 500 pM, from 800 fM to 200 pM, from 800 fM to 100 pM, from 800 fM to 10 pM, from 800 fM to 1 pM, from 1 pM to 1 nM, from 1 pM to 500 pM, from 1 pM to 200 pM, from 1 pM to 100 pM, or from 1 pM to 10 pM). In certain embodiments, the minimum concentration at which a target DNA can be detected in a sample is in a range of from 800 fM to 100 pM. In certain embodiments, the minimum concentration at which a target DNA can be detected in a sample is in a range of from 1 pM to 10 pM.

In certain embodiments, the threshold of detection (for detecting the target DNA in a subject method), is in a range of from 1 aM to 1 nM (e.g., from 1 aM to 500 pM, from 1 aM to 200 pM, from 1 aM to 100 pM, from 1 aM to 10 pM, from 1 aM to 1 pM, from 100 aM to 1 nM, from 100 aM to 500 pM, from 100 aM to 200 pM, from 100 aM to 100 pM, from 100 aM to 10 pM, from 100 aM to 1 pM, from 250 aM to 1 nM, from 250 aM to 500 pM, from 250 aM to 200 pM, from 250 aM to 100 pM, from 250 aM to 10 pM, from 250 aM to 1 pM, from 500 aM to 1 nM, from 500 aM to 500 pM, from 500 aM to 200 pM, from 500 aM to 100 pM, from 500 aM to 10 pM, from 500 aM to 1 pM, from 750 aM to 1 nM, from 750 aM to 500 pM, from 750 aM to 200 pM, from 750 aM to 100 pM, from 750 aM to 10 pM, from 750 aM to 1 pM, from 1 fM to 1 nM, from 1 fM to 500 pM, from 1 fM to 200 pM, from 1 fM to 100 pM, from 1 fM to 10 pM, from 1 fM to 1 pM, from 500 fM to 500 pM, from 500 fM to 200 pM, from 500 fM to 100 pM, from 500 fM to 10 pM, from 500 fM to 1 pM, from 800 fM to 1 nM, from 800 fM to 500 pM, from 800 fM to 200 pM, from 800 fM to 100 pM, from 800 fM to 10 pM, from 800 fM to 1 pM, from 1 pM to 1 nM, from 1 pM to 500 pM, from 1 pM to 200 pM, from 1 pM to 100 pM, or from 1 pM to 10 pM) (where the concentration refers to the threshold concentration of target DNA at which the target DNA can be detected). In certain embodiments, a method of the present disclosure has a threshold of detection in a range of from 1 aM to 800 aM. In certain embodiments, a method of the present disclosure has a threshold of detection in a range of from 50 aM to 1 pM. In certain embodiments, a method of the present disclosure has a threshold of detection in a range of from 50 aM to 500 fM.

In certain embodiments, the minimum concentration at which a target DNA can be detected in a sample is in a range of from 1 aM to 1 nM (e.g., from 1 aM to 500 pM, from 1 aM to 200 pM, from 1 aM to 100 pM, from 1 aM to 10 pM, from 1 aM to 1 pM, from 100 aM to 1 nM, from 100 aM to 500 pM, from 100 aM to 200 pM, from 100 aM to 100 pM, from 100 aM to 10 pM, from 100 aM to 1 pM, from 250 aM to 1 nM, from 250 aM to 500 pM, from 250 aM to 200 pM, from 250 aM to 100 pM, from 250 aM to 10 pM, from 250 aM to 1 pM, from 500 aM to 1 nM, from 500 aM to 500 pM, from 500 aM to 200 pM, from 500 aM to 100 pM, from 500 aM to 10 pM, from 500 aM to 1 pM, from 750 aM to 1 nM, from 750 aM to 500 pM, from 750 aM to 200 pM, from 750 aM to 100 pM, from 750 aM to 10 pM, from 750 aM to 1 pM, from 1 fM to 1 nM, from 1 fM to 500 pM, from 1 fM to 200 pM, from 1 fM to 100 pM, from 1 fM to 10 pM, from 1 fM to 1 pM, from 500 fM to 500 pM, from 500 fM to 200 pM, from 500 fM to 100 pM, from 500 fM to 10 pM, from 500 fM to 1 pM, from 800 fM to 1 nM, from 800 fM to 500 pM, from 800 fM to 200 pM, from 800 fM to 100 pM, from 800 fM to 10 pM, from 800 fM to 1 pM, from 1 pM to 1 nM, from 1 pM to 500 pM, from 1 pM to 200 pM, from 1 pM to 100 pM, or from 1 pM to 10 pM). In certain embodiments, the minimum concentration at which a target DNA can be detected in a sample is in a range of from 1 aM to 500 pM. In certain embodiments, the minimum concentration at which a target DNA can be detected in a sample is in a range of from 100 aM to 500 pM.

In certain embodiments, a subject composition or method exhibits an attomolar (aM) sensitivity of detection. In certain embodiments, a subject composition or method exhibits a femtomolar (fM) sensitivity of detection. In certain embodiments, a subject composition or method exhibits a picomolar (pM) sensitivity of detection. In certain embodiments, a subject composition or method exhibits a nanomolar (nM) sensitivity of detection.

Target DNA

A target DNA can be single stranded (ssDNA) or double stranded (dsDNA). When the target DNA is single stranded, there is no preference or requirement for a PAM sequence in the target DNA. However, when the target DNA is dsDNA, a PAM is usually present adjacent to the target sequence of the target DNA (e.g., see discussion of the PAM elsewhere herein). The source of the target DNA can be the same as the source of the sample, e.g., as described below.

The source of the target DNA can be any source. In certain embodiments, the target DNA is a bacterial plant pathogen DNA (e.g., a genomic DNA of a bacterial plant pathogen). As such, a subject method can be for detecting the presence of a bacterial plant pathogen DNA amongst a population of nucleic acids (e.g., in a sample). Examples of possible target DNAs include, but are not limited to, a genomic DNA of a bacterial plant pathogen such as Acidovorax *avenae, Agrobacterium tumefaciens, Burkholderia andropogonis, Burkholderia caryophylli, Burkholderia glumae, Candidatus Liberibacter asiaticus, Candidatus Liberibacter solanacearum, Candidatus Phytoplasma solani, Candidatus Phytoplasma trifolii, Clavibacter michiganensis, Dickeya dadantii, Erwinia amylovora, Erwinia psidii, Pectobacterium atrosepticum, Pectobacterium betavasculorum, Pectobacterium carotovorum, Pectobacterium wasabiae, Pseudomonas amygdali, Pseudomonas asplenii, Pseudomonas caricapapayae, Pseudomonas cichorii, Pseudomonas coronafaciens, Pseudomonas corrugate, Pseudomonas ficuserectae, Pseudomonas flavescens, Pseudomonas fuscovaginae,*

*Pseudomonas helianthi, Pseudomonas* margina/is, *Pseudomonas oryzihabitans, Pseudomonas palleroniana, Pseudomonas papaveris, Pseudomonas salomonii, Pseudomonas savastanoi, Pseudomonas syringae, Pseudomonas tomato, Pseudomonas turbinellae, Pseudomonas viridiflava, Ralstonia solanacearum, Rhodococcus fascians, Spiroplasma citri, Xanthomonas axonopodis, Xanthomonas campestris, Xanthomonas oryzae*, and *Xylella fastidiosa.*

In certain embodiments, the bacterial plant pathogen is from the genus *Candidatus Liberibacter* (i.e., *Candidatus liberibacter* spp.). Extensive economic loss in citrus production has occurred due to the citrus greening disease or Huanglongbing (HLB) caused by phloem-limited, fastidious, gram-negative bacteria in *Candidatus liberibacter* spp. This genus includes three HLB-associated species, *Candidatus L. africanus* (CLaf), *Candidatus L. americanus* (CLam) and *Candidatus L. asiaticus* (CLas) with CLas being the most devastating and broadly distributed species worldwide. CLas is transmitted via natural insect vectors such as citrus psyllids or through the grafting of infected tissues. In order to manage CLas, it is critical to utilize early detection technology for disease diagnosis and quarantine of CLas-infected crops and insect vectors to minimize crop loss and prevent transmission into disease-free citrus growing regions.

In certain embodiments, the bacterial plant pathogen is from the genus *Candidatus Phytoplasma* (i.e., *Candidatus Phytoplasma* spp.). Over the past decade, emerging diseases caused by phytoplasmas have been observed at an increasingly rapid pace worldwide. Phytoplasmas are cell wall-less bacteria that inhabit the phloem tissues of infected plants and are spread by sap sucking insect vectors, mainly leafhoppers and psyllids. Phytoplasmas can also be transmitted by grafting or vegetative propagation of diseased tissues. Since phytoplasmas cannot be cultured in cell-free media, their identification and classification were previously based on biological properties such as symptoms of infected plants, host-plant range, and their relationship with insect vectors. With the advancement of molecular techniques such as polymerase chain reaction (PCR), restriction fragment length polymorphism (RFLP) profiling, and DNA sequencing, the phylogenetic relationship among diverse phytoplasmas became evident. As a result, a molecular marker-based classification scheme was developed and a provisional genus '*Candidatus phytoplasma*' was established. To date, 45 *Candidatus phytoplasma* species have been formally described; and over one thousand known phytoplasma strains have been classified into 36 groups and more than 150 subgroups based on RFLP profiles of the 16S rRNA gene.

Across the United States and Mexico, emerging phytoplasma diseases in potato (*Solanum tuberosum* L.) and other vegetable crops have become increasingly common. As a result, they are causing considerable economic losses to local industries in terms of the quality and quantity of crop production. Among the phytoplasma-associated potato diseases, potato purple top (PPT) and potato witches' broom (PWB) are the most commonly observed diseases across the Pacific Coast of North America, forming the PPT disease complex. PPT-affected plants often wilt and die prematurely, significantly reducing the quality and yield of tubers. On the other hand, PWB-affected potato plants typically produce numerous small tubers with shortened dormancy and poor marketability. PPT disease complex in different geographic regions has been attributed to infections by at least five mutually distinct phytoplasma species, including 'Ca. *Phytoplasma asteris*', 'Ca. *Phytoplasma aurantifolia*', 'Ca. *Phytoplasma pruni*', 'Ca. *Phytoplasma trifolii*', and 'Ca. *Phytoplasma americanum*'. These five phytoplasma species are classified into the aster yellows group (16SrI), the peanut witches'-broom group (16SrII), the X-disease group (16SrIII), the clover proliferation group (16SrVI), and the American potato purple top wilt group (16SrXVIII), respectively. Since various phytoplasmas may be transmitted by different vectors and have different reservoirs, early disease diagnosis and accurate identification of the phytoplasmas involved are crucial to devising disease control strategies that precisely target the specific vectors and reservoirs.

In certain embodiments, the bacterial plant pathogen is *Candidatus Phytoplasma trifolii*. 'Ca. *Phytoplasma trifolii*' has a broad host range and a wide geographic distribution. Agriculturally important leguminous, solanaceous, and brassicas crops are among the most common hosts of 'Ca. *Phytoplasma trifolii*'. The reference strain of the species, clover proliferation phytoplasma (CPR), is the type member of the subgroup 16SrVI-A. The 'Ca. *Phytoplasma trifolii*'-related strains responsible for repeated PPT outbreaks in the Pacific Northwest of the United States since 2002 also belongs to subgroup 16SrVI-A and have a trivial name "beet leafhopper transmitted virescence agent". Notably, while the North American PWB phytoplasma strains induce symptoms distinctly different from that of PPT, they belong to subgroup 16SrVI-A as well. Their insect vectors' widespread and polyphagous nature makes the transmission of the PPT and PWB phytoplasmas easy and mixed infection inevitable. Therefore, accurate and early diagnosis of PPT and PWB is crucial and considered to be one of the most effective measures for disease management. Favorably, since PPT and PWB phytoplasmas belong to the same subgroup lineage, they possess nearly-identical 16S-23S ribosomal DNA (rDNA) intergenic transcribed spacer (ITS) sequences, providing a common target for simultaneous detection of both phytoplasmas of the disease complex.

Samples

A subject sample includes nucleic acid (e.g., a plurality of nucleic acids). The term "plurality" is used herein to mean two or more. Thus, in certain embodiments, a sample includes two or more (e.g., 3 or more, 5 or more, 10 or more, 20 or more, 50 or more, 100 or more, 500 or more, 1,000 or more, or 5,000 or more) nucleic acids (e.g., DNAs). A subject method can be used as a very sensitive way to detect a target DNA present in a sample (e.g., in a complex mixture of nucleic acids such as DNAs). In certain embodiments, the sample includes 5 or more DNAs (e.g., 10 or more, 20 or more, 50 or more, 100 or more, 500 or more, 1,000 or more, or 5,000 or more DNAs) that differ from one another in sequence. In certain embodiments, the sample includes 10 or more, 20 or more, 50 or more, 100 or more, 500 or more, $10^3$ or more, $5\times10^3$ or more, $10^4$ or more, $5\times10^4$ or more, $10^5$ or more, $5\times10^5$ or more, $10^6$ or more $5\times10^6$ or more, or $10^7$ or more, DNAs. In certain embodiments, the sample comprises from 10 to 20, from 20 to 50, from 50 to 100, from 100 to 500, from 500 to $10^3$, from $10^3$ to $5\times10^3$, from $5\times10^3$ to $10^4$, from $10^4$ to $5\times10^4$, from $5\times10^4$ to $10^5$, from $10^5$ to $5\times10^5$, from $5\times10^5$ to $10^6$, from $10^6$ to $5\times10^6$, or from $5\times10^6$ to $10^7$, or more than $10^7$, DNAs. In certain embodiments, the sample comprises from 5 to $10^7$ DNAs (e.g., that differ from one another in sequence)(e.g., from 5 to $10^6$, from 5 to $10^5$, from 5 to 50,000, from 5 to 30,000, from 10 to $10^6$, from 10 to $10^5$, from 10 to 50,000, from 10 to 30,000, from 20 to $10^6$, from 20 to $10^5$, from 20 to 50,000, or from 20 to 30,000 DNAs). In certain embodiments, the sample includes 20 or more DNAs that differ from one another in sequence. In certain embodiments, the sample includes DNAs from a cell lysate (e.g., a plant cell lysate). For example, in certain embodiments, the sample includes DNA from a cell such as a plant cell, e.g., a Citrus cell or a *Solanum* cell.

The term "sample" is used herein to mean any sample that includes DNA (e.g., in order to determine whether a target DNA is present among a population of DNAs). The sample can be derived from any source, e.g., the sample can be a synthetic combination of purified DNAs; the sample can be a cell lysate, an DNA-enriched cell lysate, or DNAs isolated and/or purified from a cell lysate. The sample can be from a plant (e.g., for the purpose of detecting a bacterial plant pathogen).

A "sample" can include a target DNA and a plurality of non-target DNAs. In certain embodiments, the target DNA is present in the sample at one copy per 10 non-target DNAs, one copy per 20 non-target DNAs, one copy per 25 non-target DNAs, one copy per 50 non-target DNAs, one copy per 100 non-target DNAs, one copy per 500 non-target DNAs, one copy per $10^3$ non-target DNAs, one copy per $5\times10^3$ non-target DNAs, one copy per 104 non-target DNAs, one copy per $5\times10^4$ non-target DNAs, one copy per $10^5$ non-target DNAs, one copy per $5\times10^5$ non-target DNAs, one copy per $10^6$ non-target DNAs, or less than one copy per $10^6$ non-target DNAs. In certain embodiments, the target DNA is present in the sample at from one copy per 10 non-target DNAs to 1 copy per 20 non-target DNAs, from 1 copy per 20 non-target DNAs to 1 copy per 50 non-target DNAs, from 1 copy per 50 non-target DNAs to 1 copy per 100 non-target DNAs, from 1 copy per 100 non-target DNAs to 1 copy per 500 non-target DNAs, from 1 copy per 500 non-target DNAs to 1 copy per $10^3$ non-target DNAs, from 1 copy per $10^3$ non-target DNAs to 1 copy per $5\times10^3$ non-target DNAs, from 1 copy per $5\times10^3$ non-target DNAs to 1 copy per $10^4$ non-target DNAs, from 1 copy per $10^4$ non-target DNAs to 1 copy per $10^5$ non-target DNAs, from 1 copy per $10^5$ non-target DNAs to 1 copy per $10^6$ non-target DNAs, or from 1 copy per $10^6$ non-target DNAs to 1 copy per $10^7$ non-target DNAs.

A sample can comprise, or can be obtained from, any of a variety of plant cells, tissues, or organs. Plant cells include cells of a monocotyledon and cells of a dicotyledon. The cells can be root cells, leaf cells, cells of the xylem, cells of the phloem, cells of the cambium, apical meristem cells, parenchyma cells, collenchyma cells, sclerenchyma cells, and the like. In certain embodiments, the source of the sample is a normal (non-diseased) plant cell, tissue, or organ. In certain embodiments, the source of the sample is a pathogen-infected (or is suspected of being a pathogen-infected) plant cell, tissue, or organ. For example, the source of a sample can be a plant that may or may not be infected with a bacterial pathogen. In certain embodiments, the sample can comprise cells. In certain embodiments, the sample can comprise a cell lysate.

Examples of plants of interest include, but are not limited to, corn (*Zea mays*), *Brassica* spp. (e.g., *B. napus, B. rapa, B. juncea*), alfalfa (*Medicago sativa*), rice (*Oryza sativa*), rye (*Secale cereale*), sorghum (*Sorghum bicolor, Sorghum vulgare*), millet (e.g., pearl millet (*Pennisetum glaucum*), proso millet (*Panicum miliaceum*), foxtail millet (*Setaria italica*), finger millet (*Eleusine coracana*)), sunflower (*Helianthus annuus*), safflower (*Carthamus tinctorius*), wheat (*Triticum aestivum*), soybean (*Glycine max*), tobacco (*Nicotiana tabacum*), potato (*Solanum tuberosum*), peanuts (*Arachis hypogaea*), cotton (*Gossypium barbadense, Gossypium hirsutum*), sweet potato (*Ipomoea batatus*), cassava (*Manihot esculenta*), coffee (*Coffea* spp.), coconut (*Cocos nucifera*), pineapple (*Ananas comosus*), Citrus (*Citrus* spp.), cocoa (*Theobroma cacao*), tea (*Camellia sinensis*), banana (*Musa* spp.), avocado (*Persea americana*), fig (*Ficus casica*), guava (*Psidium guajava*), mango (*Mangifera indica*), grapevine (*Vitis vinifera*), olive (*Olea europaea*), *papaya* (*Carica papaya*), cashew (*Anacardium occidentale*), macadamia (*Macadamia integrifolia*), almond (*Prunus amygdalus*), sugar beets (*Beta vulgaris*), sugarcane (*Saccharum* spp.), oat (*Avena sativa*), barley (*Hordeum vulgare*), vegetables, ornamentals, and conifers.

In certain embodiments, the plant is *Citrus*. The term "*Citrus*", as used herein, refers to any plant of the genus *Citrus*, family Rutaceae, and includes *Citrus maxima* (Pomelo), *Citrus medica* (Citron), *Citrus micrantha* (Papeda), *Citrus reticulata* (Mandarin orange), *Citrus trifolata* (trifoliate orange), *Citrus japonica* (kumquat), *Citrus australasica* (Australian Finger Lime), *Citrus australis* (Australian Round lime), *Citrus glauca* (Australian Desert Lime), *Citrus garrawayae* (Mount White Lime), *Citrus gracilis* (Kakadu Lime or Humpty Doo Lime), *Citrus inodora* (Russel River Lime), *Citrus warburgiana* (New Guinea Wild Lime), *Citrus wintersii* (Brown River Finger Lime), *Citrus halimii* (limau kadangsa, limau kedut kera); *Citrus indica* (Indian wild orange), *Citrus macroptera*, and *Citrus latipes*. Hybrids also are included in this definition, for example *Citrus* x *aurantiifolia* (Key lime), *Citrus* x *aurantium* (Bitter orange), *Citrus* x *latifolia* (Persian lime), *Citrus* x *limon* (Lemon), *Citrus* x *limonia* (Rangpur), *Citrus* x *paradisi* (Grapefruit), *Citrus* x *sinensis* (Sweet orange), *Citrus* x *tangerina* (Tangerine), *Poncirus trifoliata* x *C. sinensis* (Carrizo citrange), and any other known species or hybrid of genus *Citrus*. *Citrus* known by their common names include, Imperial lemon, tangelo, orangelo, tangor, kinnow, kiyomi, Minneola tangelo, oroblanco, sweet orange, ugli, Buddha's hand, citron, lemon, orange, bergamot orange, bitter orange, blood orange, calamondin, clementine, grapefruit, Meyer lemon, Rangpur, tangerine, and yuzu, and these also are included in the definition of *Citrus*.

Detecting a Signal

In certain embodiments, a subject method includes a step of detecting (e.g., detecting a signal produced by Type V CRISPR/Cas effector protein (e.g., a Cas12 protein such as Cas12a, Cas12b, Cas12c, Cas12d, Cas12e)-mediated ssDNA cleavage). Because a Type V CRISPR/Cas effector protein (e.g., a Cas12 protein such as Cas12a, Cas12b, Cas12c, Cas12d, Cas12e) cleaves non-targeted ssDNA once activated, which occurs when a guide RNA hybridizes with a target DNA in the presence of a Type V CRISPR/Cas effector protein (e.g., a Cas12 protein such as Cas12a, Cas12b, Cas12c, Cas12d, Cas12e), a detectable signal can be any signal that is produced when ssDNA is cleaved. For example, in certain embodiments, the step of detecting can include one or more of: gold nanoparticle based detection (e.g., see Xu et al., Angew Chem Int Ed Engl. 2007; 46(19):3468-70; and Xia et al., Proc Natl Acad Sci USA. 2010 Jun. 15; 107(24):10837-41), fluorescence polarization, colloid phase transition/dispersion (e.g., Baksh et al., Nature. 2004 Jan. 8; 427(6970):139-41), electrochemical detection, semiconductor-based sensing (e.g., Rothberg et al., Nature. 2011 Jul. 20; 475(7356):348-52; e.g., one could use a phosphatase to generate a pH change after ssDNA cleavage reactions, by opening 2'-3' cyclic phosphates, and by releasing inorganic phosphate into solution), and detection of a labeled ssDNA reporter oligonucleotide (see elsewhere herein for more details). The readout of such detection methods can be any convenient readout. Examples of possible readouts include but are not limited to: a measured amount of detectable fluorescent signal; a visual analysis of bands on a gel (e.g., bands that represent cleaved product versus uncleaved substrate), a visual or sensor based detection of the presence or absence of a color (i.e., color detection method), and the presence or absence of (or a particular amount of) an electrical signal.

The detecting can, in certain embodiments, be quantitative, e.g., in the sense that the amount of signal detected can be used to determine the amount of target DNA present in the sample. The detecting can, in certain embodiments, be qualitative, e.g., in the sense that the presence or absence of detectable signal can indicate the presence or absence of targeted DNA (e.g., bacterial plant pathogen). In certain embodiments, a detectable signal will not be present (e.g., above a given threshold level) unless the targeted DNA (e.g., bacterial plant pathogen) is present above a particular threshold concentration. In certain embodiments, the threshold of detection can be titrated by modifying the amount of Type V CRISPR/Cas effector protein (e.g., a Cas12 protein such as Cas12a, Cas12b, Cas12c, Cas12d, Cas12e), guide RNA, sample volume, and/or ssDNA reporter oligonucleotide (if one is used). As such, for example, as would be understood by one of ordinary skill in the art, a number of controls can be used if desired in order to set up one or more reactions, each set up to detect a different threshold level of target DNA, and thus such a series of reactions could be used to determine the amount of target DNA present in a sample (e.g., one could use such a series of reactions to determine that a target DNA is present in the sample 'at a concentration of at least X').

In certain embodiments, a method of the present disclosure can be used to determine the amount of a target DNA in a sample (e.g., a sample comprising the target DNA and a plurality of non-target DNAs). Determining the amount of a target DNA in a sample can comprise comparing the amount of detectable signal generated from a test sample to the amount of detectable signal generated from a reference sample. Determining the amount of a target DNA in a sample can comprise: measuring the detectable signal to generate a test measurement; measuring a detectable signal produced by a reference sample to generate a reference measurement; and comparing the test measurement to the reference measurement to determine an amount of target DNA present in the sample.

For example, in certain embodiments, a method of the present disclosure for determining the amount of a target DNA in a sample comprises: a) contacting the sample (e.g., a sample comprising the target DNA and a plurality of non-target DNAs) with: (i) a guide RNA that hybridizes with the target DNA, (ii) a Type V CRISPR/Cas effector protein (e.g., a Cas12 protein such as Cas12a, Cas12b, Cas12c, Cas12d, Cas12e) that cleaves RNAs present in the sample, and (iii) a ssDNA reporter oligonucleotide; b) measuring a detectable signal produced by Type V CRISPR/Cas effector protein (e.g., a Cas12 protein such as Cas12a, Cas12b, Cas12c, Cas12d, Cas12e)-mediated ssDNA cleavage (e.g., cleavage of the ssDNA reporter oligonucleotide), generating a test measurement; c) measuring a detectable signal produced by a reference sample to generate a reference measurement; and d) comparing the test measurement to the reference measurement to determine an amount of target DNA present in the sample.

As another example, in certain embodiments, a method of the present disclosure for determining the amount of a target DNA in a sample comprises: a) contacting the sample (e.g., a sample comprising the target DNA and a plurality of non-target DNAs) with: i) a precursor guide RNA array comprising two or more guide RNAs each of which has a different spacer sequence; (ii) a Type V CRISPR/Cas effector protein (e.g., a Cas12 protein such as Cas12a, Cas12b, Cas12c, Cas12d, Cas12e) that cleaves the precursor guide RNA array into individual guide RNAs, and also cleaves RNAs of the sample; and (iii) a ssDNA reporter oligonucleotide; b) measuring a detectable signal produced by Type V CRISPR/Cas effector protein (e.g., a Cas12 protein such as Cas12a, Cas12b, Cas12c, Cas12d, Cas12e)-mediated ssDNA cleavage (e.g., cleavage of the ssDNA reporter oligonucleotide), generating a test measurement; c) measuring a detectable signal produced by each of two or more reference samples to generate two or more reference measurements; and d) comparing the test measurement to the reference measurements to determine an amount of target DNA present in the sample.

Amplification of Nucleic Acids in the Sample

In certain embodiments, sensitivity of a subject composition and/or method (e.g., for detecting the presence of a target DNA, such as bacterial plant pathogen DNA, in plant cellular genomic DNA) can be increased by coupling detection with nucleic acid amplification. In certain embodiments, the nucleic acids in a sample are amplified prior to contact with a type V CRISPR/Cas effector protein (e.g., a Cas12 protein) that cleaved ssDNA (e.g., amplification of nucleic acids in the sample can begin prior to contact with a type V CRISPR/Cas effector protein). In certain embodiments, the nucleic acids in a sample are amplified simultaneous with contact with a type V CRISPR/Cas effector protein (e.g., a Cas12 protein). For example, in certain embodiments, a subject method includes amplifying nucleic acids of a sample (e.g., by contacting the sample with amplification components) prior to contacting the amplified sample with a type V CRISPR/Cas effector protein (e.g., a Cas12 protein). In certain embodiments, a subject method includes contacting a sample with amplification components at the same time (simultaneous with) that the sample is contacted with a type V CRISPR/Cas effector protein (e.g., a Cas12 protein). If all components are added simultaneously (amplification components and detection components such as a type V CRISPR/Cas effector protein, e.g., a Cas12 protein, a guide RNA, and a reporter oligonucleotide), it is possible that the trans-cleavage activity of the type V CRISPR/Cas effector protein (e.g., a Cas12 protein), will begin to degrade the nucleic acids of the sample at the same time the nucleic acids are undergoing amplification. However, even if this is the case, amplifying and detecting simultaneously can still increase sensitivity compared to performing the method without amplification.

In certain embodiments, specific sequences (e.g., sequences of a bacterial plant pathogen) are amplified from the sample, e.g., using primers. As such, a sequence to which the guide RNA will hybridize can be amplified in order to increase sensitivity of a subject detection method—this could achieve biased amplification of a desired sequence in order to increase the number of copies of the sequence of interest present in the sample relative to other sequences present in the sample. As one illustrative example, if a subject method is being used to determine whether a given sample includes a particular bacterial plant pathogen, a desired region of bacterial plant pathogen sequence can be amplified, and the region amplified will include the sequence that would hybridize to the guide RNA if the bacterial plant pathogen sequence were in fact present in the sample.

Primers are provided which are of sufficient nucleotide length to bind specifically to the target DNA sequence under the reaction or hybridization conditions. In certain embodiments, primers are at least 10, 11, 12, 13, 14, 15, 16, 17, 18, 19, 20, 21, 22, 23, 24, 25, 26, 27, 28, 29 or 30 nucleotides in length, and less than 35, 34, 33, 32, 31, 30, 29, 28, 27, 26, 2, 5 2, 4 23, 22, 21, 20, 19, 18, 17, 16, 15, 14, 13, or 12 nucleotides in length. In certain embodiments, such primers can hybridize specifically to a target sequence under high stringency hybridization conditions. In certain embodiments, primers have complete or 100% DNA sequence similarity of contiguous nucleotides with the target sequence, although primers which differ from the target DNA sequence but retain the ability to hybridize to target DNA sequence may also be used. Reverse complements of the primers and probes disclosed herein are also provided and can be used in the methods and compositions described herein. In certain embodiments, the primers bind to the target sequence to produce an amplicon of a length described herein. The amplicon molecule produced can be at least 5, 10, 15, 20, 25, 30, 35, 40, 41, 42, 43, 44, 45, 46, 47, 48, 49, 50, 60, 70, 80, 90, 100, 125, 150, 175, 200, 225, 250, 275, 300, 350, 400, 450, 500, 550, 600, 650, 700, 750, 800, 850, 900, 950, 1000, 1500 or 2000 nucleotides in length and less than about 10000, 9000, 8000, 7500, 7000, 6500, 6000, 5500, 5000, 4500, 4000, 3500, 3000, 2500, 2000, or 1500 nucleotides in length.

As noted, in certain embodiments, the nucleic acids are amplified (e.g., by contact with amplification components) prior to contacting the amplified nucleic acids with a type V CRISPR/Cas effector protein (e.g., a Cas12 protein). In certain embodiments, amplification occurs for 10 seconds or more, (e.g., 30 seconds or more, 45 seconds or more, 1 minute or more, 2 minutes or more, 3 minutes or more, 4 minutes or more, 5 minutes or more, 7.5 minutes or more, 10 minutes or more, etc.) prior to contact with an active type V CRISPR/Cas effector protein (e.g., a Cas12 protein). In certain embodiments, amplification occurs for 2 minutes or more (e.g., 3 minutes or more, 4 minutes or more, 5 minutes or more, 7.5 minutes or more, 10 minutes or more, etc.) prior to contact with an active type V CRISPR/Cas effector protein (e.g., a Cas12 protein). In certain embodiments, amplification occurs for a period of time in a range of from 10 seconds to 60 minutes (e.g., 10 seconds to 40 minutes, 10 seconds to 30 minutes, 10 seconds to 20 minutes, 10 seconds to 15 minutes, 10 seconds to 10 minutes, 10 seconds to 5 minutes, 30 seconds to 40 minutes, 30 seconds to 30 minutes, 30 seconds to 20 minutes, 30 seconds to 15 minutes, 30 seconds to 10 minutes, 30 seconds to 5 minutes, 1 minute to 40 minutes, 1 minute to 30 minutes, 1 minute to 20 minutes, 1 minute to 15 minutes, 1 minute to 10 minutes, 1 minute to 5 minutes, 2 minutes to 40 minutes, 2 minutes to 30 minutes, 2 minutes to 20 minutes, 2 minutes to 15 minutes, 2 minutes to 10 minutes, 2 minutes to 5 minutes, 5 minutes to 40 minutes, 5 minutes to 30 minutes, 5 minutes to 20 minutes, 5 minutes to 15 minutes, or 5 minutes to 10 minutes). In certain embodiments, amplification occurs for a period of time in a range of from 5 minutes to 15 minutes. In certain embodiments, amplification occurs for a period of time in a range of from 7 minutes to 12 minutes.

In certain embodiments, a sample is contacted with amplification components at the same time as contact with a type V CRISPR/Cas effector protein (e.g., a Cas12 protein). In certain such embodiments, the type V CRISPR/Cas effector protein is inactive at the time of contact and is activated once nucleic acids in the sample have been amplified.

Various amplification methods and components will be known to one of ordinary skill in the art and any convenient method can be used (see, e.g., Zanoli and Spoto, Biosensors (Basel). 2013 March; 3(1): 18-43; Gill and Ghaemi, Nucleosides, Nucleotides, and Nucleic Acids, 2008, 27: 224-243; Craw and Balachandrana, Lab Chip, 2012, 12, 2469-2486; which are herein incorporated by reference in their entirety). Nucleic acid amplification can comprise polymerase chain reaction (PCR), reverse transcription PCR (RT-PCR), quantitative PCR (qPCR), reverse transcription qPCR (RT-qPCR), nested PCR, multiplex PCR, asymmetric PCR, touchdown PCR, random primer PCR, hemi-nested PCR, polymerase cycling assembly (PCA), colony PCR, ligase chain reaction (LCR), digital PCR, methylation specific-PCR (MSP), co-amplification at lower denaturation temperature-PCR (COLD-PCR), allele-specific PCR, intersequence-specific PCR (ISS-PCR), whole genome amplification (WGA), inverse PCR, and thermal asymmetric interlaced PCR (TAIL-PCR).

In certain embodiments, the amplification is isothermal amplification. The term "isothermal amplification" indicates a method of nucleic acid (e.g., DNA) amplification (e.g., using enzymatic chain reaction) that can use a single temperature incubation thereby obviating the need for a thermal cycler. Isothermal amplification is a form of nucleic acid amplification which does not rely on the thermal denaturation of the target nucleic acid during the amplification reaction and hence may not require multiple rapid changes in temperature. Isothermal nucleic acid amplification methods can therefore be carried out inside or outside of a laboratory environment. By combining with a reverse transcription step, these amplification methods can be used to isothermally amplify RNA.

Examples of isothermal amplification methods include but are not limited to: loop-mediated isothermal Amplification (LAMP), helicase-dependent Amplification (HDA), recombinase polymerase amplification (RPA), strand displacement amplification (SDA), nucleic acid sequence-based amplification (NASBA), transcription mediated amplification (TMA), nicking enzyme amplification reaction (NEAR), rolling circle amplification (RCA), multiple displacement amplification (MDA), Ramification (RAM), circular helicase-dependent amplification (cHDA), single primer isothermal amplification (SPIA), signal mediated amplification of RNA technology (SMART), self-sustained sequence replication (3SR), genome exponential amplification reaction (GEAR) and isothermal multiple displacement amplification (IMDA).

In certain embodiments, the amplification is recombinase polymerase amplification (RPA) (see, e.g., U.S. Pat. Nos. 8,030,000; 8,426,134; 8,945,845; 9,309,502; and 9,663,820, which are hereby incorporated by reference in their entirety). Recombinase polymerase amplification (RPA) uses two opposing primers (much like PCR) and employs three enzymes—a recombinase, a single-stranded DNA-binding protein (SSB) and a strand-displacing polymerase. The recombinase pairs oligonucleotide primers with homologous sequence in duplex DNA, SSB binds to displaced strands of DNA to prevent the primers from being displaced, and the strand displacing polymerase begins DNA synthesis where the primer has bound to the target DNA. Adding a reverse transcriptase enzyme to an RPA reaction can facilitate detection RNA as well as DNA, without the need for a separate step to produce cDNA.

One example of components for an RPA reaction is as follows (see, e.g., U.S. Pat. Nos. 8,030,000; 8,426,134; 8,945,845; 9,309,502; 9,663,820): 50 mM Tris pH 8.4, 80 mM Potassium actetate, 10 mM Magnesium acetate, 2 mM DTT, 5% PEG compound (Carbowax-20M), 3 mM ATP, 30 mM Phosphocreatine, 100 ng/μl creatine kinase, 420 ng/μl gp32, 140 ng/μl UvsX, 35 ng/μl UvsY, 2000M dNTPs, 300 nM each oligonucleotide, 35 ng/μl Bsu polymerase, and a nucleic acid-containing sample).

In a transcription mediated amplification (TMA), an RNA polymerase is used to make RNA from a promoter engineered in the primer region, and then a reverse transcriptase synthesizes cDNA from the primer. A third enzyme, e.g., Rnase H can then be used to degrade the RNA target from cDNA without the heat-denatured step. This amplification technique is similar to Self-Sustained Sequence Replication (3SR) and Nucleic Acid Sequence Based Amplification (NASBA), but varies in the enzymes employed. For another example, helicase-dependent amplification (HDA) utilizes a thermostable helicase (Tte-UvrD) rather than heat to unwind dsDNA to create single-strands that are then available for hybridization and extension of primers by polymerase. For yet another example, a loop mediated amplification (LAMP) employs a thermostable polymerase with strand displacement capabilities and a set of four or more specific designed primers. Each primer is designed to have hairpin ends that, once displaced, snap into a hairpin to facilitate self-priming and further polymerase extension. In a LAMP reaction, though the reaction proceeds under isothermal conditions, an initial heat denaturation step is required for double-stranded targets. In addition, amplification yields a ladder pattern of various length products. For yet another example, a strand displacement amplification (SDA) combines the ability of a restriction endonuclease to nick the unmodified strand of its target DNA and an exonuclease-deficient DNA polymerase to extend the 3' end at the nick and displace the downstream DNA strand.

Reporter Oligonucleotide

In certain embodiments, a subject method includes contacting a sample (e.g., a sample comprising a target DNA and a plurality of non-target ssDNAs) with: i) a Type V CRISPR/Cas effector protein (e.g., a Cas12 protein such as Cas12a, Cas12b, Cas12c, Cas12d, Cas12e); ii) a guide RNA (or precursor guide RNA array); and iii) a reporter oligonucleotide that is single stranded and does not hybridize with the spacer sequence of the guide RNA. For example, in certain embodiments, a subject method includes contacting a sample with a labeled single stranded DNA reporter oligonucleotide (ssDNA reporter oligonucleotide) that includes a fluorescence-emitting dye pair; the Type V CRISPR/Cas effector protein (e.g., a Cas12 protein such as Cas12a, Cas12b, Cas12c, Cas12d, Cas12e) cleaves the labeled ssDNA reporter oligonucleotide after it is activated (by binding to the guide RNA in the context of the guide RNA hybridizing to a target DNA); and the detectable signal that is measured is produced by the fluorescence-emitting dye pair. For example, in certain embodiments, a subject method includes contacting a sample with a labeled ssDNA reporter oligonucleotide comprising a fluorescence resonance energy transfer (FRET) pair or a quencher/fluor pair, or both. In certain embodiments, a subject method includes contacting a sample with a labeled ssDNA reporter oligonucleotide comprising a FRET pair. In certain embodiments, a subject method includes contacting a sample with a labeled ssDNA reporter oligonucleotide comprising a fluor/quencher pair.

Fluorescence-emitting dye pairs comprise a FRET pair or a quencher/fluor pair. In both cases of a FRET pair and a quencher/fluor pair, the emission spectrum of one of the dyes overlaps a region of the absorption spectrum of the other dye in the pair. As used herein, the term "fluorescence-emitting dye pair" is a generic term used to encompass both a "fluorescence resonance energy transfer (FRET) pair" and a "quencher/fluor pair," both of which terms are discussed in more detail below. The term "fluorescence-emitting dye pair" is used interchangeably with the phrase "a FRET pair and/or a quencher/fluor pair."

In certain embodiments (e.g., when the ssDNA reporter oligonucleotide includes a FRET pair), the labeled ssDNA reporter oligonucleotide produces an amount of detectable signal prior to being cleaved, and the amount of detectable signal that is measured is reduced when the labeled ssDNA reporter oligonucleotide is cleaved. In certain embodiments, the labeled ssDNA reporter oligonucleotide produces a first detectable signal prior to being cleaved (e.g., from a FRET pair) and a second detectable signal when the labeled ssDNA reporter oligonucleotide is cleaved (e.g., from a quencher/fluor pair). As such, in certain embodiments, the labeled ssDNA reporter oligonucleotide comprises a FRET pair and a quencher/fluor pair.

In certain embodiments, the labeled ssDNA reporter oligonucleotide comprises a FRET pair. FRET is a process by which radiationless transfer of energy occurs from an excited state fluorophore to a second chromophore in close proximity. The range over which the energy transfer can take place is limited to approximately 10 nanometers (100 angstroms), and the efficiency of transfer is extremely sensitive to the separation distance between fluorophores.

Thus, as used herein, the term "FRET" ("fluorescence resonance energy transfer"; also known as "Forster resonance energy transfer") refers to a physical phenomenon involving a donor fluorophore and a matching acceptor fluorophore selected so that the emission spectrum of the donor overlaps the excitation spectrum of the acceptor, and further selected so that when donor and acceptor are in close proximity (usually 10 nm or less) to one another, excitation of the donor will cause excitation of and emission from the acceptor, as some of the energy passes from donor to acceptor via a quantum coupling effect. Thus, a FRET signal serves as a proximity gauge of the donor and acceptor; only when they are in close proximity to one another is a signal generated. The FRET donor moiety (e.g., donor fluorophore) and FRET acceptor moiety (e.g., acceptor fluorophore) are collectively referred to herein as a "FRET pair".

The donor-acceptor pair (a FRET donor moiety and a FRET acceptor moiety) is referred to herein as a "FRET pair" or a "signal FRET pair." Thus, in certain embodiments, a subject labeled ssDNA reporter oligonucleotide includes two signal partners (a signal pair), when one signal partner is a FRET donor moiety and the other signal partner is a FRET acceptor moiety. A subject labeled ssDNA reporter oligonucleotide that includes such a FRET pair (a FRET donor moiety and a FRET acceptor moiety) will thus exhibit a detectable signal (a FRET signal) when the signal partners are in close proximity (e.g., while on the same DNA molecule), but the signal will be reduced (or absent) when the partners are separated (e.g., after cleavage of the DNA molecule by a Type V CRISPR/Cas effector protein (e.g., a Cas12 protein such as Cas12a, Cas12b, Cas12c, Cas12d, Cas12e)).

FRET donor and acceptor moieties (FRET pairs) will be known to one of ordinary skill in the art and any convenient FRET pair (e.g., any convenient donor and acceptor moiety pair) can be used. See: Bajar et al. Sensors (Basel). 2016 Sep. 14; 16(9); and Abraham et al. PLoS One. 2015 Aug. 3; 10(8):e0134436.

In certain embodiments, a detectable signal is produced when the labeled ssDNA reporter oligonucleotide is cleaved (e.g., in certain embodiments, the labeled ssDNA reporter oligonucleotide comprises a quencher/fluor pair). One signal partner of a signal quenching pair produces a detectable signal and the other signal partner is a quencher moiety that quenches the detectable signal of the first signal partner (i.e., the quencher moiety quenches the signal of the signal moiety such that the signal from the signal moiety is reduced (quenched) when the signal partners are in proximity to one another, e.g., when the signal partners of the signal pair are in close proximity).

For example, in certain embodiments, an amount of detectable signal increases when the labeled ssDNA reporter oligonucleotide is cleaved. For example, in certain embodiments, the signal exhibited by one signal partner (a signal moiety) is quenched by the other signal partner (a quencher signal moiety), e.g., when both are present on the same ssDNA molecule prior to cleavage by a Type V CRISPR/Cas effector protein (e.g., a Cas12 protein such as Cas12a, Cas12b, Cas12c, Cas12d, Cas12e). Such a signal pair is referred to herein as a “quencher/fluor pair”, “quenching pair”, or “signal quenching pair.” For example, in certain embodiments, one signal partner (e.g., the first signal partner) is a signal moiety that produces a detectable signal that is quenched by the second signal partner (e.g., a quencher moiety). The signal partners of such a quencher/fluor pair will thus produce a detectable signal when the partners are separated (e.g., after cleavage of the ssDNA reporter oligonucleotide by a Type V CRISPR/Cas effector protein (e.g., a Cas12 protein such as Cas12a, Cas12b, Cas12c, Cas12d, Cas12e)), but the signal will be quenched when the partners are in close proximity (e.g., prior to cleavage of the ssDNA reporter oligonucleotide by a Type V CRISPR/Cas effector protein (e.g., a Cas12 protein such as Cas12a, Cas12b, Cas12c, Cas12d, Cas12e)).

A quencher moiety can quench a signal from the signal moiety (e.g., prior to cleavage of the ssDNA reporter oligonucleotide by a Type V CRISPR/Cas effector protein (e.g., a Cas12 protein such as Cas12a, Cas12b, Cas12c, Cas12d, Cas12e)) to various degrees. In certain embodiments, a quencher moiety quenches the signal from the signal moiety where the signal detected in the presence of the quencher moiety (when the signal partners are in proximity to one another) is 95% or less of the signal detected in the absence of the quencher moiety (when the signal partners are separated). For example, in certain embodiments, the signal detected in the presence of the quencher moiety can be 90% or less, 80% or less, 70% or less, 60% or less, 50% or less, 40% or less, 30% or less, 20% or less, 15% or less, 10% or less, or 5% or less of the signal detected in the absence of the quencher moiety. In certain embodiments, no signal (e.g., above background) is detected in the presence of the quencher moiety.

In certain embodiments, the signal detected in the absence of the quencher moiety (when the signal partners are separated) is at least 1.2 fold greater (e.g., at least 1.3 fold, at least 1.5 fold, at least 1.7 fold, at least 2 fold, at least 2.5 fold, at least 3 fold, at least 3.5 fold, at least 4 fold, at least 5 fold, at least 7 fold, at least 10 fold, at least 20 fold, or at least 50 fold greater) than the signal detected in the presence of the quencher moiety (when the signal partners are in proximity to one another).

In certain embodiments, the signal moiety is a fluorescent label. In some such cases, the quencher moiety quenches the signal (the light signal) from the fluorescent label (e.g., by absorbing energy in the emission spectra of the label). Thus, when the quencher moiety is not in proximity with the signal moiety, the emission (the signal) from the fluorescent label is detectable because the signal is not absorbed by the quencher moiety. Any convenient donor acceptor pair (signal moiety/quencher moiety pair) can be used and many suitable pairs are known in the art.

In certain embodiments, the quencher moiety absorbs energy from the signal moiety (also referred to herein as a “detectable label”) and then emits a signal (e.g., light at a different wavelength). Thus, in certain embodiments, the quencher moiety is itself a signal moiety (e.g., a signal moiety can be 6-carboxyfluorescein while the quencher moiety can be 6-carboxy-tetramethylrhodamine), and in some such cases, the pair could also be a FRET pair. In certain embodiments, a quencher moiety is a dark quencher. A dark quencher can absorb excitation energy and dissipate the energy in a different way (e.g., as heat). Thus, a dark quencher has minimal to no fluorescence of its own (does not emit fluorescence). Examples of dark quenchers are further described in U.S. Pat. Nos. 8,822,673 and 8,586,718; U.S. patent publications 20140378330, 20140349295, and 20140194611; and international patent applications: WO200142505 and WO200186001, all if which are hereby incorporated by reference in their entirety.

Examples of fluorescent labels include, but are not limited to: an Alexa Fluor® dye, an ATTO dye (e.g., ATTO 390, ATTO 425, ATTO 465, ATTO 488, ATTO 495, ATTO 514, ATTO 520, ATTO 532, ATTO Rho6G, ATTO 542, ATTO 550, ATTO 565, ATTO Rho3B, ATTO Rho11, ATTO Rho12, ATTO Thio12, ATTO Rho101, ATTO 590, ATTO 594, ATTO Rho13, ATTO 610, ATTO 620, ATTO Rho14, ATTO 633, ATTO 647, ATTO 647N, ATTO 655, ATTO Oxa12, ATTO 665, ATTO 680, ATTO 700, ATTO 725, ATTO 740), a DyLight dye, a cyanine dye (e.g., Cy2, Cy3, Cy3.5, Cy3b, Cy5, Cy5.5, Cy7, Cy7.5), a FluoProbes dye, a Sulfo Cy dye, a Seta dye, an IRIS Dye, a SeTau dye, an SRfluor dye, a Square dye, fluorescein isothiocyanate (FITC), tetramethylrhodamine (TRITC), Texas Red, Oregon Green, Pacific Blue, Pacific Green, Pacific Orange, quantum dots, and a tethered fluorescent protein.

In certain embodiments, a detectable label is a fluorescent label selected from: an Alexa Fluor® dye, an ATTO dye (e.g., ATTO 390, ATTO 425, ATTO 465, ATTO 488, ATTO 495, ATTO 514, ATTO 520, ATTO 532, ATTO Rho6G, ATTO 542, ATTO 550, ATTO 565, ATTO Rho3B, ATTO Rho11, ATTO Rho12, ATTO Thio12, ATTO Rho101, ATTO 590, ATTO 594, ATTO Rho13, ATTO 610, ATTO 620, ATTO Rho14, ATTO 633, ATTO 647, ATTO 647N, ATTO 655, ATTO Oxa12, ATTO 665, ATTO 680, ATTO 700, ATTO 725, ATTO 740), a DyLight dye, a cyanine dye (e.g., Cy2, Cy3, Cy3.5, Cy3b, Cy5, Cy5.5, Cy7, Cy7.5), a FluoProbes dye, a Sulfo Cy dye, a Seta dye, an IRIS Dye, a SeTau dye, an SRfluor dye, a Square dye, fluorescein (FITC), tetramethylrhodamine (TRITC), Texas Red, Oregon Green, Pacific Blue, Pacific Green, and Pacific Orange.

In certain embodiments, a detectable label is a fluorescent label selected from: an Alexa Fluor® dye, an ATTO dye (e.g., ATTO 390, ATTO 425, ATTO 465, ATTO 488, ATTO 495, ATTO 514, ATTO 520, ATTO 532, ATTO Rho6G, ATTO 542, ATTO 550, ATTO 565, ATTO Rho3B, ATTO Rho11, ATTO Rho12, ATTO Thio12, ATTO Rho101, ATTO 590, ATTO 594, ATTO Rho13, ATTO 610, ATTO 620, ATTO Rho14, ATTO 633, ATTO 647, ATTO 647N, ATTO 655, ATTO Oxa12, ATTO 665, ATTO 680, ATTO 700, ATTO 725, ATTO 740), a DyLight dye, a cyanine dye (e.g., Cy2, Cy3, Cy3.5, Cy3b, Cy5, Cy5.5, Cy7, Cy7.5), a FluoProbes dye, a Sulfo Cy dye, a Seta dye, an IRIS Dye, a SeTau dye, an SRfluor dye, a Square dye, fluorescein (FITC), tetramethylrhodamine (TRITC), Texas Red, Oregon Green, Pacific Blue, Pacific Green, Pacific Orange, a quantum dot, and a tethered fluorescent protein.

Examples of ATTO dyes include, but are not limited to: ATTO 390, ATTO 425, ATTO 465, ATTO 488, ATTO 495, ATTO 514, ATTO 520, ATTO 532, ATTO Rho6G, ATTO 542, ATTO 550, ATTO 565, ATTO Rho3B, ATTO Rho11, ATTO Rho12, ATTO Thio12, ATTO Rho101, ATTO 590, ATTO 594, ATTO Rho13, ATTO 610, ATTO 620, ATTO Rho14, ATTO 633, ATTO 647, ATTO 647N, ATTO 655, ATTO Oxa12, ATTO 665, ATTO 680, ATTO 700, ATTO 725, and ATTO 740.

Examples of AlexaFluor® dyes include, but are not limited to: Alexa Fluor® 350, Alexa Fluor® 405, Alexa Fluor® 430, Alexa Fluor® 488, Alexa Fluor® 500, Alexa Fluor® 514, Alexa Fluor® 532, Alexa Fluor® 546, Alexa Fluor® 555, Alexa Fluor® 568, Alexa Fluor® 594, Alexa Fluor® 610, Alexa Fluor® 633, Alexa Fluor® 635, Alexa Fluor® 647, Alexa Fluor® 660, Alexa Fluor® 680, Alexa Fluor® 700, Alexa Fluor® 750, Alexa Fluor® 790, and the like.

Examples of quencher moieties include, but are not limited to: a dark quencher, a Black Hole Quencher® (BHQ®) (e.g., BHQ-0, BHQ-1, BHQ-2, BHQ-3), a Qxl quencher, an ATTO quencher (e.g., ATTO 540Q, ATTO 580Q, and ATTO 612Q), dimethylaminoazobenzenesulfonic acid (Dabsyl), Iowa Black RQ, Iowa Black FQ, IRDye QC-1, a QSY dye (e.g., QSY 7, QSY 9, QSY 21), AbsoluteQuencher, Eclipse, and metal clusters such as gold nanoparticles, and the like.

In certain embodiments, a quencher moiety is selected from: a dark quencher, a Black Hole Quencher® (BHQ®) (e.g., BHQ-0, BHQ-1, BHQ-2, BHQ-3), a Qxl quencher, an ATTO quencher (e.g., ATTO 540Q, ATTO 580Q, and ATTO 612Q), dimethylaminoazobenzenesulfonic acid (Dabsyl), Iowa Black RQ, Iowa Black FQ, IRDye QC-1, a QSY dye (e.g., QSY 7, QSY 9, QSY 21), AbsoluteQuencher, Eclipse, and a metal cluster.

Examples of an ATTO quencher include, but are not limited to: ATTO 540Q, ATTO 580Q, and ATTO 612Q. Examples of a Black Hole Quencher® (BHQ®) include, but are not limited to: BHQ-0 (493 nm), BHQ-1 (534 nm), BHQ-2 (579 nm) and BHQ-3 (672 nm).

For examples of some detectable labels (e.g., fluorescent dyes) and/or quencher moieties, see, e.g., Bao et al., Annu Rev Biomed Eng. 2009; 11:25-47; as well as U.S. Pat. Nos. 8,822,673 and 8,586,718; U.S. patent publications 20140378330, 20140349295, 20140194611, 20130323851, 20130224871, 20110223677, 20110190486, 20110172420, 20060179585 and 20030003486; and international patent applications: WO200142505 and WO200186001, all of which are hereby incorporated by reference in their entirety.

In certain embodiments, cleavage of a labeled ssDNA reporter oligonucleotide can be detected by measuring a colorimetric read-out. For example, the liberation of a fluorophore (e.g., liberation from a FRET pair, liberation from a quencher/fluor pair, and the like) can result in a wavelength shift (and thus color shift) of a detectable signal. Thus, in certain embodiments, cleavage of a subject labeled ssDNA reporter oligonucleotide can be detected by a color-shift. Such a shift can be expressed as a loss of an amount of signal of one color (wavelength), a gain in the amount of another color, a change in the ration of one color to another, and the like.

Type V CRISPR/Cas Effector Proteins

Type V CRISPR/Cas effector proteins are a subtype of Class 2 CRISPR/Cas effector proteins. For examples of type V CRISPR/Cas systems and their effector proteins (e.g., Cas12 family proteins such as Cas12a), see, e.g., Shmakov et al., Nat Rev Microbiol. 2017 March; 15(3):169-182: "Diversity and evolution of class 2 CRISPR-Cas systems." Examples include, but are not limited to: Cas12 family (Cas12a, Cas12b, Cas12c), C2c4, C2c8, C2c5, C2c10, and C2c9; as well as CasX (Cas12e) and CasY (Cas12d). Also see, e.g., Koonin et al., Curr Opin Microbiol. 2017 June; 37:67-78: "Diversity, classification and evolution of CRISPR-Cas systems."

As such, in certain embodiments, a subject type V CRISPR/Cas effector protein is a Cas12 protein (e.g., Cas12a, Cas12b, Cas12c). In certain embodiments, a subject type V CRISPR/Cas effector protein is a Cas12 protein such as Cas12a, Cas12b, Cas12c, Cas12d, Cas12e, Cas12d, or Cas12e. In certain embodiments, a subject type V CRISPR/Cas effector protein is a Cas12a protein. In certain embodiments, a subject type V CRISPR/Cas effector protein is a Cas12b protein. In certain embodiments, a subject type V CRISPR/Cas effector protein is a Cas12c protein. In certain embodiments, a subject type V CRISPR/Cas effector protein is a Cas12d protein. In certain embodiments, a subject type V CRISPR/Cas effector protein is a Cas12e protein. In certain embodiments, a subject type V CRISPR/Cas effector protein is protein selected from: Cas12 (e.g., Cas12a, Cas12b, Cas12c, Cas12d, Cas12e), C2c4, C2c8, C2c5, C2c10, and C2c9. In certain embodiments, a subject type V CRISPR/Cas effector protein is protein selected from: C2c4, C2c8, C2c5, C2c10, and C2c9. In certain embodiments, a subject type V CRISPR/Cas effector protein is protein selected from: C2c4, C2c8, and C2c5. In certain embodiments, a subject type V CRISPR/Cas effector protein is protein selected from: C2c10 and C2c9.

In certain embodiments, the subject type V CRISPR/Cas effector protein is a naturally-occurring protein (e.g., naturally occurs in prokaryotic cells). In other cases, the Type V CRISPR/Cas effector protein is not a naturally-occurring polypeptide (e.g., the effector protein is a variant protein, a chimeric protein, includes a fusion partner, and the like). Any Type V CRISPR/Cas effector protein can be suitable for the compositions (e.g., nucleic acids, kits, etc.) and methods of the present disclosure (e.g., as long as the Type V CRISPR/Cas effector protein forms a complex with a guide RNA and exhibits ssDNA cleavage activity of non-target ssDNAs once it is activated (by hybridization of and associated guide RNA to its target DNA).

In certain embodiments, a type V CRISPR/Cas effector protein comprises an amino acid sequence having 80% or more sequence identity (e.g., 85% or more, 90% or more, 95% or more, 97% or more, 98% or more, 99% or more, or 100% sequence identity) with a Cas12a protein. For example, in certain embodiments, a type V CRISPR/Cas effector protein comprises an amino acid sequence having 90% or more sequence identity (e.g., 95% or more, 97% or more, 98% or more, 99% or more, or 100% sequence identity) with a Cas12a protein (e.g., the Cas12a protein set forth in SEQ ID NO: 21). In certain embodiments, a suitable type V CRISPR/Cas effector protein comprises an amino acid sequence having 80% or more sequence identity (e.g., 85% or more, 90% or more, 95% or more, 97% or more, 98% or more, 99% or more, or 100% sequence identity) with the *Lachnospiraceae bacterium* ND2006 Cas12a protein amino acid sequence set forth in SEQ ID NO: 21.

In certain embodiments, a subject type V CRISPR/Cas effector protein (e.g., a Cas12 protein such as Cas12a, Cas12b, Cas12c, Cas12d, Cas12e) is fused to (conjugated to) a heterologous polypeptide. In certain embodiments, a heterologous polypeptide (a fusion partner) provides for subcellular localization, i.e., the heterologous polypeptide contains a subcellular localization sequence (e.g., a nuclear localization signal (NLS) for targeting to the nucleus, a sequence to keep the fusion protein out of the nucleus, e.g., a nuclear export sequence (NES), a sequence to keep the fusion protein retained in the cytoplasm, a mitochondrial localization signal for targeting to the mitochondria, a chloroplast localization signal for targeting to a chloroplast, an ER retention signal, and the like). In certain embodiments, the heterologous polypeptide can provide a tag (i.e., the heterologous polypeptide is a detectable label) for ease of tracking and/or purification (e.g., a fluorescent protein, e.g., green fluorescent protein (GFP), YFP, RFP, CFP, mCherry, tdTomato, and the like; a histidine tag, e.g., a 6×His tag; a hemagglutinin (HA) tag; a FLAG tag; a Myc tag; and the like).

In certain embodiments, a type V CRISPR/Cas effector protein (e.g., a Cas12 protein such as Cas12a, Cas12b, Cas12c, Cas12d, Cas12e) includes (is fused to) a nuclear localization signal (NLS) (e.g., in certain embodiments, 2 or more, 3 or more, 4 or more, or 5 or more NLSs). Thus, in certain embodiments, a type V CRISPR/Cas effector protein includes one or more NLSs (e.g., 2 or more, 3 or more, 4 or more, or 5 or more NLSs). In certain embodiments, one or more NLSs (2 or more, 3 or more, 4 or more, or 5 or more NLSs) are positioned at or near (e.g., within 50 amino acids of) the N-terminus and/or the C-terminus. In certain embodiments, one or more NLSs (2 or more, 3 or more, 4 or more, or 5 or more NLSs) are positioned at or near (e.g., within 50 amino acids of) the N-terminus. In certain embodiments, one or more NLSs (2 or more, 3 or more, 4 or more, or 5 or more NLSs) are positioned at or near (e.g., within 50 amino acids of) the C-terminus. In certain embodiments, one or more NLSs (3 or more, 4 or more, or 5 or more NLSs) are positioned at or near (e.g., within 50 amino acids of) both the N-terminus and the C-terminus. In certain embodiments, an NLS is positioned at the N-terminus and an NLS is positioned at the C-terminus.

In certain embodiments, a type V CRISPR/Cas effector protein (e.g., a Cas12 protein such as Cas12a, Cas12b, Cas12c, Cas12d, Cas12e) includes (is fused to) between 1 and 10 NLSs (e.g., 1-9, 1-8, 1-7, 1-6, 1-5, 2-10, 2-9, 2-8, 2-7, 2-6, or 2-5 NLSs). In certain embodiments, a type V CRISPR/Cas effector protein includes (is fused to) between 2 and 5 NLSs (e.g., 2-4, or 2-3 NLSs). In general, NLS (or multiple NLSs) are of sufficient strength to drive accumulation of the protein in a detectable amount in the nucleus of a plant cell. Detection of accumulation in the nucleus may be performed by any suitable technique.

Protospacer Adjacent Motif (PAM)

A Type V CRISPR/Cas effector protein binds to target DNA at a target sequence defined by the region of complementarity between the DNA-targeting RNA and the target DNA. As is the case for many CRISPR/Cas endonucleases, site-specific binding (and/or cleavage) of a double stranded target DNA occurs at locations determined by both (i) base-pairing complementarity between the guide RNA and the target DNA; and (ii) a short motif [referred to as the protospacer adjacent motif (PAM)] in the target DNA.

In certain embodiments, the PAM for a Type V CRISPR/Cas effector protein is immediately 5' of the target sequence (e.g., of the non-complementary strand of the target DNA—the complementary strand hybridizes to the spacer sequence of the guide RNA while the non-complementary strand does not directly hybridize with the guide RNA and is the reverse complement of the non-complementary strand). In certain embodiments (e.g., when Cas12a or Cas12b as described herein is used), the PAM sequence is 5'-TTN-3'. In certain embodiments, the PAM sequence is 5'-TTTN-3'.

In certain embodiments, different Type V CRISPR/Cas effector proteins (i.e., Type V CRISPR/Cas effector proteins from various species) may be advantageous to use in the various provided methods in order to capitalize on a desired feature (e.g., specific enzymatic characteristics of different Type V CRISPR/Cas effector proteins). Type V CRISPR/Cas effector proteins from different species may require different PAM sequences in the target DNA. Thus, for a particular Type V CRISPR/Cas effector protein of choice, the PAM sequence requirement may be different than the 5'-TTN-3' or 5'-TTTN-3' sequence described above. Various methods (including in silico and/or wet lab methods) for identification of the appropriate PAM sequence are known in the art and are routine, and any convenient method can be used.

Guide RNA

A nucleic acid molecule (e.g., a natural crRNA) that binds to a type V CRISPR/Cas effector protein (e.g., a Cas12 protein such as Cas12a, Cas12b, Cas12c, Cas12d, Cas12e), forming a ribonucleoprotein complex (RNP), and targets the complex to a specific target sequence within a target DNA is referred to herein as a "guide RNA." It is to be understood that in certain embodiments, a hybrid DNA/RNA can be made such that a guide RNA includes DNA bases in addition to RNA bases—but the term "guide RNA" is still used herein to encompass such hybrid molecules. A subject guide RNA includes a spacer sequence (that hybridizes to target sequence of a target DNA) and a constant region (e.g., a region that is adjacent to the spacer sequence and binds to the type V CRISPR/Cas effector protein). A "constant region" can also be referred to herein as a "protein-binding segment." In certain embodiments, e.g., for Cas12a, the constant region is 5' of the spacer sequence.

Spacer Sequence

The spacer sequence has complementarity with (hybridizes to) a target sequence of the target DNA. In certain embodiments, the spacer sequence is 15-28 nucleotides (nt) in length (e.g., 15-26, 15-24, 15-22, 15-20, 15-18, 16-28, 16-26, 16-24, 16-22, 16-20, 16-18, 17-26, 17-24, 17-22, 17-20, 17-18, 18-26, 18-24, or 18-22 nt in length). In certain embodiments, the spacer sequence is 18-24 nucleotides (nt) in length. In certain embodiments, the spacer sequence is at least 15 nt long (e.g., at least 16, 18, 20, or 22 nt long). In certain embodiments, the spacer sequence is at least 17 nt long. In certain embodiments, the spacer sequence is at least 18 nt long. In certain embodiments, the spacer sequence is at least 20 nt long.

In certain embodiments, the spacer sequence has 80% or more (e.g., 85% or more, 90% or more, 95% or more, or 100% complementarity) with the target sequence of the target DNA. In certain embodiments, the spacer sequence is 100% complementary to the target sequence of the target DNA. In certain embodiments, the target DNA includes at least 15 nucleotides (nt) of complementarity with the spacer sequence of the guide RNA.

Constant Region

An example of a constant region for guide RNAs that can be used with a type V CRISPR/Cas effector protein (e.g., a Cas12 protein such as Cas12a, Cas12b, Cas12c, Cas12d, Cas12e) is set forth in SEQ ID NO: 18. In certain embodiments, a subject guide RNA includes a nucleotide sequence having 80% or more identity (e.g., 85% or more, 90% or more, 95% or more, 98% or more, 99% or more, or 100% identity) with the sequence set forth in SEQ ID NO: 18. In certain embodiments, a subject guide RNA comprises the sequence set forth in SEQ ID NO: 18.

In certain embodiments, the guide RNA includes a double stranded RNA duplex (dsRNA duplex). In certain embodiments, a guide RNA includes a dsRNA duplex with a length of from 2 to 12 bp (e.g., from 2 to 10 bp, 2 to 8 bp, 2 to 6 bp, 2 to 5 bp, 2 to 4 bp, 3 to 12 bp, 3 to 10 bp, 3 to 8 bp, 3 to 6 bp, 3 to 5 bp, 3 to 4 bp, 4 to 12 bp, 4 to 10 bp, 4 to 8 bp, 4 to 6 bp, or 4 to 5 bp). In certain embodiments, a guide RNA includes a dsRNA duplex that is 2 or more bp in length (e.g., 3 or more, 4 or more, 5 or more, 6 or more, or 7 or more bp in length). In certain embodiments, a guide RNA includes a dsRNA duplex that is longer than the dsRNA duplex of a corresponding wild type guide RNA. In certain embodiments, a guide RNA includes a dsRNA duplex that is shorter than the dsRNA duplex of a corresponding wild type guide RNA.

In certain embodiments, the constant region of a guide RNA is 15 or more nucleotides (nt) in length (e.g., 18 or more, 20 or more, 21 or more, 22 or more, 23 or more, 24 or more, 25 or more, 26 or more, 27 or more, 28 or more, 29 or more, 30 or more, 31 or more nt, 32 or more, 33 or more, 34 or more, or 35 or more nt in length). In certain embodiments, the constant region of a guide RNA is 18 or more nt in length.

In certain embodiments, the constant region of a guide RNA has a length in a range of from 12 to 100 nt (e.g., from 12 to 90, 12 to 80, 12 to 70, 12 to 60, 12 to 50, 12 to 40, 15 to 100, 15 to 90, 15 to 80, 15 to 70, 15 to 60, 15 to 50, 15 to 40, 20 to 100, 20 to 90, 20 to 80, 20 to 70, 20 to 60, 20 to 50, 20 to 40, 25 to 100, 25 to 90, 25 to 80, 25 to 70, 25 to 60, 25 to 50, 25 to 40, 28 to 100, 28 to 90, 28 to 80, 28 to 70, 28 to 60, 28 to 50, 28 to 40, 29 to 100, 29 to 90, 29 to 80, 29 to 70, 29 to 60, 29 to 50, or 29 to 40 nt). In certain embodiments, the constant region of a guide RNA has a length in a range of from 28 to 100 nt. In certain embodiments, the region of a guide RNA that is 5' of the spacer sequence has a length in a range of from 28 to 40 nt.

In certain embodiments, the constant region of a guide RNA is truncated relative to (shorter than) the corresponding region of a corresponding wild type guide RNA. In certain embodiments, the constant region of a guide RNA is extended relative to (longer than) the corresponding region of a corresponding wild type guide RNA. In certain embodiments, a subject guide RNA is 30 or more nucleotides (nt) in length (e.g., 34 or more, 40 or more, 45 or more, 50 or more, 55 or more, 60 or more, 65 or more, 70 or more, or 80 or more nt in length). In certain embodiments, the guide RNA is 35 or more nt in length.

Precursor Guide RNA Array

A Type V CRISPR/Cas effector protein (e.g., a Cas12 protein such as Cas12a, Cas12b, Cas12c, Cas12d, Cas12e) can cleave a precursor guide RNA into a mature guide RNA, e.g., by endoribonucleolytic cleavage of the precursor. A Type V CRISPR/Cas effector protein (e.g., a Cas12 protein such as Cas12a, Cas12b, Cas12c, Cas12d, Cas12e) can cleave a precursor guide RNA array (that includes more than one guide RNA arrayed in tandem) into two or more individual guide RNAs. Thus, in certain embodiments, a precursor guide RNA array comprises two or more (e.g., 3 or more, 4 or more, 5 or more, 2, 3, 4, or 5) guide RNAs (e.g., arrayed in tandem as precursor molecules). In other words, in certain embodiments, two or more guide RNAs can be present on an array (a precursor guide RNA array). A Type V CRISPR/Cas effector protein (e.g., a Cas12 protein such as Cas12a, Cas12b, Cas12c, Cas12d, Cas12e) can cleave the precursor guide RNA array into individual guide RNAs.

In certain embodiments, a subject guide RNA array includes 2 or more guide RNAs (e.g., 3 or more, 4 or more, 5 or more, 6 or more, or 7 or more, guide RNAs). The guide RNAs of a given array can target (i.e., can include spacer sequences that hybridize to) different target sites of the same target DNA (e.g., which can increase sensitivity of detection) and/or can target different target DNA molecules (e.g., different strains of a particular bacterial plant pathogen), and such could be used for example to detect multiple strains of a bacterial plant pathogen. In certain embodiments, each guide RNA of a precursor guide RNA array has a different spacer sequence. In certain embodiments, two or more guide RNAs of a precursor guide RNA array have the same spacer sequence.

In certain embodiments, the precursor guide RNA array comprises two or more guide RNAs that target different target sites within the same target DNA molecule. For example, such a scenario can, in certain embodiments, increase sensitivity of detection by activating Type V CRISPR/Cas effector protein (e.g., a Cas12 protein such as Cas12a, Cas12b, Cas12c, Cas12d, Cas12e) when either one hybridizes to the target DNA molecule. As such, in certain embodiments, as subject composition (e.g., kit) or method includes two or more guide RNAs (in the context of a precursor guide RNA array, or not in the context of a precursor guide RNA array, e.g., the guide RNAs can be mature guide RNAs).

In certain embodiments, the precursor guide RNA array comprises two or more guide RNAs that target different target DNA molecules. For example, such a scenario can result in a positive signal when any one of a family of potential target DNAs is present. Such an array could be used for targeting a family of transcripts, e.g., based on variation such as single nucleotide polymorphisms (SNPs) (e.g., for diagnostic purposes). Such could also be useful for detecting whether any one of a number of different species, strains, isolates, or variants of a bacterial plant pathogen is present (e.g., different species, strains, isolates, or variants of *Candidatus Liberibacter*; different species, strains, isolates, or variants of *Candidatus Phytoplasma*; etc.). As such, in certain embodiments, a subject composition (e.g., kit) or method includes two or more guide RNAs (in the context of a precursor guide RNA array, or not in the context of a precursor guide RNA array, e.g., the guide RNAs can be mature guide RNAs).

Nucleic Acid Modifications

In certain embodiments, a labeled ssDNA reporter oligonucleotide (and/or a guide RNA) comprises one or more modifications, e.g., a base modification, a backbone modification, a sugar modification, etc., to provide the nucleic acid with a new or enhanced feature (e.g., improved stability). As is known in the art, a nucleoside is a base-sugar combination. The base portion of the nucleoside is normally a heterocyclic base. The two most common classes of such heterocyclic bases are the purines and the pyrimidines. Nucleotides are nucleosides that further include a phosphate group covalently linked to the sugar portion of the nucleoside. For those nucleosides that include a pentofuranosyl sugar, the phosphate group can be linked to the 2', the 3', or the 5' hydroxyl moiety of the sugar. In forming oligonucleotides, the phosphate groups covalently link adjacent nucleosides to one another to form a linear polymeric compound. In turn, the respective ends of this linear polymeric compound can be further joined to form a circular compound, however, linear compounds are generally suitable. In addition, linear compounds may have internal nucleotide base complementarity and may therefore fold in a manner as to produce a fully or partially double-stranded compound. Within oligonucleotides, the phosphate groups are commonly referred to as forming the internucleoside backbone of the oligonucleotide. The normal linkage or backbone of RNA and DNA is a 3' to 5' phosphodiester linkage.

Modified Backbones and Modified Internucleoside Linkages

Examples of suitable modifications include modified nucleic acid backbones and non-natural internucleoside linkages. Nucleic acids having modified backbones include those that retain a phosphorus atom in the backbone and those that do not have a phosphorus atom in the backbone.

Suitable modified oligonucleotide backbones containing a phosphorus atom therein include, for example, phosphorothioates, chiral phosphorothioates, phosphorodithioates, phosphotriesters, aminoalkylphosphotriesters, methyl and other alkyl phosphonates including 3'-alkylene phosphonates, 5'-alkylene phosphonates and chiral phosphonates, phosphinates, phosphoramidates including 3'-amino phosphoramidate and aminoalkylphosphoramidates, phosphorodiamidates, thionophosphoramidates, thionoalkylphosphonates, thionoalkylphosphotriesters, selenophosphates and boranophosphates having normal 3'-5' linkages, 2'-5' linked analogs of these, and those having inverted polarity wherein one or more internucleotide linkages is a 3' to 3', 5' to 5' or 2' to 2' linkage. Suitable oligonucleotides having inverted polarity comprise a single 3' to 3' linkage at the 3'-most internucleotide linkage i.e. a single inverted nucleoside residue which may be a basic (the nucleobase is missing or has a hydroxyl group in place thereof). Various salts (such as, for example, potassium or sodium), mixed salts and free acid forms are also included.

In certain embodiments, a labeled ssDNA reporter oligonucleotide (and/or a guide RNA) comprises one or more phosphorothioate and/or heteroatom internucleoside linkages, in particular —$CH_2$—NH—O—$CH_2$—, —$CH_2$—N($CH_3$)—O—$CH_2$— (known as a methylene (methylimino) or MMI backbone), —$CH_2$—O—N($CH_3$)—$CH_2$—, —$CH_2$—N($CH_3$)—N($CH_3$)—$CH_2$— and —O—N($CH_3$)—$CH_2$—$CH_2$— (wherein the native phosphodiester internucleotide linkage is represented as —O—P(═O)(OH)—O—$CH_2$—). MMI type internucleoside linkages are disclosed in the above referenced U.S. Pat. No. 5,489,677. Suitable amide internucleoside linkages are disclosed in t U.S. Pat. No. 5,602,240.

Also suitable are nucleic acids having morpholino backbone structures as described in, e.g., U.S. Pat. No. 5,034,506. For example, in certain embodiments, a labeled ssDNA reporter oligonucleotide (and/or a guide RNA) comprises a 6-membered morpholino ring in place of a ribose ring. In certain embodiments, a phosphorodiamidate or other non-phosphodiester internucleoside linkage replaces a phosphodiester linkage.

Suitable modified polynucleotide backbones that do not include a phosphorus atom therein have backbones that are formed by short chain alkyl or cycloalkyl internucleoside linkages, mixed heteroatom and alkyl or cycloalkyl internucleoside linkages, or one or more short chain heteroatomic or heterocyclic internucleoside linkages. These include those having morpholino linkages (formed in part from the sugar portion of a nucleoside); siloxane backbones; sulfide, sulfoxide and sulfone backbones; formacetyl and thioformacetyl backbones; methylene formacetyl and thioformacetyl backbones; riboacetyl backbones; alkene containing backbones; sulfamate backbones; methyleneimino and methylenehydrazino backbones; sulfonate and sulfonamide backbones; amide backbones; and others having mixed N, O, S and $CH_2$ component parts.

Mimetics

A labeled ssDNA reporter oligonucleotide (and/or a guide RNA) can be a nucleic acid mimetic. The term "mimetic" as it is applied to polynucleotides is intended to include polynucleotides wherein only the furanose ring or both the furanose ring and the internucleotide linkage are replaced with non-furanose groups, replacement of only the furanose ring is also referred to in the art as being a sugar surrogate. The heterocyclic base moiety or a modified heterocyclic base moiety is maintained for hybridization with an appropriate target nucleic acid. One such nucleic acid, a polynucleotide mimetic that has been shown to have excellent hybridization properties, is referred to as a peptide nucleic acid (PNA). In PNA, the sugar-backbone of a polynucleotide is replaced with an amide containing backbone, in particular an aminoethylglycine backbone. The nucleotides are retained and are bound directly or indirectly to aza nitrogen atoms of the amide portion of the backbone. Representative U.S. patents that describe the preparation of PNA compounds include, but are not limited to: U.S. Pat. Nos. 5,539,082; 5,714,331; and 5,719,262.

Another class of polynucleotide mimetic that has been studied is based on linked morpholino units (morpholino nucleic acid) having heterocyclic bases attached to the morpholino ring. A number of linking groups have been reported that link the morpholino monomeric units in a morpholino nucleic acid. One class of linking groups has been selected to give a non-ionic oligomeric compound. The non-ionic morpholino-based oligomeric compounds are less likely to have undesired interactions with cellular proteins. Morpholino-based polynucleotides are non-ionic mimics of oligonucleotides which are less likely to form undesired interactions with cellular proteins (Dwaine A. Braasch and David R. Corey, Biochemistry, 2002, 41(14), 4503-4510). Morpholino-based polynucleotides are disclosed in U.S. Pat. No. 5,034,506. A variety of compounds within the morpholino class of polynucleotides have been prepared, having a variety of different linking groups joining the monomeric subunits.

A further class of polynucleotide mimetic is referred to as cyclohexenyl nucleic acids (CeNA). The furanose ring normally present in a DNA/RNA molecule is replaced with a cyclohexenyl ring. CeNA DMT protected phosphoramidite monomers have been prepared and used for oligomeric compound synthesis following classical phosphoramidite chemistry. Fully modified CeNA oligomeric compounds and oligonucleotides having specific positions modified with CeNA have been prepared and studied (see Wang et al., J. Am. Chem. Soc., 2000, 122, 8595-8602). In general, the incorporation of CeNA monomers into a DNA chain increases stability of a DNA/RNA hybrid. CeNA oligoadenylates formed complexes with RNA and DNA complements with similar stability to the native complexes. The study of incorporating CeNA structures into natural nucleic acid structures was shown by NMR and circular dichroism to proceed with easy conformational adaptation.

A further modification includes Locked Nucleic Acids (LNAs) in which the 2'-hydroxyl group is linked to the 4' carbon atom of the sugar ring thereby forming a 2'-C,4'-C-oxymethylene linkage thereby forming a bicyclic sugar moiety. The linkage can be a methylene (—$CH_2$—), group bridging the 2' oxygen atom and the 4' carbon atom wherein n is 1 or 2 (Singh et al., Chem. Commun., 1998, 4, 455-456). LNA and LNA analogs display very high duplex thermal stabilities with complementary DNA and RNA (Tm=+3 to +10° C.), stability towards 3'-exonucleolytic degradation and good solubility properties. Potent and nontoxic antisense oligonucleotides containing LNAs have been described (Wahlestedt et al., Proc. Natl. Acad. Sci. U.S.A., 2000, 97, 5633-5638).

The synthesis and preparation of the LNA monomers adenine, cytosine, guanine, 5-methyl-cytosine, thymine and uracil, along with their oligomerization, and nucleic acid recognition properties have been described (Koshkin et al., Tetrahedron, 1998, 54, 3607-3630). LNAs and preparation thereof are also described in WO 98/39352 and WO 99/14226.

Modified Sugar Moieties

A labeled ssDNA reporter oligonucleotide (and/or a guide RNA) can also include one or more substituted sugar moieties. Suitable polynucleotides comprise a sugar substituent group selected from: OH; F; O-, S-, or N-alkyl; O-, S-, or N-alkenyl; O-, S- or N-alkynyl; or O-alkyl-O-alkyl, wherein the alkyl, alkenyl and alkynyl may be substituted or unsubstituted C.sub.1 to $C_{10}$ alkyl or $C_2$ to $C_{10}$ alkenyl and alkynyl. Particularly suitable are $O((CH_2)_nO)_mCH_3$, $O(CH_2)_n$ $OCH_3$, $O(CH_2)_nNH_2$, $O(CH_2)_nCH_3$, $O(CH_2)_n$ $ONH_2$, and $O(CH_2)_nON((CH_2)_nCH_3)_2$, where n and m are from 1 to about 10. Other suitable polynucleotides comprise a sugar substituent group selected from: $C_1$ to $C_{10}$ lower alkyl, substituted lower alkyl, alkenyl, alkynyl, alkaryl, aralkyl, O-alkaryl or O-aralkyl, SH, $SCH_3$, OCN, Cl, Br, CN, $CF_3$, $OCF_3$, $SOCH_3$, $SO_2CH_3$, $ONO_2$, $NO_2$, $N_3$, $NH_2$, heterocycloalkyl, heterocycloalkaryl, aminoalkylamino, poly alkylamino, substituted silyl, an RNA cleaving group, a reporter group, an intercalator, a group for improving the pharmacokinetic properties of an oligonucleotide, or a group for improving the pharmacodynamic properties of an oligonucleotide, and other substituents having similar properties. A suitable modification includes 2'-methoxyethoxy (2'-O—$CH_2CH_2OCH_3$, also known as 2'-O-(2-methoxyethyl) or 2'-MOE) (Martin et al., Helv. Chim. Acta, 1995, 78, 486-504) i.e., an alkoxyalkoxy group. A further suitable modification includes 2'-dimethylaminooxyethoxy, i.e., a $O(CH_2)_{20}N(CH_3)_2$ group, also known as 2'-DMAOE, as described in examples hereinbelow, and 2'-dimethylaminoethoxyethoxy (also known in the art as 2'-O-dimethyl-amino-ethoxy-ethyl or 2'-DMAEOE), i.e., 2'-O—$CH_2$—O—$CH_2$—$N(CH_3)_2$.

Other suitable sugar substituent groups include methoxy (—O—$CH_3$), aminopropoxy $CH_2CH_2CH_2NH_2$), allyl (—$CH_2$—CH═$CH_2$), —O-allyl $CH_2$—CH═$CH_2$) and fluoro (F). 2'-sugar substituent groups may be in the arabino (up) position or ribo (down) position. A suitable 2'-arabino modification is 2'-F Similar modifications may also be made at other positions on the oligomeric compound, particularly the 3' position of the sugar on the 3' terminal nucleoside or in 2'-5' linked oligonucleotides and the 5' position of 5' terminal nucleotide. Oligomeric compounds may also have sugar mimetics such as cyclobutyl moieties in place of the pentofuranosyl sugar.

Base Modifications and Substitutions

A labeled ssDNA reporter oligonucleotide (and/or a guide RNA) may also include nucleobase (often referred to in the art simply as "base") modifications or substitutions. As used herein, "unmodified" or "natural" nucleobases include the purine bases adenine (A) and guanine (G), and the pyrimidine bases thymine (T), cytosine (C) and uracil (U). Modified nucleobases include other synthetic and natural nucleobases such as 5-methylcytosine (5-me-C), 5-hydroxymethyl cytosine, xanthine, hypoxanthine, 2-aminoadenine, 6-methyl and other alkyl derivatives of adenine and guanine, 2-propyl and other alkyl derivatives of adenine and guanine, 2-thiouracil, 2-thiothymine and 2-thiocytosine, 5-halouracil and cytosine, 5-propynyl (—C═C—$CH_3$) uracil and cytosine and other alkynyl derivatives of pyrimidine bases, 6-azo uracil, cytosine and thymine, 5-uracil (pseudouracil), 4-thiouracil, 8-halo, 8-amino, 8-thiol, 8-thioalkyl, 8-hydroxyl and other 8-substituted adenines and guanines, 5-halo particularly 5-bromo, 5-trifluoromethyl and other 5-substituted uracils and cytosines, 7-methylguanine and 7-methyladenine, 2-F-adenine, 2-amino-adenine, 8-azaguanine and 8-azaadenine, 7-deazaguanine and 7-deazaadenine and 3-deazaguanine and 3-deazaadenine. Further modified nucleobases include tricyclic pyrimidines such as phenoxazine cytidine(1H-pyrimido(5,4-b)(1,4)benzoxazin-2(3H)-one), phenothiazine cytidine (1H-pyrimido(5,4-b)(1,4)benzothiazin-2(3H)-one), G-clamps such as a substituted phenoxazine cytidine (e.g. 9-(2-aminoethoxy)-H-pyrimido(5,4-(b) (1,4)benzoxazin-2(3H)-one), carbazole cytidine (2H-pyrimido(4,5-b)indol-2-one), pyridoindole cytidine (H-pyrido(3',2':4,5)pyrrolo(2,3-d)pyrimidin-2-one).

Heterocyclic base moieties may also include those in which the purine or pyrimidine base is replaced with other heterocycles, for example 7-deaza-adenine, 7-deazaguanosine, 2-aminopyridine and 2-pyridone. Further nucleobases include those disclosed in U.S. Pat. No. 3,687,808, those disclosed in The Concise Encyclopedia Of Polymer Science And Engineering, pages 858-859, Kroschwitz, J. I., ed. John Wiley & Sons, 1990, those disclosed by Englisch et al., Angewandte Chemie, International Edition, 1991, 30, 613, and those disclosed by Sanghvi, Y. S., Chapter 15, Antisense Research and Applications, pages 289-302, Crooke, S. T. and Lebleu, B., ed., CRC Press, 1993. Certain nucleobases are useful for increasing the binding affinity of an oligomeric compound. These include 5-substituted pyrimidines, 6-azapyrimidines and N-2, N-6 and 0-6 substituted purines, including 2-aminopropyladenine, 5-propynyluracil and 5-propynylcytosine. 5-methylcytosine substitutions have been shown to increase nucleic acid duplex stability by 0.6-1.2° C. (Sanghvi et al., eds., Antisense Research and Applications, CRC Press, Boca Raton, 1993, pp. 276-278) and are suitable base substitutions, e.g., when combined with 2'-O-methoxyethyl sugar modifications.

Introducing Components into a Cell

Methods of introducing a nucleic acid and/or protein into a host cell are known in the art, and any convenient method can be used to introduce a subject nucleic acid (e.g., an expression construct/vector) into a target cell (e.g., a plant cell). Suitable methods include, but are not limited to, particle bombardment, *Agrobacterium* transformation, and topical applications.

A guide RNA can be introduced, e.g., as a DNA molecule encoding the guide RNA, or can be provided directly as an RNA molecule (or a hybrid molecule when applicable). The guide RNA can be introduced indirectly into a cell by introducing a recombinant DNA molecule (via methods such as, but not limited to, particle bombardment or *Agrobacterium* transformation) comprising a heterologous nucleic acid fragment encoding the guide RNA operably linked to a specific promoter that can transcribe the guide RNA in the cell. The specific promoter can be, but is not limited to, an RNA polymerase III promoter, which allows for transcription of RNA with precisely defined, unmodified, 5'- and 3'-ends (DiCarlo et al., Nucleic Acids Res. 41: 4336-4343; Ma et al., Mol. Ther. Nucleic Acids 3:e161) as described in WO2016025131, published on Feb. 18, 2016, incorporated herein in its entirety by reference.

The type V CRISPR/Cas effector protein can be provided as a protein or as a guided polynucleotide complex directly to a cell or indirectly via nucleic acid (e.g., an expression construct/vector). The type V CRISPR/Cas effector protein can be introduced into a cell transiently or can be incorporated into the genome of the host cell using any method known in the art. In certain embodiments, a type V CRISPR/Cas effector protein is provided as a nucleic acid (e.g., an mRNA, a DNA, a plasmid, an expression vector, a viral vector, etc.) that encodes the protein. In certain embodiments, the type V CRISPR/Cas effector protein is provided directly as a protein (e.g., without an associated guide RNA or with an associate guide RNA, i.e., as a ribonucleoprotein complex-RNP). Like a guide RNA, a type V CRISPR/Cas effector protein can be introduced into a cell (provided to the cell) by any convenient method; such methods are known to those of ordinary skill in the art.

Uptake of the type V CRISPR/Cas effector protein and/or the guided polynucleotide into the cell can be facilitated with a Cell Penetrating Peptide (CPP) as described in WO2016073433 published May 12, 2016. CPPs typically have an amino acid composition that either contains a high relative abundance of positively charged amino acids such as lysine or arginine or has sequences that contain an alternating pattern of polar/charged amino acids and non-polar, hydrophobic amino acids.

Nucleic acid constructs that include one or more promoter sequences operably linked to one or more polynucleotides disclosed herein and optionally transcription termination sequences are provided. Plants, plant cells, plant seeds and plant nuclei that are transformed with sequences described herein are also provided.

Kits

The present disclosure provides a kit for detecting a target DNA, e.g., in a sample comprising a plurality of DNAs. In certain embodiments, the kit comprises: (a) a labeled ssDNA reporter oligonucleotide (e.g., a labeled ssDNA reporter oligonucleotide comprising a fluorescence-emitting dye pair, i.e., a FRET pair and/or a quencher/fluor pair); and (b) one or more of: (i) a guide RNA, and/or a nucleic acid encoding said guide RNA; (ii); a precursor guide RNA array comprising two or more guide RNAs (e.g., each of which has a different spacer sequence), and/or a nucleic acid encoding the precursor guide RNA array; and (iii) a Type V CRISPR/Cas effector protein (e.g., a Cas12 protein such as Cas12a, Cas12b, Cas12c, Cas12d, Cas12e), and/or a nucleic acid encoding said Type V CRISPR/Cas effector protein. In certain embodiments, a nucleic acid encoding a precursor guide RNA array includes sequence insertion sites for the insertion of spacer sequences by a user.

In certain embodiments, a subject kit comprises: (a) a labeled ssDNA reporter oligonucleotide comprising a fluorescence-emitting dye pair, i.e., a FRET pair and/or a quencher/fluor pair; and (b) one or more of: (i) a guide RNA, and/or a nucleic acid encoding said guide RNA; (ii); a precursor guide RNA array comprising two or more guide RNAs (e.g., each of which has a different spacer sequence), and/or a nucleic acid encoding the precursor guide RNA array; and (iii) a Type V CRISPR/Cas effector protein (e.g., a Cas12 protein such as Cas12a, Cas12b, Cas12c, Cas12d, Cas12e), and/or a nucleic acid encoding said Type V CRISPR/Cas effector protein.

Positive Controls

A kit of the present disclosure (e.g., one that comprises a labeled ssDNA reporter oligonucleotide and a type V CRISPR/Cas effector protein) can also include a positive control target DNA. In certain embodiments, the kit also includes a positive control guide RNA that comprises a nucleotide sequence that hybridizes to the control target DNA. In certain embodiments, the positive control target DNA is provided in various amounts, in separate containers. In certain embodiments, the positive control target DNA is provided in various known concentrations, in separate containers, along with control non-target DNAs.

Nucleic Acids

While the RNAs of the disclosure (e.g., guide RNAs and precursor guide RNA arrays) can be synthesized using any convenient method (e.g., chemical synthesis, in vitro using an RNA polymerase enzyme, e.g., T7 polymerase, T3 polymerase, SP6 polymerase, etc.), nucleic acids encoding guide RNAs and/or precursor guide RNA arrays are also envisioned. Additionally, while Type V CRISPR/Cas effector proteins (e.g., a Cas12 protein such as Cas12a, Cas12b, Cas12c, Cas12d, Cas12e) of the disclosure can be provided (e.g., as part of a kit) in protein form, nucleic acids (such as mRNA and/or DNA) encoding the Type V CRISPR/Cas effector protein (e.g., a Cas12 protein such as Cas12a, Cas12b, Cas12c, Cas12d, Cas12e)(s) can also be provided.

For example, in certain embodiments, a kit of the present disclosure comprises a nucleic acid (e.g., a DNA, e.g., a recombinant expression vector) that comprises a nucleotide sequence encoding a guide RNA. In certain embodiments, the nucleotide sequence encodes a guide RNA without a spacer sequence. For example, in certain embodiments, the nucleic acid comprises a nucleotide sequence encoding a constant region of a guide RNA (a guide RNA without a spacer sequence), and comprises an insertion site for a nucleic acid encoding a spacer sequence. In certain embodiments, a kit of the present disclosure comprises a nucleic acid (e.g., an mRNA, a DNA, e.g., a recombinant expression vector) that comprises a nucleotide sequence encoding a Type V CRISPR/Cas effector protein (e.g., a Cas12 protein such as Cas12a, Cas12b, Cas12c, Cas12d, Cas12e).

In certain embodiments, a kit of the present disclosure comprises a nucleic acid (e.g., a DNA, e.g., a recombinant expression vector) that comprises a nucleotide sequence encoding a precursor guide RNA array (e.g., where each guide RNA of the array has a different spacer sequence). In certain embodiments, one or more of the encoded guide RNAs of the array does not have a spacer sequence, e.g., the nucleic acid can include insertion site(s) for the spacer sequence(s) of one or more of the guide RNAs of the array. In certain embodiments, a subject guide RNA can include a handle from a precursor crRNA but does not necessarily have to include multiple spacer sequences.

In certain embodiments, the guide RNA-encoding nucleotide sequence (and/or the precursor guide RNA array-encoding nucleotide sequence) is operably linked to a promoter, e.g., a promoter that is functional in a plant cell. In certain embodiments, a nucleotide sequence encoding a Type V CRISPR/Cas effector protein (e.g., a Cas12 protein such as Cas12a, Cas12b, Cas12c, Cas12d, Cas12e) is operably linked to a promoter, e.g., a promoter that is functional in a plant cell, a cell type-specific promoter, a regulatable promoter, a tissue-specific promoter, and the like.

All publications, patents, and patent applications mentioned in the specification are incorporated by reference herein for the purpose cited to the same extent as if each was specifically and individually indicated to be incorporated by reference herein.

Although the foregoing disclosure has been described in some detail by way of illustration and example for purposes of clarity of understanding, it will be obvious that certain changes and modifications may be practiced within the scope of the appended claims.

The following examples are offered by way of illustration and not by way of limitation.

EXAMPLES

Example 1: Highly Sensitive and Rapid Detection of Citrus Huanglongbing Pathogen (*Candidatus Liberibacter Asiaticus*) Using Cas12a-Based Methods Citrus Huanglongbing (HLB) or greening is one of the most devastating diseases of citrus worldwide. Sensitive detection of its causal agent, *Candidatus Liberibacter asiaticus* (CLas), is critical for early diagnosis and successful management of HLB. However, current nucleic acid-based detection methods are often insufficient for the early detection of CLas from asymptomatic tissue, and unsuitable for high-throughput and field-deployable diagnosis of HLB. In this example, the development of the Cas12a-based DETECTR (DNA endonuclease-targeted CRISPR trans reporter) assay for highly specific and sensitive detection of CLas nucleic acids from infected samples is described. The DETECTR assay, which targets the five-copy nrdB gene specific to CLas, couples isothermal amplification with Cas12a trans-cleavage of a fluorescent reporter oligonucleotide and enables detection of CLas nucleic acids at the attomolar level. The DETECTR assay was capable of specifically detecting the presence of CLas across different infected citrus, periwinkle and psyllid samples, and shown to be compatible with lateral flow assay technology for potential field-deployable diagnosis. The improvements in detection sensitivity and flexibility of the DETECTR technology position the assay as a tool for early detection of CLas in infected regions.

Optimization of RPA for Specific Amplification of CLas nrdB Target

To utilize this technology for specific and sensitive detection of CLas, the nrdB gene was chosen to target. The nrdB gene contains five copies of a conserved region within the CLas genome that has previously been reported to provide robust detection of CLas via qPCR from symptomatic tissues. Specific pairs of primers for RPA were designed to amplify the nrdB fragment across all five copies. To enable Cas12a-based detection, a crRNA specific to nrdB target site was designed and synthesized via in vitro transcription (IVT). FIG. 1B and FIG. 1C depict the conserved region of the nrdB gene and the location of the crRNA spacer, PAM, and primers used in this example. A schematic of the CLas DETECTR assay that combines isothermal amplification (RPA) with Cas12-based detection is shown in FIG. 1D.

In order to ensure the optimal amplification of the nrdB target from the genomic DNA, specific primer combinations were tested and evaluated in the RPA assay using a CLas-positive sweet orange DNA sample (SO1) and a CLas-free citrus DNA sample. Out of 11 RPA primer pairs screened, three of them showed high specificity and amplicon yield (FIG. 2A). The RPA F1/RPA R3 primer combination was chosen for subsequent RPA of the nrdB target based upon the best amplicon yield and specificity observed.

Cas12a Detection of nrdB Target and Assay Sensitivity of DETECTR Vs qPCR

Figure 2B:
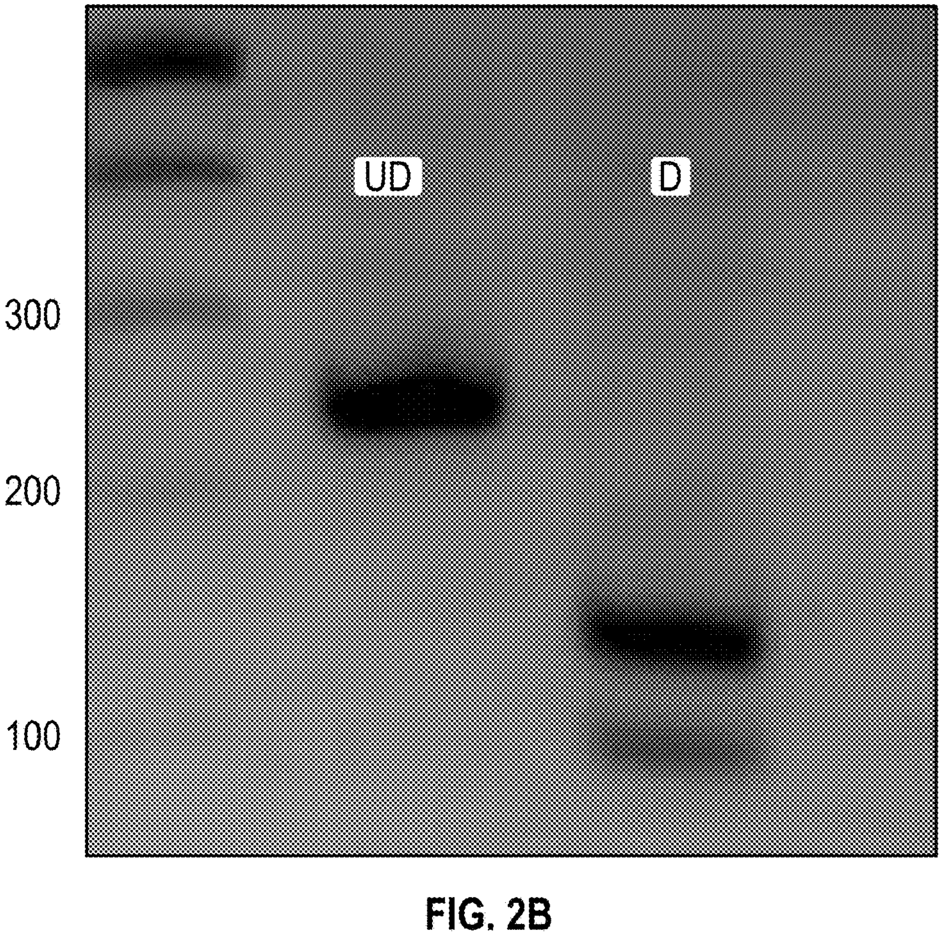
Figure 3:
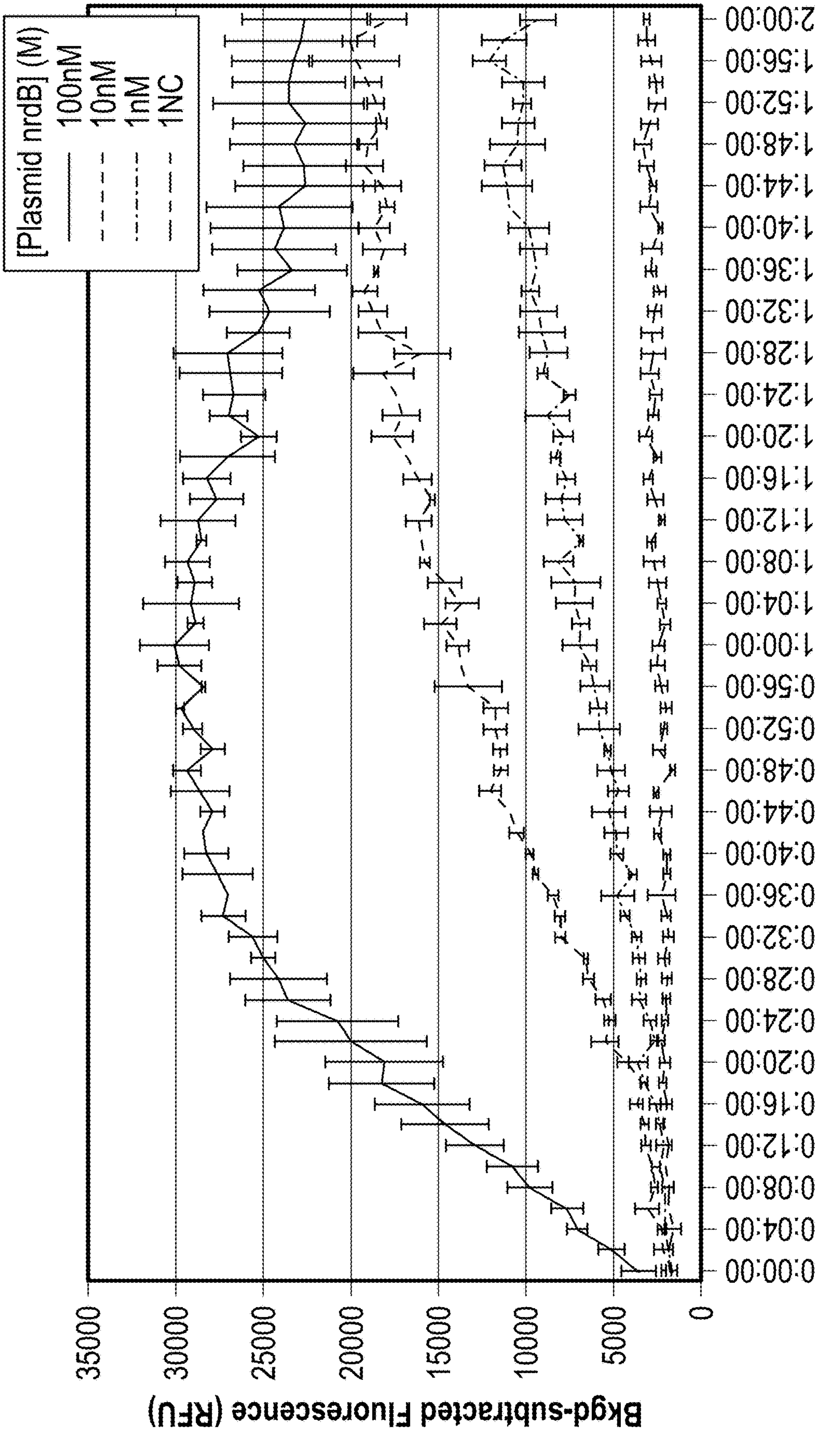
FIG. 3 shows Cas12a-based detection of target DNA vs non-target plasmid. Cas12a detection of nrdB plasmid at known concentrations compared to 100 nM non-target plasmid (NC). Error bars represent mean±s.d. when n=3 replicates.
Figures 4A, 4B:
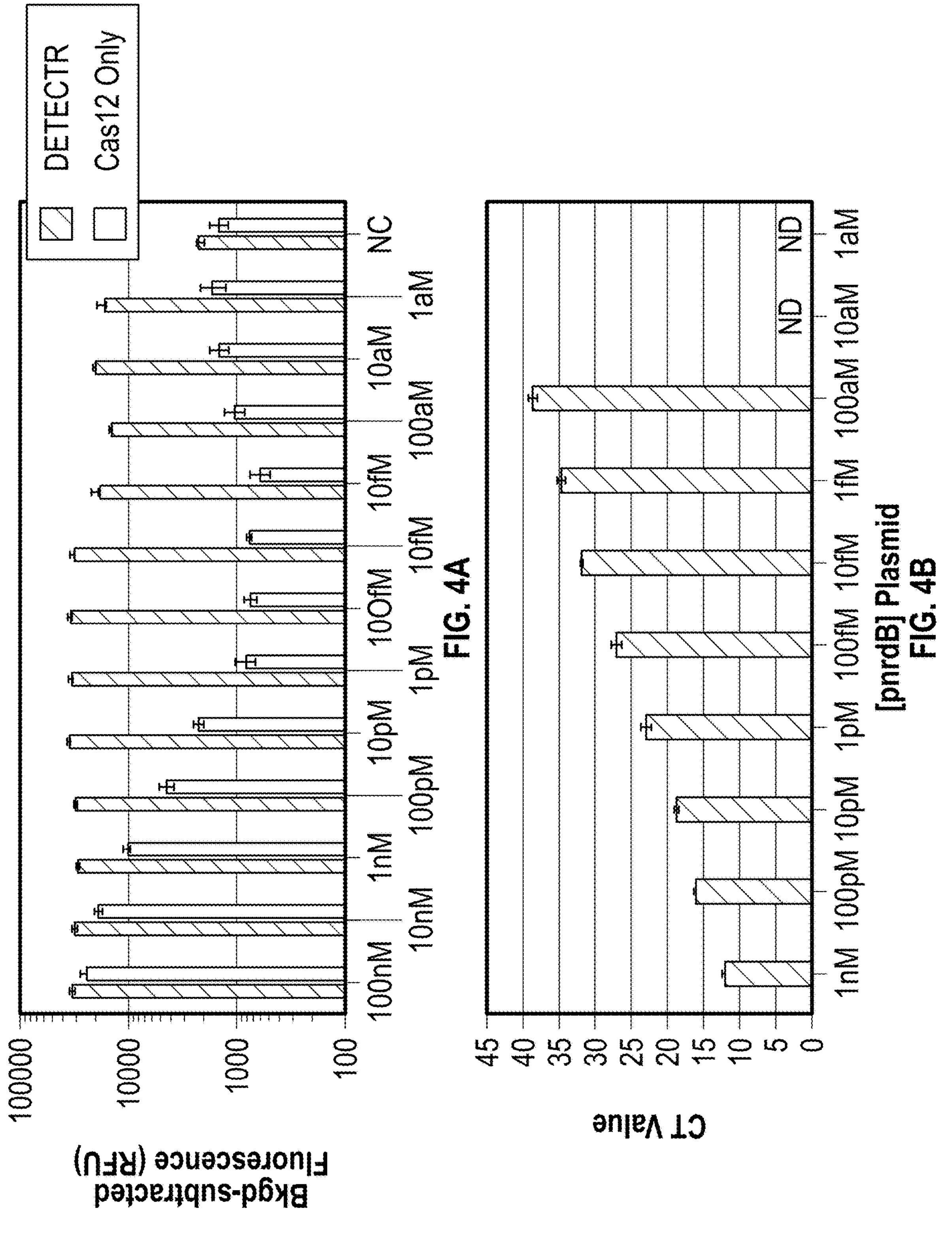
FIG. 4A-B shows detection of CLas nrdB DNA with Cas12a alone, DETECTR and qPCR.

Before proceeding with Cas12a detection, in vitro cleavage of nrdB target DNA was tested using the nrdB crRNA and Lba Cas12a nuclease. The 247 bp target DNA was specifically and efficiently cleaved to produce two predicted fragments (FIG. 2B). In order to test the sensitivity and specificity of Cas12a-based detection, the nrdB plasmid was diluted at various molar concentrations and incubated with the Cas12a detection components for two hours at 37° C. A non-target plasmid was used as a negative control. A Synergy H1 fluorescent microplate reader was used to report the accumulation of fluorescent signal production created by the activation of Cas12a and recognition of the nrdB target within a 384-well fluorescent microplate. Lba Cas12a was capable of detecting the DNA target reliably, down to 1 nM of nrB plasmid (FIG. 3). To determine the sensitivity of CLas DETECTR assay which combines Cas12a detection with RPA, the nrdB plasmid was further titrated to various molar concentrations (mM-aM) and used as a standard. A comparison between Cas12a detection alone and the DETECTR assay of the nrdB plasmid is shown in FIG. 4A. For the DETECTR assay series, a 10-minute RPA was performed prior to the 1-hour collateral detection via Cas12a for all samples, while the Cas12a only series omitted the initial RPA portion. By itself, Cas12a was capable of successful detection at the nanomolar level. When coupled with the RPA, the CLas DETECTR assay reached attomolar sensitivity. With the same primers and nrdB plasmid dilution series, however, real-time qPCR was only capable of detecting the nrdB DNA at 1.0 or at most 0.1 femtomolar levels (FIG. 4B), which is 100 or possibly 1000 times less sensitive than the Cas12a-based DETECTR assay.

Specific Detection of CLas from Infected Samples Using the DETECTR Assay

Figure 5:
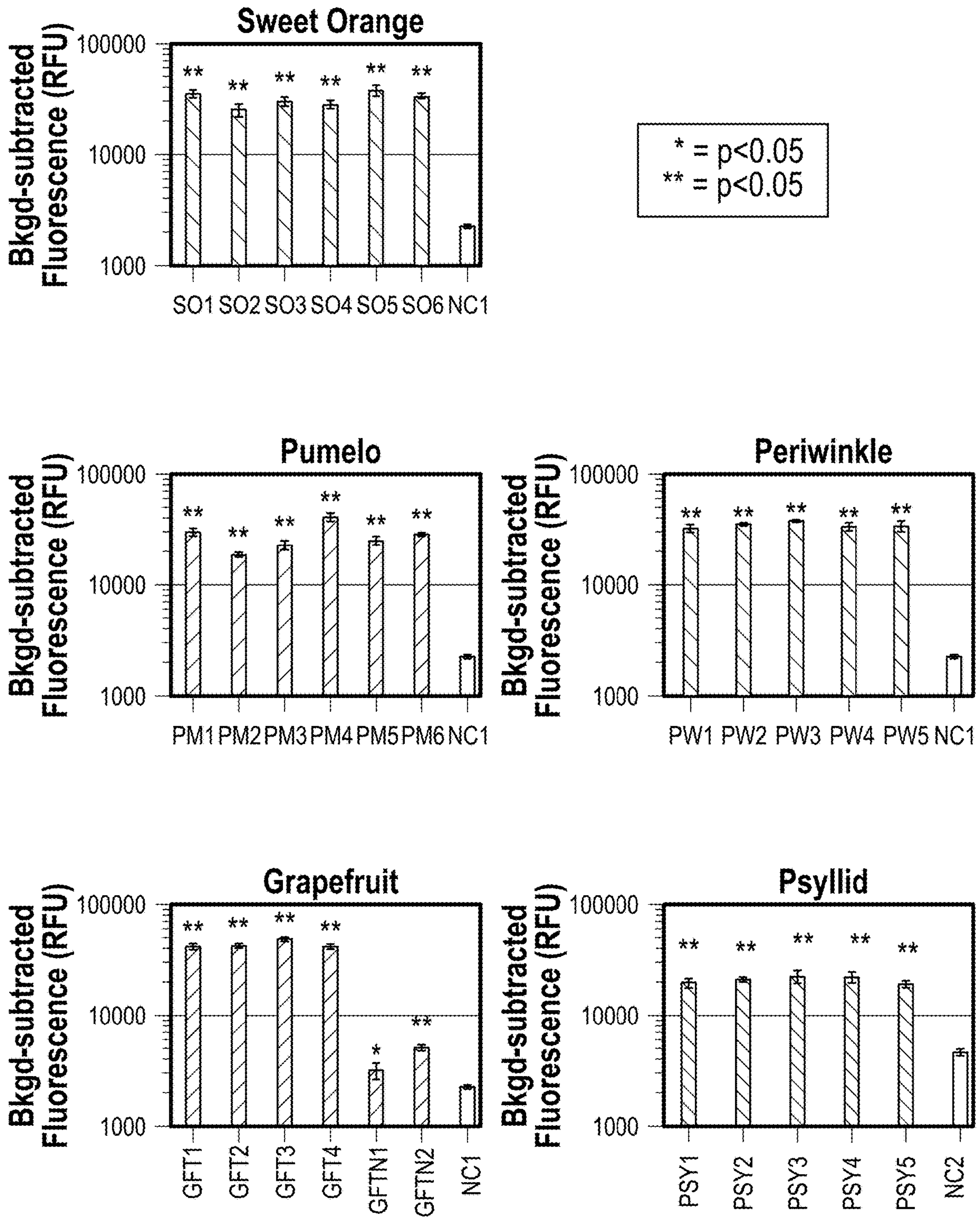
FIG. 5 shows detection of CLas-infected samples using DETECTR assay. Detection of CLas was performed using 28 DNA samples from sweet orange, pumelo, grapefruit, periwinkle, psyllid. The grapefruit samples GFTN1 and GFTN2 were potentially infected, but showed negative for CLas based on qPCR detection. Genomic DNAs extracted from uninfected grapefruit cultivar Duncan (NC1) and CLas-free psyllids (NC2) were used as negative controls. Error bars indicate the mean of the highest fluorescent value over 1 hr±s.d. when n=3 replicates. A two tailed T-Test was done to provide p-values of infected samples compared to control, where * p≤0.01 and ** p≤0.001.

After evaluating its sensitivity and specificity, the CLas DETECTR assay was used to detect and confirm the presence of CLas nucleic acids in the infected citrus, periwinkle and psyllid samples collected from Florida, USA. A total of twenty-eight DNA samples from various species (sweet orange, pumelo, grapefruit, periwinkle, and psyllid) were tested along with a negative control (uninfected Duncan grapefruit sample). As expected, the CLas DETECTR assay confirmed that all 26 samples are positive for CLas compared to the negative control (FIG. 5). Interestingly, two grapefruit DNA samples (GFTN1 and GFTN2) were previously tested by qPCR to be CLas negative. However, they showed weak positivity of CLas in the DETECTR assay.

Lateral Flow Compatibility for the CLas DETECTR Assay

Figure 6:
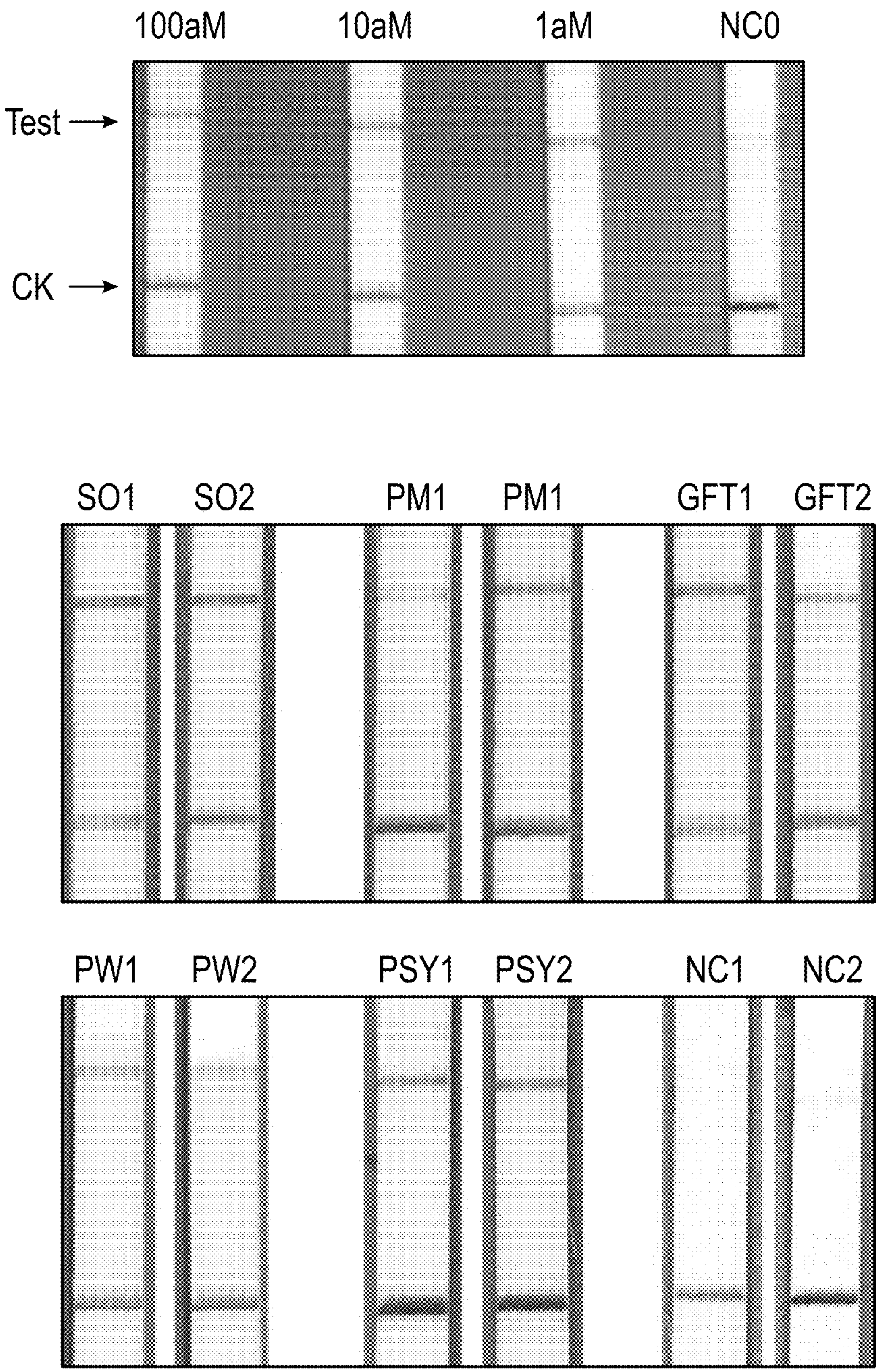
FIG. 6 shows lateral flow reading from CLas DETECTR assay. Lateral flow strips were incubated for 10 minutes in the hybridization product prior to taking the image photo. Both serial dilution of the nrdB plasmid (100 aM, 10 aM, 1 aM and negative control 0) and genomic DNAs from the infected samples were tested with the lateral flow assay. SO: sweet orange, PM: pumelo, GFT: grapefruit, PW: periwinkle, PSY: psyllid, NC1: negative control 1 (uninfected grapefruit DNA), NC2: negative control 2 (uninfected psyllid DNA). The lateral flow strip is comprised of three segments, the sample application pad, the streptavidin band (control), and the antibody capture band (sample). Following sample application, the intact oligonucleotide reporter will be bound by streptavidin band. Anti-fluorescein antibodies labeled with gold nanoparticles will bind to the fluorescein end of the reporter resulting in the generation of a dark purple color. When the oligonucleotide reporter is cleaved in the presence of target DNA due to collateral activity, the gold nanoparticle labeled antibodies continue to flow over to the antibody capture band (sample), forming a dark purple color at the second location.

In addition to fluorescence detection using a microplate reader, we employed lateral flow strips (HybriDetect, Milenia Biotec) for a visual and semi-quantitative DETECTR assay that will likely facilitate in-field detection of CLas. Two samples from each plant or insect species, along with various 1000-fold dilutions of the standard, were run on lateral flow strips to determine the presence of CLas (FIG. 6). The CLas DETECTR assay was modified for the lateral flow strip assay by utilizing the ssDNA reporter oligonucleotide that contained 5'-FAM and 3'-biotin modifications, enabling the reaction product to migrate to the test band on an immunostrip after the cleavage of the ssDNA reporter oligonucleotide by the activated Cas12a. All infected samples tested have shown positive detection of CLas on the lateral flow strips (FIG. 6). The use of diluted samples from the nrdB plasmid standard indicated the attomolar sensitivity for the lateral flow assay.

Materials and Methods

Nucleic acid preparation and in vitro cleavage assay: Total genomic DNAs were extracted from CLas-infected plant or psyllid tissues using the cetyltrimethylammonium bromide (CTAB)/column purification method. The nrdB target DNA fragment was amplified by PCR from the CLas-containing genomic DNA with a pair of specific primers (nrdB RPA F1, CAT CAT GCG AGA TGA ATC ACT GCA TCT CAA (SEQ ID NO: 1) and nrdB RPA R3, ACC GAT TTG GTG ACA ACG ACG ATT GGC G (SEQ ID NO: 2); also see TABLE 1) and cloned into pGEM T-Easy (Promega). To synthesize the crRNA targeting nrdB, the partially dsDNA template was generated by annealing the T7 promoter sequence (T7 IVT F: TAA TAC GAC TCA CTA TAG (SEQ ID NO: 5)) with the nrdB crRNA oligonucleotide (nrdB IVT: TCG AAA TCG CCT ATG CAC ATA TCT ACA CTT AGT AGA AAT TAC TAT AGT GAG TCG TAT TA (SEQ ID NO: 6)). In vitro transcription (IVT) by T7 RNA polymerase was performed using the HiScribe T7 High Yield RNA Synthesis Kit (NEB) based on the manufacturer's instruction. The resulting crRNA was purified using the RNA Clean & Concentrator kit (ZYMO Research). In vitro cleavage assay was performed at 37° C. for 1 hr in 20 μl 1×NEB 2.1 reaction buffer using 50 nM nrdB target amplicon, 50 nM En Gen Lba Cas12a (NEB) and 50 nM nrdB crRNA. The reaction products were treated with proteinase K at room temperature for 10 minutes before running on agarose gel for analysis. In addition, two fluorescent reporter oligonucleotides (5'-56-FAMN/TTA TT/3IABkFQ/-3' and 5'-56-FAMN/TTA TT/3Bio/-3') were synthesized by IDT. 56-FAMN/TTA TT/3IABkFQ/is conjugated with FAM (Fluorescein) and FQ (fluorescence quencher) for fluorescence microplate reader while FAMN/TTA TT/3Bio contains both FAM and biotin modifications for lateral flow assay.

CLas nrdB DETECTOR assay: The DETECTOR assay combines RPA using TwistAmp nfo kit (TwistDx) with the Cas12a detection. The RPA assay was performed in 20 μL reaction (TwistDx Liquid Basic) consisting of 50 ng genomic DNA, 0.48 pM forward and reverse primers, RPA enzyme mixes and reaction buffer. The reaction was initiated with the addition of 14 nM of magnesium acetate and incubated at 37° C. for 10 minutes. Subsequent Cas12a detection was performed at 37° C. for 1 hr in Synergy H1 BioTEK microplate reader after adding 2 μL of RPA reaction product into the pre-incubated Cas12a components as mentioned above. The detection values from the CLas-infected samples were normalized to the maximum-mean fluorescent signal observed using the crRNA targeting the 5-copy number nrdB target. A one-way ANOVA and Dunnett's post-test was used to determine the positive value cutoff ($p \leq 0.05$) for the identification of CLas from infected samples.

qPCR assay of CLas nrdB: qPCR was performed using TempAssure 0.1 mL PCR tube strips (USA Scientific) with optical caps in a real-time thermal cycler (Bio-Rad CFX96). Each tube contains a 20 μL reaction mixture, which includes the GoTaq qPCR Master Mix (Promega), a series of diluted nrdB plasmid DNAs (identical to the ones used in the Cas12a DETECTR assay), and the same primer pair (F1 and R3) used in the RPA assay. Thermal cycling reactions consisted of 2 min at 95° C. followed by 40 cycles of 15 sec at 95° C. and 1 min at 60° C.

TABLE 1

| | |
|---|---|
| nrdB RPA F1* | CATCATGCGAGATGAATCACTGCATCTCAA (SEQ ID NO: 1) |
| nrdB RPA R3* | ACCGATTTGGTGACAACGACGATTGGCG (SEQ ID NO: 2) |
| nrdB RPA R1 | CCGATTTGGTGACAACGACGATTGGCGATG (SEQ ID NO: 3) |
| nrdB RPA R2 | ACGACGATTGGCGATGAACTGCATATATTG (SEQ ID NO: 4) |
| T7 IVT F | TAATACGACTCACTATAG (SEQ ID NO: 5) |
| nrdB IVT | **TCGAAATCGCCTATGCACAT**ATCTACACTTAGTAGAAATTACTATAGTGAGTCGTATTA (SEQ ID NO: 6) |
| nrdB spacer | **ATGTGCATAGGCGATTTCGA** (SEQ ID NO: 7) |
| nrdB crRNA | TAATTTCTACTAAGTGTAGAT**ATGTGCATAGGCGATTTCGA** (SEQ ID NO: 8) |
| Reporter oligo (PR) | 56-FAMN/TTA TT/3IABKFQ/ |
| Reporter oligo (LF) | 56-FAMN/TTA TT/3Bio/ |

Boldface indicates spacer sequence; Asterisk indicates the primers used for the CLas DETECTR assay.

Cas12a detection of CLas target nrdB: Cas12a detection of nrdB target plasmid was performed using pre-incubated Cas12a detection components consisting of 500 nM of EnGen Lba Cas12a (NEB), 625 nM of in vitro transcribed crRNA, and 500 nM of custom fluorescent reporter (56-FAMN/TTA TT/3IABkFQ) at 37° C. for 30 minutes prior to the addition of target DNA. Collateral detection was initiated by adding a series of diluted plasmid DNAs in 20 μL NEB 2.1 buffer to a final concentration of 50 nM of Lba Cas12a, 62.5 nM of crRNA, and 50 nM of 56-FAMN/TTA TT/3IABkFQ. Reactions were incubated at 37° C. in the Synergy H1 BioTEK microplate reader for 60 or 120 minute time courses with fluorescence detection (excitation 495 nm, emission 535 nm) occurring every 2 minutes.

Lateral Flow Assay: The CLas nrdB DETECTR reaction was performed as described above using the RPA reaction products and Cas12a detection components containing the 5'-56-FAMN/TTA TT/3Bio/-3' fluorescent reporter. Lateral flow assay was carried out according to the HybriDetect protocol (Milenia Biotec). The HybriDetect assay buffer (100 μl) was added to the DETECTOR reaction and incubated at room temperature for 5 min. A lateral flow strip was dipped into the reaction mix for 5-10 minutes for visual detection.

Discussion

This example reports the development and validation of Cas12a-based diagnostics for sensitive and specific detection of CLas by targeting the conserved region of its nrdB gene. Previously, the nrdB gene was used to detect CLas nucleic acids via qPCR and was reported to increase CLas detection sensitivity by three-fold compared to 16S rRNA gene due to the higher copy number of the conserved nrdB region, and twice as stable compared to the intragenic prophage sequences. Following this premise for increased sensitivity, specific primers and a crRNA were designed based on the nrdB region for highly sensitive and specific detection of CLas nucleic acids. In combination with RPA, the Cas12a-based DETECTR assay achieved the attomolar sensitivity for detection of CLas DNAs (FIG. 4A). By contrast, only 1.0 or at most 0.1 femtomolar sensitivity were achieved for the nrdB DNA detection in real-time qPCR experiments (FIG. 4B). Therefore, the Cas12a DETECTR assay is 100 or even 1000 times more sensitive than the qPCR for detecting CLas DNA. Other techniques that boast early detection capabilities of CLas utilize specialized instrumentation for volatile organic compounds analysis along with in situ stains to visualize leaves and locations of concentrated CLas for direct confirmation or to increase the sensitivity of nucleic acid diagnosis approaches. These techniques show great promise, however, have limited feasibility in terms of rapid and high-throughput diagnosis of CLas infection. By contrast, the Cas12a-based DETCTR assay can lead to more sensitive and rapid detection of CLas nucleic acid and facilitates in-field diagnosis of HLB.

Other techniques of isothermal amplification such as LAMP (loop-mediated isothermal amplification), SDA (strand displacement amplification), and NEAR (nicking enzyme amplification reaction) can be used as a substitute for RPA in CRISPR/Cas-based detection of pathogen nucleic acids which are also commonly used with lateral flow technology. HOLMES v2 platform utilizes LAMP prior to Cas12b-based detection. Once activated, Cas12b also exhibits general ssDNase activity which could pose problems for ssDNA amplicon intermediates during LAMP that could be destroyed. However, Cas12b used in HOLMES v2 exhibits a higher rate of trans-activation, reporter degradation, as compared to Cas12a, which could result in a shorter assay with higher sensitivity, in turn producing a faster diagnostics result.

The DETECTR assay can truly shine when used to detect pathogens that exist in low titers such as CLas, phytoplasmas and some viruses, where qPCR and qRT-PCR results can be inconclusive due to their limit in detection. However, other pathogens that are more abundant may also benefit from the Cas12a-based detection that omit the initial RPA step. Due to the sufficient sensitivity of LbaCas12a, Cas12a detection alone may be suitable for detection of many pathogens based upon the recognition of nucleic acid sequence from total DNAs of infected or asymptomatic tissues. By omitting the RPA portion of the reaction, the cost is considerably reduced. Recently, another sensitive Cas nuclease-based detection system, CIRSPR-Chip has been published reporting the detection of target genes without amplification down to 1.7 fM via immobilized dCas9 on a graphene transistor. These methods may hold promise in rapid detection by omitting amplification of target nucleic acids.

Currently, Cas12a-based detection such as the DETECTR method is limited in multiplexing capabilities. Since ssDNase activity is non-specific after the activation of Cas12a, it would not be possible to distinguish which reporter was degraded between Cas12 homologs used in the same reaction. SHERLOCK v2, a CRISPR/Cas-based detection platform that utilizes both Cas12a and Cas13a, is capable of multiplexed pathogen detection due to the di-nucleotide preferences in the ssRNase activity of Cas13a. Each ssRNA reporter for Cas13a contained their own specific fluorophore that was detectable in a microplate reader, providing an indication of which nuclease became activated based upon the fluorescent readings. It is noted that only a single Cas12a can be used in this reaction due to the non-specific nature of the ssDNase activity post Cas12a activation. SHERLOCK v2 has demonstrated the ability to simultaneously detect four different pathogens in a single reaction, creating a platform for highly sensitive and rapid multiplexed pathogen detection in point of care diagnostics.

Together these results show the CRISPR/Cas-based detection strategies improve upon current diagnostics of HLB by providing specific and highly sensitive detection of CLas nucleic acids. The CLas DETECTR assay was capable of detecting the nrdB target down to the attomolar level in both the microplate reader- and lateral flow strip-based assays. In addition, CLas DETECTR assay has the potential for being used in-field diagnostics to rapidly detect CLas from infected samples by using lateral flow strips or portable endpoint fluorometers. The improvement in detection sensitivity and ease of use compared to traditional methodologies such as qPCR position the CLas DETECTR assay as a promising tool for HLB diagnostics in CLas-infected regions.

REFERENCES

Aman, R., Mahas, A., Marsic, T., Hassan, N., Mahfouz, M. M. 2020. Efficient, rapid, and sensitive detection of plant RNA viruses with one-pot RT-RPA-CRISPR/Cas12a assay. Front Microbiol. 11:610872.

Chen, J. S., Ma, E., Harrington, L. B., Da Costa, M., Tian, X., Palefsky, J. M., et al. 2018. CRISPR-Cas12a target binding unleashes indiscriminate single-stranded DNase activity. Science 360:436-439.

Fujikawa, T., and Iwanami, T. 2012. Sensitive and robust detection of citrus greening (huanglongbing) bacterium "*Candidatus Liberibacter asiaticus*" by DNA amplification with new 16S rDNA-specific primers. Mol. Cell. Probes 26:194-197.

Ghosh, D. K., Kokane, A. D., Kokane, S. B., Tenzin, J., Gubyad, M. G., Wangdi, P., Murkute, A. A., Sharma, A. K., Gowda, S. 2021. Detection and Molecular Characterization of '*Candidatus Liberibacter asiaticus*' and *Citrus* Tristeza Virus Associated with *Citrus* Decline in Bhutan. Phytopathology.

Gootenberg, J. S., Abudayyeh, O. O., Kellner, M. J., Joung, J., Collins, J. J., and Zhang, F. 2018. Multiplexed and portable nucleic acid detection platform with Cas13, Cas12a and Csm6. Science 360:439-444.

Gootenberg, J. S., Abudayyeh, O. O., Lee, J. W., Essletzbichler, P., Dy, A. J., Joung, J., et al. 2017. Nucleic acid detection with CRISPR-Cas13a/C2c2. Science 356:438-442.

Gottwald, T. R., Luo, W., Posny, D., Poole, G. H., Louws, F., Mccollum, T. G., Hartung, J. S., Bai, J., Duan, Y., Taylor, E. L., Da Graga, J., Schneider, W., Polek, M., Hall, D. 2020. Canine olfactory detection of a vectored phytobacterial pathogen, *Liberibacter asiaticus*, and intergration with disease control. Proc. Natl. Acad. Sci. 117:3492-3501.

Hajian, R., Balderston, S., Tran, T., deBoer, T., Etienne, J., Sandhu, M., et al. 2019. Detection of unamplified target genes via CRISPR-Cas9 immobilized on a graphene field-effect transistor. Nat. Biomed. Eng. 3:427-437.

Iftikhar, Y., Rauf, S., Shahzad, U., and Zahid, M. A. 2016. Huanglongbing: Pathogen detection system for integrated disease management—A review. J. Saudi Soc. Agric. Sci. 15:1-11.

Jagoueix, S., Bove, J. M., and Gamier, M. 1994. The phloem-limited bacterium of greening disease of citrus is a member of the a subdivision of the Proteobacteria. Int. J. Syst. Bacteriol. 44:379-386.

Jiao, J., Kong, K., Han, J., Song, S., Bai, T., Song, C., Wang, M., Yan, Z., Zhang, H., Zhang, R., Feng, J., Zheng, X. 2021. Field detection of multiple RNA viruses/viroids in apple using a CRISPR/Cas12a-based visual assay. Plant Biotechnol J. 19:394-405.

Kang, H., Peng, Y., Hua, K., Deng, Y., Bellizzi, M., Gupta, D. R., Mahmud, N. U., Urashima, A. S., Paul, S. K., Peterson, G., Zhou, Y., Zhou, X., Islam, M. T., Wang, G.-L. 2020. Rapid Detection of Wheat Blast Pathogen *Magnaporthe Oryzae Triticum* Pathotype using Genome-Specific Primers and Cas12a-mediated Technology. Engineering.

Keremane, M. L., Ramadugu, C., Rodriguez, E., Kubota, R., Shibata, S., Hall, D. G., et al. 2015. A rapid field detection system for citrus huanglongbing associated "*Candidatus Liberibacter asiaticus*" from the psyllid vector, Diaphorina *citri* Kuwayama and its implications in disease management. Crop Prot. 68:41-48.

Li, L., Li, S., Wu, N., Wu, J., Wang, G., Zhao, G., and Wang, J. 2019. HOLMESv2: A CRISPR-Cas12b-assisted platform for nucleic acid detection and DNA methylation quantitation. ACS Synth. Biol. 8:2228-2237.

Morgan, J. K., Zhou, L., Li, W., Shatters, R. G., Keremane, M., and Duan, Y. P. 2012. Improved real-time PCR detection of "*Candidatus Liberibacter asiaticus*" from citrus and psyllid hosts by targeting the intragenic tandem-repeats of its prophage genes. Mol. Cell. Probes 26:90-98.

Pandey, S. S., and Wang, N. 2019. Targeted early detection of citrus Huanglongbing causal agent '*Candidatus Liberibacter asiaticus*' before symptom expression. Phytopathology 109:952-959.

Rigano, L. A., Malamud, F., Orce, I. G., Filippone, M. P., Marano, M. R., Do Amaral, A. M., et al. 2014. Rapid and sensitive detection of *Candidatus Liberibacter asiaticus* by loop mediated isothermal amplification combined with a lateral flow dipstick. BMC Microbiol. 14:86.

Song, X, Bhattarai, K., Lv, D., Gao, F., and Ying, X. 2017. Can CRISPR Win the Battle against Huanglongbing? J. Plant Pathol. Microbiol. 8:9.

Teng, F., Guo, L., Cui, T., Wang, X. G., Xu, K., Gao, Q., et al. 2019. CDetection: CRISPR-Cas12b-based DNA detection with sub-attomolar sensitivity and single-base specificity. Genome Biol. 20:132.

Valdes, R. A., Ortiz, J. C. D., Beache, M. B., Cabello, J. A., Chivez, E. C., Pagaza, Y. R., et al. 2016. A review of techniques for detecting huanglongbing (Greening) in citrus. Can. J. Microbiol. 62:803-811.

Wheatley, M. S. and Yang, Y. 2020. Versatile applications of the CRISPR/Cas toolkit in plant pathology and disease management. Phytopathology.

Zetsche, B., Gootenberg, J. S., Abudayyeh, O. O., Slaymaker, I. M., Makarova, K. S., Essletzbichler, P., et al. 2015. Cpf1 is a single RNA-guided endonuclease of a class 2 CRISPR-Cas system. Cell. 163:759-771.

Zhang, Y.-m., Zhang, Y., and Xie, K. 2020. Evaluation of CRISPR/Cas12a-based DNA detection for fast pathogen diagnosis and GMO test in rice. Molecular Breeding 40:11.

Zheng, Z., Xu, M., Bao, M., Wu, F., Chen, J., and Deng, X. 2016. Unusual five copies and dual forms of nrdB in "*Candidatus Liberibacter asiaticus*": Biological implications and PCR detection application. Sci Rep 6:39020.

Zhong, X., Liu, X., Lou, B., Zhou, C, and Wang, X. 2018. Development of a sensitive and reliable droplet digital PCR assay for the detection of '*Candidatus Liberibacter asiaticus*.' J. Integr. Agric. 17:483-487.

Zhou, L., Powell, C. A., Hoffman, M. T., Li, W., Fan, G., Liu, B., Lin, H., Duan, Y. 2011. Diversity and plasticity of the intracellular plant pathogen and insect symbiont "*Candidatus Liberibacter asiaticus*" as revealed by hypervariable prophage genes with intragenic tandem repeats. Appl Environ Microbiol. 77:6663-6673.

Example 2: Cas12a-Based Diagnostics for Potato Purple Top Disease Complex Associated with Infection by '*Candidatus Phytoplasma trifolii*'-Related Strains '*Candidatus Phytoplasma trifolii*' is a cell wall-less phytopathogenic bacterium that infects many agriculturally important plant species such as alfalfa, clover, eggplant, pepper, potato, and tomato. The phytoplasma is responsible for repeated outbreaks of potato purple top (PPT) and potato witches' broom (PWB) that occurred along the Pacific Coast of the United States since 2002, inflicting significant economic losses. To effectively manage these phytoplasmal diseases, it is important to develop diagnostic tools for specific, sensitive and rapid detection of the pathogens. In this example, the development of a DNA endonuclease targeted CRISPR trans reporter (DETECTR) assay that couples isothermal amplification and Cas12a trans-cleavage of fluorescent oligonucleotide reporter for highly sensitive and specific detection of '*Candidatus Phytoplasma trifolii*'-related strains responsible for PPT and PWB is described. The DETECTR assay was capable of specifically detecting the 16S-23S ribosomal DNA (rDNA) intergenic transcribed spacer (ITS) sequences from PPT- and PWB-diseased samples at the attomolar sensitivity level. Furthermore, the DETECTR strategy allows flexibility to capture assay outputs with fluorescent microplate reader or lateral flow assay for potentially high-throughput and/or field-deployable disease diagnostics.

Primer and crRNA Design for Specific Detection of 'Ca. *Phytoplasma trifolii*'.

The DETECTR assay combines isothermal amplification, in the form of RPA, and Cas12a activation and collateral cleavage of fluorescently labeled oligonucleotides (FIG. 7A). PPT WA4, a subgroup 16SrVI-A strain, was selected as a reference strain to design RPA primers and crRNA spacers for the specific detection of group 16SrVI phytoplasmas. The 16S-23S rDNA ITS sequence from the strain PPT WA4 was aligned against the same regions from other ribophylogroups of phytoplasmas. Primers for the RPA were designed over conserved sequences of the 16S-23S rDNA ITS region to provide reliable primer hybridization during the RPA reaction and amplification of the 16S-23S rDNA ITS sequences across different phytoplasma ribo-phylogroups. The crRNA was designed over a unique ITS sequence present only in group 16SrVI phytoplasma. FIG. 1B and FIG. 1C depict the PPT 16S-23S rDNA ITS amplicon as well as the RPA primers, crRNA spacer and PAM used for the 16SrVI DETECTR assay.

Highly Sensitive Detection of PPT Target DNA with DETECTR.

Figure 8A:
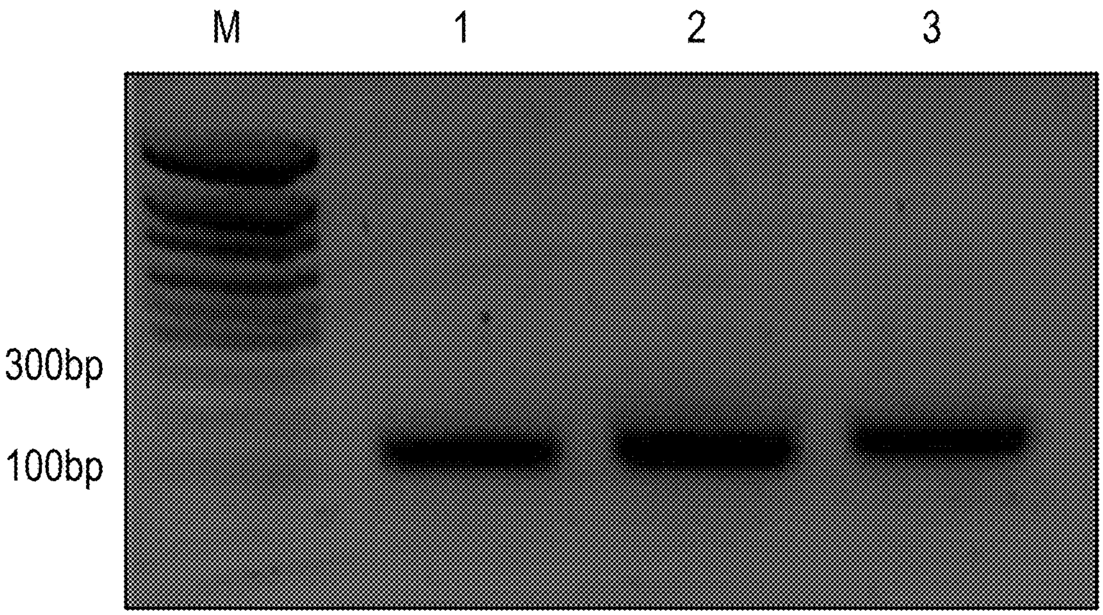
FIG. 8A-B shows RPA primer evaluation and target DNA cleavage.
Figure 8B:
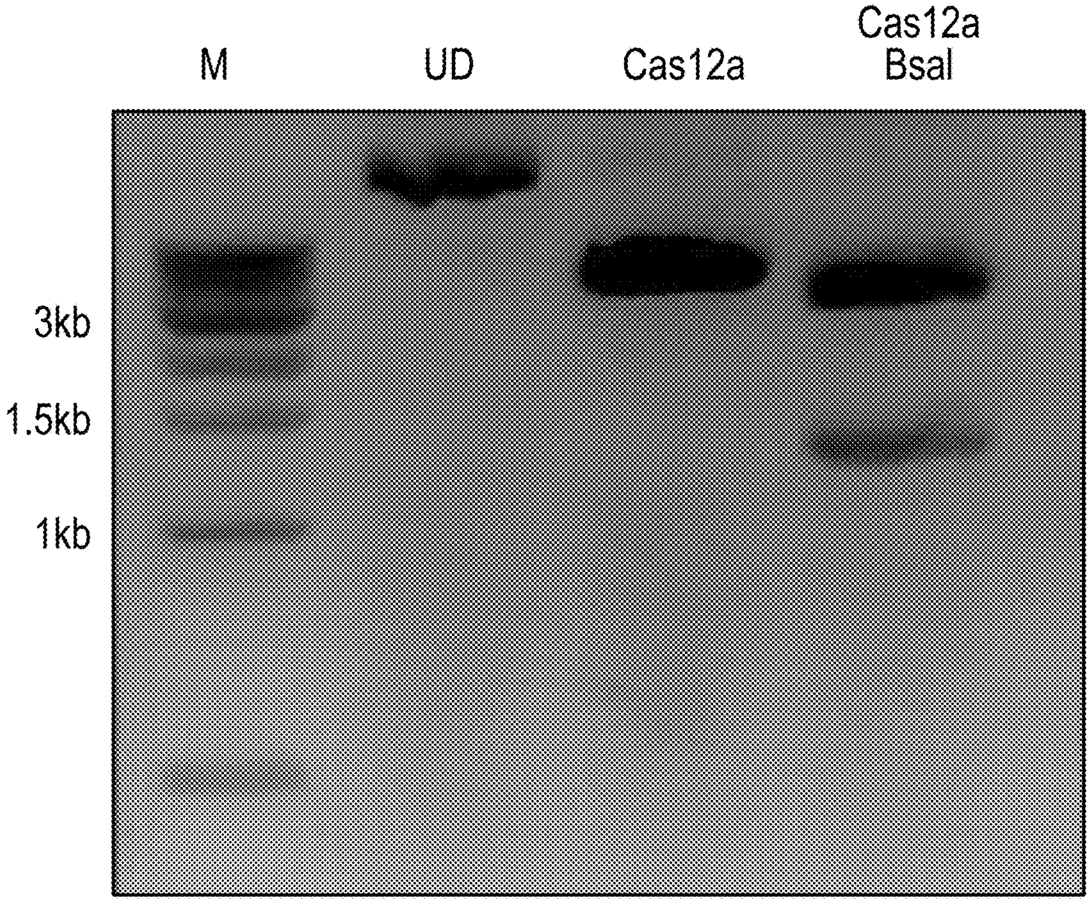
Figure 9:
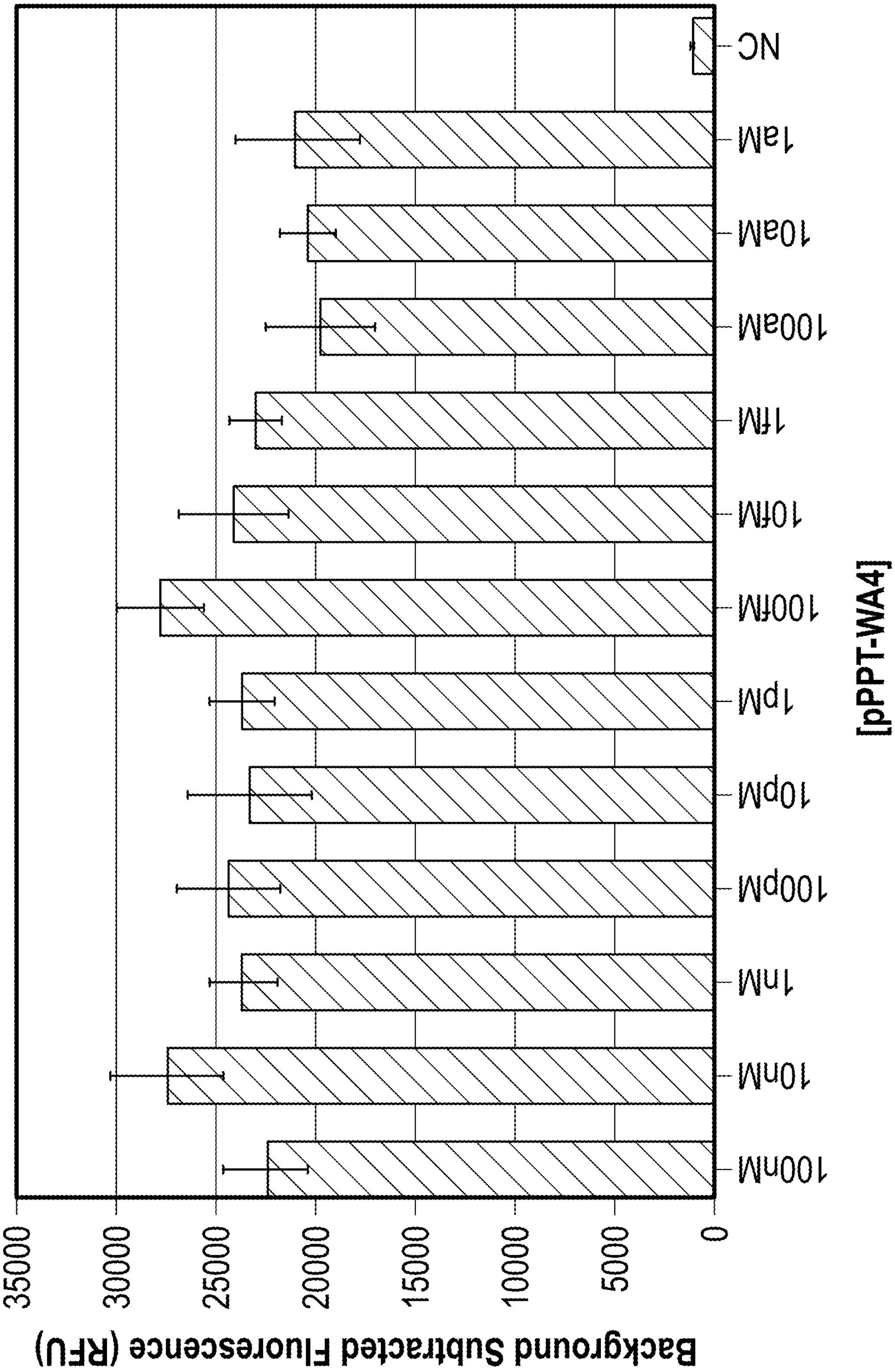
FIG. 9 shows sensitivity of PPT 16S rDNA DETECTR assay. The target DNA plasmid containing PPT WA4 16S rDNA fragment was diluted to various molar concentrations for the DETECTR assay. Note that PPT WA4 16S-23S rDNA ITS target was detectable at attomolar sensitivity. Error bars represent mean±SD when n=3 replicates.

To optimize the PPT 16S rDNA DETECTR assay, nine primer combinations were tested for the RPA amplification portion of the DETECTR assay. The RPA-F2/R3 primer combination was selected based on its specificity and efficiency to amplify the PPT16S-23S ITS amplicon (FIG. 8A). Before proceeding with Cas12a detection, in vitro cleavage of target DNA plasmid (pPPT-WA4) was tested using the IVT crRNA and Lba Cas12a nuclease. The target DNA plasmid was specifically and efficiently cleaved to produce predicted fragments, demonstrating that the IVT crRNA is appropriate for subsequent Cas12a detection assay (FIG. 8B). In order to test the sensitivity of DETECTR assay, the pPPT-WA4 plasmid was diluted at various molar concentrations and used for RPA reaction and Cas12a detection. The DETECTR assay for PPT 16SrVI was highly sensitive and capable of detecting the target DNA at the attomolar level (FIG. 9).

Specificity of the 16SrVI DETECTR Assay for 'Ca. *Phytoplasma trifolii*' and Related Strains.

Figure 10:
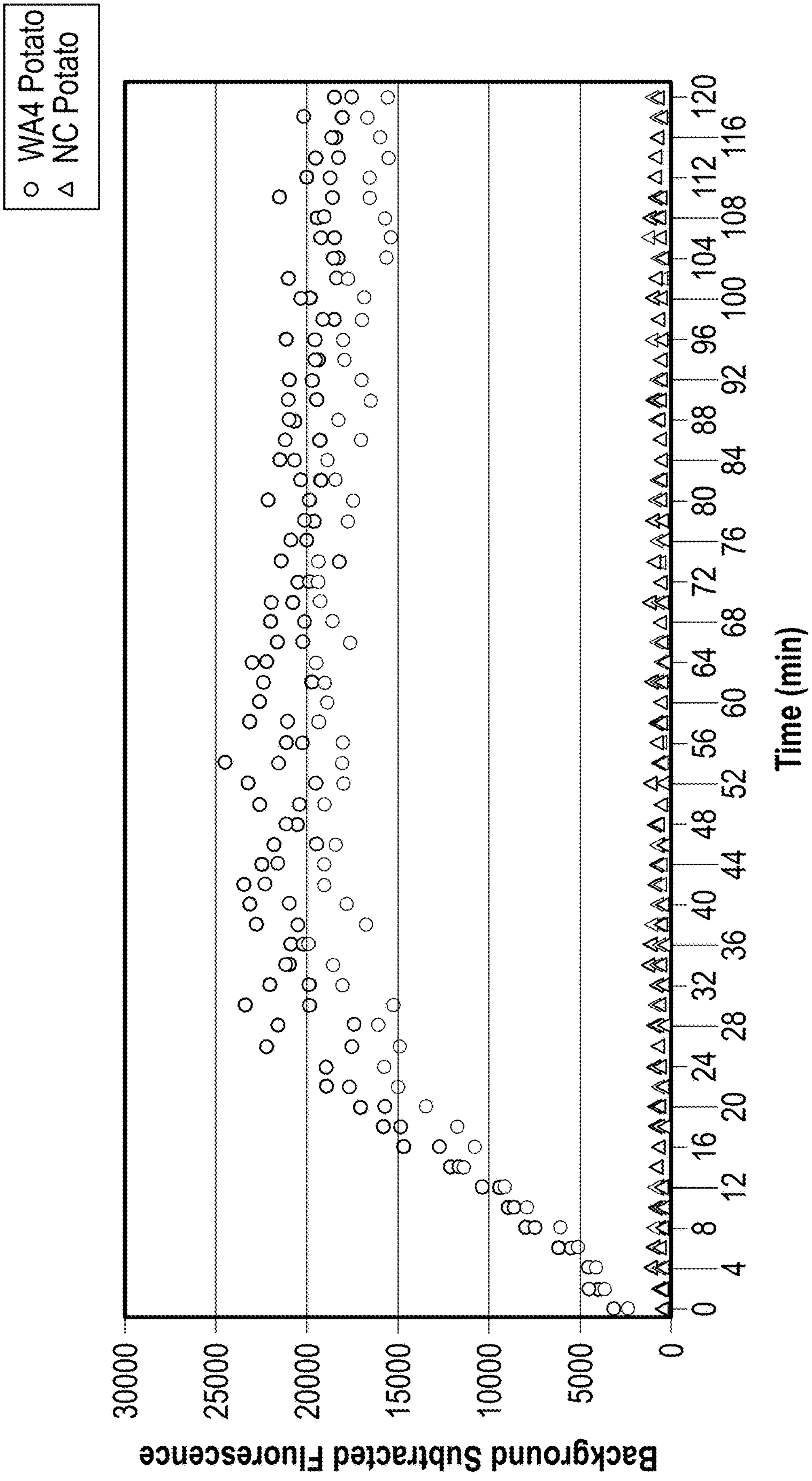
FIG. 10 shows time course of Cas12a detection using potato genomic DNAs. The DETCTR assay, which combines RPA and Cas12a detection, was carried out using the PPT WA4 infected potato DNA (WA4 potato, circle) and a disease-free potato DNA sample as a negative control (NC potato, triangle).
Figure 11A:
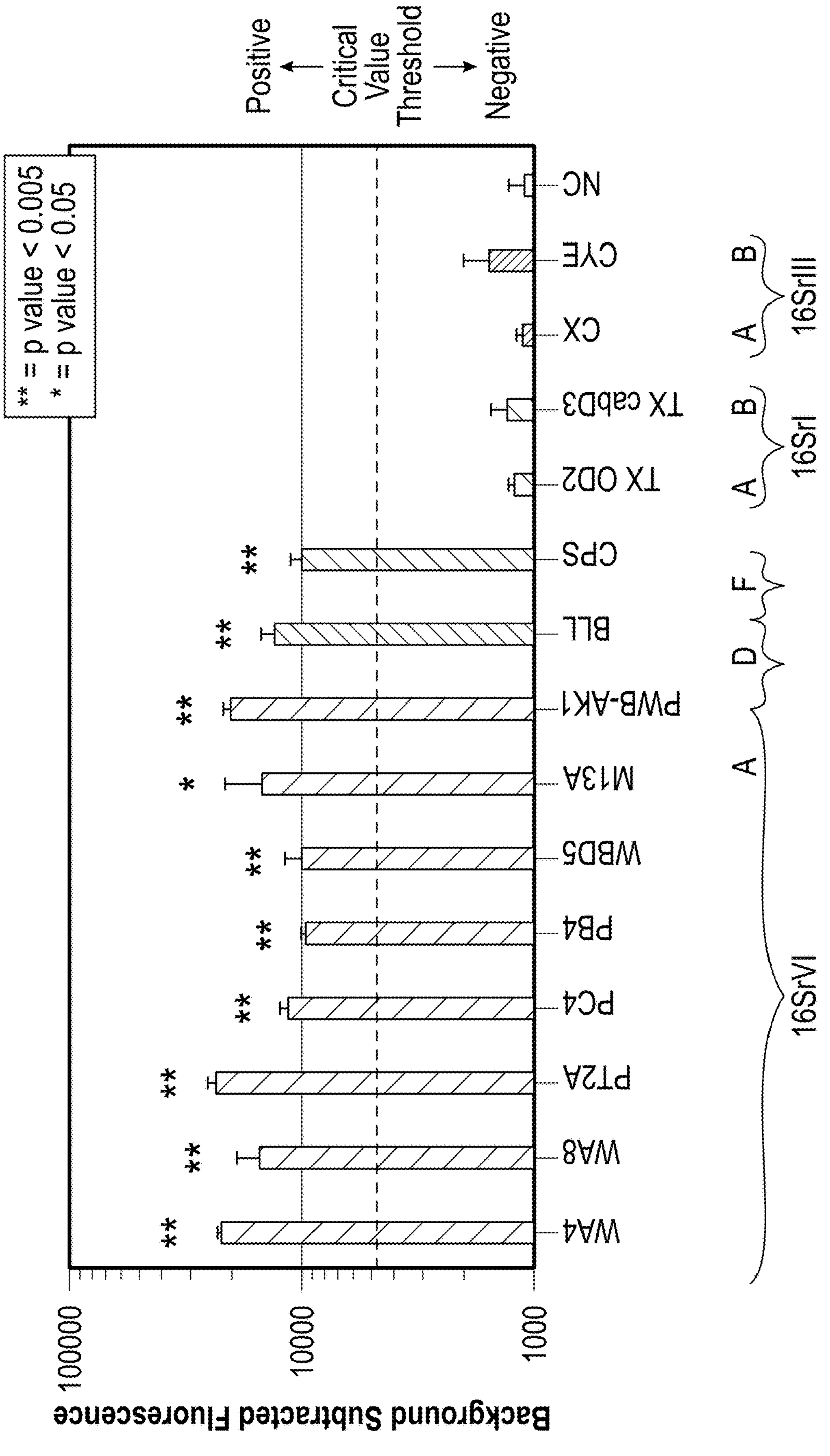
FIG. 11A-C shows detection of phytoplasma-infected samples using DETECTR assay.
Figure 11B:
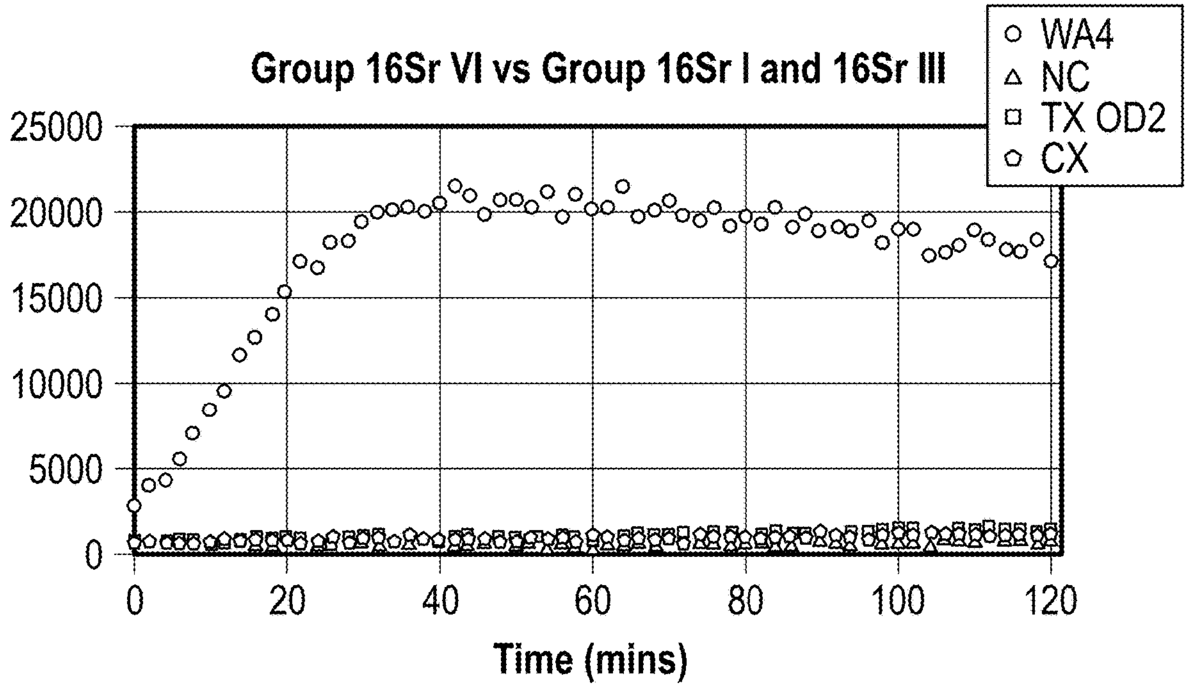
Figure 11C:
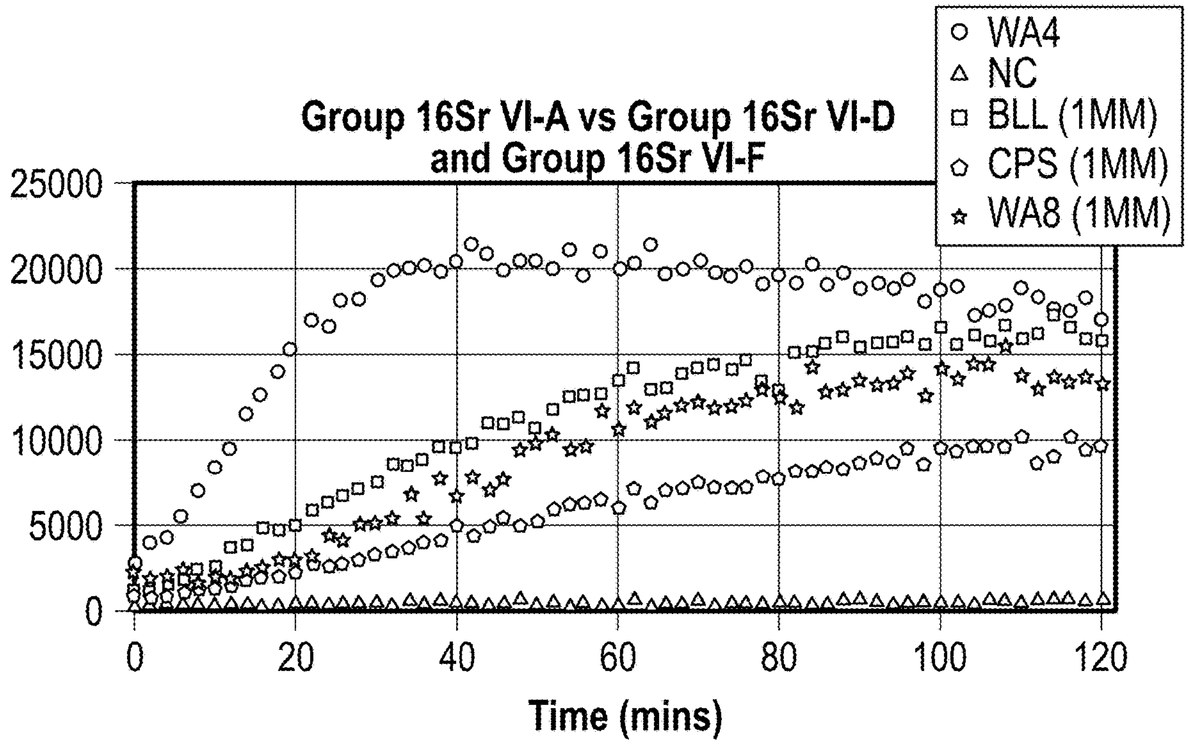

To determine the specificity of the PPT 16SrVI DETECTR assay, PPT WA4 strain-infected potato DNA sample vs. disease-free potato DNA (negative control) was evaluated. Following the RPA and Cas12a reactions, the infected potato DNA resulted in a strong fluorescence signal within the first 30-minutes of the reaction (FIG. 10), demonstrating the presence of a 16SrVI isolate. By contrast, the genomic DNA from disease-free potato (negative control) yielded minimal fluorescence signal, indicating no cross-reactivity (or off-targeting) of the crRNA with potato genomic DNA. Next, DNA samples from plants infected with 'Ca. *Phytoplasma trifolii*' and related strains of the PPT disease complex as well as DNAs of other 'Ca. *Phytoplasma*' species were tested, and the fluorescent intensity of the DETECTR results against those of PPT-WA4 positive and negative controls were compared. As expected, all of the samples from 'Ca. *Phytoplasma trifolii*'-related strains of group 16SrVI (including subgroups 16SrVI-A, 16SrVI-D, and 16SrVI-F) yielded a positive detection, while the phytoplasmas from 'Ca. *Phytoplasma asteris*' (group 16SrI) and 'Ca. *Phytoplasma pruni*' (group 16SrIII) exhibited minimal fluorescent signals below the threshold value (FIG. 11A, FIG. 11B). In comparison with the on-target samples such as WA4, PT2A and PWB-AK1, some group 16SrVI strains including WA8, PC4, PB4, WBD5, BLL, and CPS produced less robust signals (FIG. 11A, FIG. 11C). These strains contain a single nucleotide polymorphism in the spacer at position 10, proximal to the PAM. FIG. 11C shows the rates of the fluorescent reporter accumulation over time among on target sample PPT WA4 vs single mismatch-containing samples PPT WA8 (16SrVI-A), BLL (16SrVI-D), and CPS (16SrVI-F). The results indicated that Cas12a could cleave DNA targets with a single mismatch in the spacer. However, the turnover of the fluorescent reporter is lower, resulting in reduced signal intensity. In DNA targets that contain more than a single mismatch, Cas12a activity was abolished entirely, resulting in no signal.

DETECTR-Based Lateral Flow Assay for PPT Diagnostics.

Figure 12:
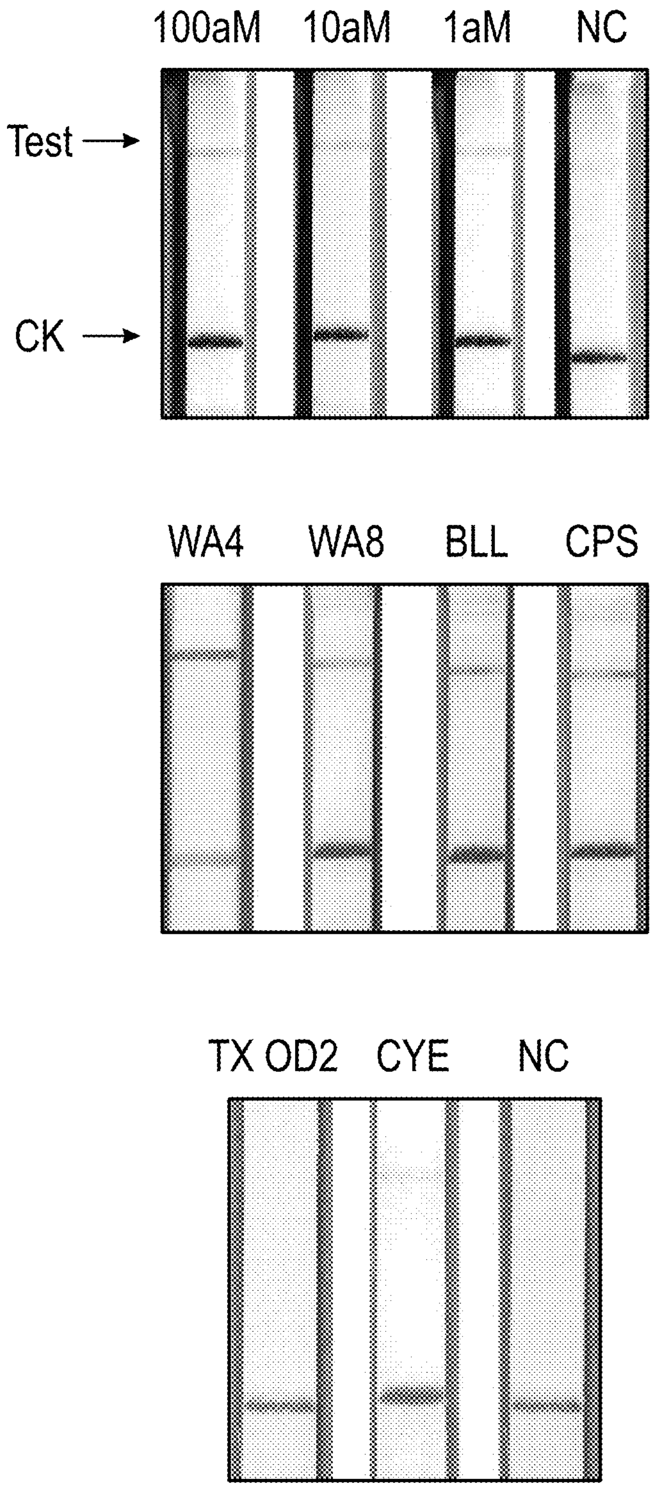
FIG. 12 shows image of lateral flow strips from PPT 16S-23S rDNA ITS DETECTR assay. pPPT-WA4 plasmid dilutions (100 aM, 10 aM, and 1 aM) and various infected plant DNA samples were used in the lateral flow assay. Immunostrips were dipped into the reaction samples for 10 minutes before the picture was taken. CK, streptavidin band (control); Test, antibody capture band (test sample).

In addition to the fluorescence detection via a microplate reader, lateral flow strips (HybriDetect, Milenia Biotec) were employed for a semi-quantitative detection that may facilitate in-field diagnostics of 'Ca. *Phytoplasma trifolii*'-associated PPT disease complex using the DETECTR assay. Six genomic DNA samples (WA4, WA8, BLL, CPS, TX OD2 and CYE), along with positive controls (1-100 aM of the pPPT-WA4 plasmid) and a negative control (NC, DNA from disease-free potato), were analyzed with lateral flow strips. Positive detection of the 16SrVI ITS amplicon was observed with WA4, WA8, BLL and CPS in the lateral flow assay (FIG. 12), which is consistent with the result from the fluorescence microplate reader. Using the pPPT-WA4 dilution standard, attomolar sensitivity was also achieved using the lateral flow assay to detect the 16SrVI DNA target (FIG. 12).

Methods

DNA preparation and target sequence selection: The phytoplasma and plant DNA samples used in this example were prepared according to a modified procedure using the DNeasy Plant Mini Kit (Qiagen). PPT phytoplasma-infected plant sample WA4 was collected from a potato production field in the Washington State in 2003. PPT WA4 16S rDNA fragment was amplified by PCR using primer pair P1A/16S-SR, and cloned into vector pCR2.1-TOPO (Invitrogen) to produce a target DNA plasmid (pPPT-WA4). Based on the alignment of the 16S-23S rDNA ITS sequences from reference strains of known 'Ca. *Phytoplasma*' species, a 156 bp region unique to 'Ca. *Phytoplasma trifolii*' was selected as the detection target. Specific RPA primers and crRNA spacer were designed, produced and tested for the RPA and DETECTR assays (TABLE 2).

TABLE 2

| | |
|---|---|
| RPA F2* | TGATAAGCGTGAGGTCGGTGGTTCAAGTCC (SEQ ID NO: 9) |
| RPA R3* | TCTTAGTGCCAAGGCATCCACTATATGCCC (SEQ ID NO: 10) |
| RPA F1 | CGTGAGGTCGGTGGTTCAAGTCCATTTAGG (SEQ ID NO: 11) |
| RPA F3 | CACGCCTGATAAGCGTGAGGTCGGTGGTTC (SEQ ID NO: 12) |
| RPA R1 | AGGCATCCACTATATGCCCTTACTTCCTTC (SEQ ID NO: 13) |
| RPA R2 | CCAAGGCATCCACTATATGCCCTTACTTCC (SEQ ID NO: 14) |
| T7 IVT | TAATACGACTCACTATAG (SEQ ID NO: 5) |
| 16SrVI IVT | **GGTCCTGCTTAAGAAGTTCTTT**ATCTACACTTAGTAGAAATTAC TATAGTGAGTCGTATTA (SEQ ID NO: 15) |

TABLE 2-continued

| | |
|---|---|
| 16SrVI spacer | **AAAGAACTTCTTAAGCAGGAC** (SEQ ID NO: 16) |
| 16SrVI crRNA | TAATTTCTACTAAGTGTAGAT**AAAGAACTTCTTAAGCAGGAC** (SEQ ID NO: 17) |
| Reporter oligo (PR) | 56-FAMN/TTA TT/3IABKFQ/ |
| Reporter oligo (LF) | 56-FAMN/TTA TT/3Bio/ |

Boldface indicates crRNA spacer sequence; Asterisk indicates the primer pair selected for the 16SrVI RPA reaction after evaluation of various primer pairs.

CRISPR RNA preparation and in vitro cleavage assay: In vitro transcription (IVT) of the crRNA specific to 'Ca. *Phytoplasma trifolii*' was carried out using the HiScribe T7 High Yield RNA Synthesis Kit (New England Biolabs). After annealing the T7 promoter (T7-F IVT: TAA TAC GAC TCA CTA TAG (SEQ ID NO: 5)) with the crRNA oligonucleotide (16SrVI IVT: GGT CCT GCT TAA GAA GTT CTT TAT CTA CAC TTA GTA GAA ATT ACT ATA GTG AGT CGT ATT A (SEQ ID NO: 15)), IVT was performed based on manufacturer's instruction. The resulting crRNA was purified with the RNA Clean & Concentrator kit (ZYMO Research) according to the manufacturer's instruction. To assess the activity and specificity of crRNA/Cas12a, in vitro cleavage assay was performed at 37° C. for 1 hr in 20 μl 1×NEB 2.1 reaction buffer using 50 nM target plasmid, 50 nM En Gen Lba Cas12a (NEB) and 50 nM IVT crRNA. Thirty μl reaction product was treated with 1 μl proteinase K at room temperature for 10 minutes before loading into an agarose gel for analysis.

DETECTR assay for 16SrVI target DNA: The DETECTR assay combines isothermal amplification in the form of RPA along with Cas12a collateral cleavage of fluorescent reporter oligos in a two-step reaction. The first step is a 20 μL RPA reaction comprised of target DNA plasmid (pPPT-WA4) or infected plant genomic DNA (50 ng), 0.48 pM primer pair (RPA F2: TGA TAA GCG TGA GGT CGG TGG TTC AAG TCC (SEQ ID NO: 9); and RPA-R3: TCT TAG TGC CAA GGC ATC CAC TAT ATG CCC (SEQ ID NO: 10)), proprietary enzyme and reaction buffer blends (TwistDx Liquid Basic). The reaction was initiated by adding 14 nM of magnesium acetate and proceeded for 15 minutes at 37° C. In the second step, the RPA reaction product (2 μL) was mixed with the Cas12a components containing 50 nM of EnGen Cas12a (New England Biolabs), 62.5 nM of crRNA, and 50 nM of custom fluorescent oligonucleotide reporter (5'-56-FAMN/TTA TT/3IABkFQ/-3') in a 20 μL reaction using NEB 2.1 buffer. The fluorescent reporter oligo was synthesized by IDT and contains FAM (Fluorescein) and FQ (fluorescence quencher). The Cas12a assay was incubated at 37° C. using a BioTek Synergy H1 microplate reader in a 384-well fluorescent microplate, recording the fluorescence intensity (excitation 495 nm, emission 535 nm) every 2 minutes for two hours. The maximum mean fluorescence (n=3 replicated) over the course of the reaction was compared to the negative control (e.g., disease-free potato DNA) to determine the presence of 'Ca. *Phytoplasma trifolii*'-specific 16SrVI target DNA. A positive cutoff value ($p \leq 0.05$) for identifying group 16SrVI samples was determined by performing a one-way ANOVA and Dunnett's post-test.

DETECTR-based lateral flow assay: For lateral flow assay, the fluorescent reporter oligo (5'-56-FAMN/TTA TT/3Bio/-3') containing FAM and biotin modifications was synthesized by IDT to provide compatibility with the HybriDetect (Milenia Biotec) lateral flow immunostrips. The DETECTR assay was performed as described above using the RPA reaction products and Cas12a detection components at 37° C. for two hours. After completion, 5 μL of the DETECTR product was aliquoted to a 1.5 mL Eppendorf tube. The HybriDetect hybridization buffer (100 μL) was added to the DETECTR product and incubate at room temperature for 5 minutes. For visual detection, a single lateral flow immunostrip was dipped into the reaction mix for 5-10 minutes.

Discussion

This example describes the development and validation of Cas12a-based diagnostics for highly sensitive and specific detection of 'Ca. *Phytoplasma trifolii*'-related strains associated with the PPT disease complex in North America. To adapt the DETECTR method for reliable detection of the target phytoplasmas, specific crRNA spacer and RPA primers were designed and evaluated based on an alignment of the available 16S rDNA and 16S-23S ITS sequences from strains of known 'Ca. *Phytoplasma*' species across the diverse 16Sr groups, with the PPT strain WA4 serving as a reference sequence for positive 'Ca. *Phytoplasma trifolii*' detection. This strain belongs to subgroup A of the clover proliferation phytoplasma group (16SrVI) known to cause PPT and PWB diseases. Based on the sequence alignment, there is only one location for the crRNA to be positioned to provide group 16SrVI specificity with nearby sites for RPA primer design. Due to sequence heterogenicity among the known 16SrVI-A PPT strains, a SNP (G-A) within the target DNA sequence created a single mismatch against our crRNA spacer (C-T, position 10, PAM proximal). The DETECTR assay enabled a strong detection of on-target samples with 100% hybridization between the crRNA and target DNA sequence. Samples containing a single mismatch still resulted in positive detection but exhibited a reduced or delayed rate of Cas12a activation and trans-cleavage of the fluorescent reporter oligo (FIG. 11A, FIG. 11C).

Overall, the results with Lba Cas12a are consistent with reports of other Cas12a nucleases used in diagnostic applications in terms of high specificity and attomolar sensitivity. However, there are some limitations in using Lba Cas12a for this specific application, including the reduced activity in samples containing single mismatches due to sequence variation of the 16SrVI-A isolates known to cause PPT and PWB in potato. Previously, single nucleotide specificity in Cas12a detection has been achieved by using crRNA containing an artificial mismatch within the spacer sequence. Such an artificial mismatch generates a second mismatch between the hybridized spacer and the single mismatch target DNA sequence, further attenuating the activity of Cas12a at off-target sites. Therefore, a dual crRNA approach, using one crRNA for each genotype that contains artificial mismatches to reduce general off-target activity, may provide robust activity across samples containing polymorphisms within the spacer region. Fortunately, for PPT disease complex diagnosis, such a dual crRNA approach is not necessary as the single crRNA-based protocol devised in this example was able to detect all available 16SrVI PPT variants successfully.

Other Cas12a homologs and orthologs such as Cas12b have also been explored for nucleic acid-based detection strategies. Some of these nucleases exhibit different rates of activation and trans-cleavage of the fluorescent reporter oligo. Specifically, AaCas12b from *Alicyclobacillus acidiphilus* exhibited faster activation and trans-cleavage rates compared to PrCas12a and LbCas12a (from *Prevotella* and *Lachnospiraceae bacterium*, respectively) across two different target sequences. Using AaCas12b for detection applications may enable a faster diagnosis while retaining the same high levels of specificity and sensitivity. In addition, directed evolution or targeted mutagenesis of Cas12 nucleases can help improve crRNA and Cas12 interactions for on and off target activity, as well as increased PAM variation to enable a broader range of targetable sequence, as previously done with Cas9.

Collectively, the results show that CRISPR-based detection strategies have the capability to achieve rapid diagnosis for PPT and PWB diseases by providing specific and highly sensitive detection of nucleic acids unique to 'Ca. *Phytoplasma trifolii*' and related strains in group 16SrVI. The DETECTR assay could detect the 16SrVI rDNA target down to the attomolar level in both the microplate reader and the lateral flow assays, which is about 100 to 1000 times more sensitive than the standard qPCR as reported previously. Due to the supersensitivity of DETECTR assay, extra caution is required during the DNA preparation and assay operation to prevent samples from any potential contamination. For phytoplasma detection, more complete genome sequence information is needed to allow the design of better RPA primers and crRNAs for specific detection of particular phylogroups or species of phytoplasmas. The DETECTR assay could specifically detect 16SrVI phytoplasmas and distinguish them from 16SrI and 16SrIII groups, but other phylogroups such as 16SrII and 16SrXVIII are yet to be tested. Because of its compatibility with lateral flow immunostrip and microplate reader, the Cas12a-based DETECTR assay is expected to facilitate both high-throughput and field-deployable diagnostics for early detection of phytoplasmal plant pathogens.

REFERENCES

Chen, J. S., Ma, E., Harrington, L. B., Da Costa, M., Tian, X., Palefsky, J. M., and Doudna, J. A. 2018. CRISPR-Cas12a target binding unleashes indiscriminate single-stranded DNase activity. Science 360:436-439.

Crosslin, J. M., Rondon, S. I., and Hamm, P. B. 2012. Population dynamics of the beet leafhopper in northeastern Oregon and incidence of the beet leafhopper-transmitted virescence agent phytoplasma. Am J Pot Res 89:82-88.

Crosslin, J. M., Vandemark, G. J., and Munyaneza, J. E. 2006. Development of a real-time, quantitative PCR for detection of the columbia basin potato purple top phytoplasma in plants and beet leafhoppers. Plant Dis. 90:663-667.

Gootenberg, J. S., Abudayyeh, O. O., Kellner, M. J., Joung, J., Collins, J. J., and Zhang, F. 2018. Multiplexed and portable nucleic acid detection platform with Cas13, Cas12a and Csm6. Science 360:439-444.

Green, M. J., Thompson, D. A., and MacKenzie, D. J. 1999. Easy and efficient DNA extraction from woody plants for the detection of phytoplasmas by polymerase chain reaction. Plant Disease 83:482-485.

Hiruki, C. and Wang, K. 2004. Clover proliferation phytoplasma: '*Candidatus Phytoplasma trifolii*'. Int J Syst Evol Microbiol. 54(Pt 4):1349-53.

IRPCM *Phytoplasma/Spiroplasma* Working Team—*Phytoplasma* Taxonomy Group. 2004. '*Candidatus Phytoplasma*', a taxon for the wall-less, non-helical prokaryotes that colonize plant phloem and insects. Int J Syst Evol Microbiol. 54(Pt 4):1243-55.

Kleinstiver, B. P., Sousa, A. A., Walton, R. T., Esther, Y., Hsu, J. Y., Clement, K., Welch, M. M., Horng, J. E., Malagon-Lopez, J., Scarfò, I., Maus, M. V., Pinello, L., Aryee, M. J., and Joung, J. K. 2019. Engineered CRISPR-Cas12a variants with increased activities and improved targeting ranges for gene, epigenetic and base editing. Nat Biotechnol. 37:276-282.

Lee, I., Davis, R. E., and Gundersen-Rindal, E. D. 2000. *Phytoplasma*: Phytopathogenic Mollicutes. Annu. Rev. Microbiol. 54:221-255.

Lee, I. M., Bottner, K. D., Munyaneza, J. E., Secor, G. A., and Gudmestad, N. C. 2004a. Clover proliferation group (16SrVI), subgroup A (16SrVI-A) phytoplasma is a probable causal agent of potato purple top disease in Washington and Oregon. Plant Disease 88:429.

Lee, I. M., Bottner, K. D., Secor, G., and Rivera-Varas, V. 2006. *"Candidatus Phytoplasma americanum"*, a phytoplasma associated with a potato purple top wilt disease complex. Int. J. Syst. Evol. Microbiol. 56:1593-1597.

Lee, I.-M., Bottner, K. D., Zhao, Y., Davis, R. E., and Harrison, N. 2010. Phylogenetic analysis and delineation of phytoplasmas based on the secY gene. Int. J. Syst. Evol. Microbiol. 60:2887-2897.

Lee, I.-M., Gundersen-Rindal, D. E., Davis, R. E., and Bartoszyk, I. M. 1998. Revised classification scheme of phytoplasmas based on RFLP analyses of 16SrRNA and ribosomal protein gene sequences. Int. J. Syst. Bacteriol. 48:1153-1169.

Lee, I.-M., Martini, M., Marcone, C., and Zhu, S. F. 2004b. Classification of phytoplasma strains in the elm yellows group (16SrV) and proposal of '*Candidatus Phytoplasma ulmi*' for the phytoplasma associated with elm yellows. Int. J. Syst. Evol. Microbiol. 54, 337-347.

Li, L., Li, S., Wu, N., Wu, J., Wang, G., Zhao, G., and Wang, J. 2019. HOLMESv2: A CRISPR-Cas12b-assisted platform for nucleic acid detection and DNA methylation quantitation. ACS Synth. Biol. 8:2228-2237.

McCoy, R. E., Caudwell, A., Chang, C. J., Chen, T.-A., Chiykowski, L. N., Cousin, M. T., Dale, J. L., de Leeuw, G. T. N., Golino, D. A. and other authors. 1989. Plant diseases associated with mycoplasmalike organisms. In The Mycoplasmas Vol 5, ed. RF Whitcomb, JG Tully, 545-560. Academic Press, New York.

Munyaneza, J. E., Crosslin, J. M., Upton, J. E., and Buchman, J. L. 2010. Incidence of the beet leafhopper-transmitted virescence agent phytoplasma in local populations of the beet leafhopper, *Circulifer tenellus*, in Washington State. J Insect Sci 10:18.

Munyaneza, J. E, Crosslin, J. M., Jensen, A. S., Hamm, P. B., Thomas, P. E., Pappu, H. R., and Schreiber, A. 2005. Update on the potato purple top disease in the Columbia Basin. In: Proceedings, 44th Annual Washington State Potato Conference, 1-3 Feb. 2005, Moses Lake, WA. pp. 57-70.

Munyaneza, J. E., Crosslin, J. M., and Lee, I.-M. 2007. *Phytoplasma* diseases and insect vectors in potatoes of the Pacific Northwest of the United States. Bull Insectol 60:181-182.

Murphy, A. F., Rondon, S. I., Marchosky, R., Buchman, J., and Munyaneza J. E. (2014) Evaluation of beet leafhopper transmitted virescence agent damage in the Columbia Basin. Am. J Potato Res 91:101-108.

Naderali, N., Nejat, N., Vadamalai, G., Davis, R. E., Wei, W., Harrison, N. A., Kong, L., Kadir, J., Tan, Y. H. and Zhao, Y. 2017. *'Candidatus Phytoplasma* wodyetiae', a new taxon associated with yellow decline disease of foxtail palm (*Wodyetia bifurcata*). Int. J. Syst. Evol. Microbiol. 67: 3765-3772.

Nishimasu, H., Shi, X., Ishiguro, S., Gao, L., Hirano, S., Okazaki, S., Noda, T., Abudayyeh, O. O., Gootenberg, J. S., Mori, H., Oura, S., Holmes, B., Tanaka, M., Seki, M., Hirano, H., Aburatani, H., Ishitani, R., Ikawa, M., Yachie, N., Zhang, F., and Nureki, O. 2018. Engineered CRISPR-Cas9 nuclease with expanded targeting space. Science 361:1259-1262.

Santos-Cervantes, M. E., Chivez-Medina, J. A., Acosta-Pardini, J., Flores-Zamora, G. L., Méndez-Lozano, J., and Leyva-López, N. E. 2010. Genetic diversity and geographical distribution of phytoplasmas associated with potato purple top disease in Mexico. Plant Dis. 94:388-395.

Slaymaker, I. M., Gao, L., Zetsche, B., Scott, D. A., Yan, W. X., and Zhang, F. 2016. Rationally engineered Cas9 nucleases with improved specificity. Science 351:84-88.

Teng, F., Guo, L., Cui, T., Wang, X. G., Xu, K., Gao, Q., et al. 2019. CDetection: CRISPR-Cas12b-based DNA detection with sub-attomolar sensitivity and single-base specificity. Genome Biol. 20:132.

Wei, W., Trivellone, V., Dietrich, C. H., Zhao, Y., Bottner-Parker, K. D., and Ivanauskas, A. 2021. Identification of phytoplasmas representing multiple new genetic lineages from phloem-feeding leafhoppers highlights the diversity of phytoplasmas and their potential vectors. Pathogens 10:352.

Wei, W., Wu, W., Davis, R. E., Lee, I. M., and Zhao, Y. 2016. Development of molecular markers and a diagnostic tool for investigation of coinfections by and interactions between potato purple top and potato witches'-broom phytoplasmas in tomato. Ann. Appl. Biol. 168:133-141.

Wheatley, M. S. and Yang, Y. 2021. Versatile applications of the CRISPR/Cas toolkit in plant pathology and disease management. Phytopathology 111:1080-1090.

Wheatley, M. S., Duan, Y. P., and Yang, Y. 2021. Highly sensitive and rapid detection of citrus Huanglongbing pathogen (*Candidatus Liberibacter asiaticus*) using Cas12a-based methods. Phytopathology 111:2375-2382.

Zetsche, B., Gootenberg, J. S., Abudayyeh, O. O., Slaymaker, I. M., Makarova, K. S., Essletzbichler, P., Volz, S. E., Joung, J., van der Oost, J., Regev, A., Koonin, E. V., Zhang, F. 2015. Cpf1 is a single RNA-guided endonuclease of a class 2 CRISPR-Cas system. Cell. 163:759-771.

Zhao, Y. and Wei, W. 2020. Datasheet report for '*Candidatus Phytoplasma trifolii*'(clover proliferation phytoplasma). in Invasive Species Compendium. Wallingford, UK: CAB International.

Zhao, Y., Wei, W., Davis, R. E., Lee, I.-M., and Bottner-Parker, K. D. 2021. The agent associated with blue dwarf disease in wheat represents a new phytoplasma taxon, '*Candidatus Phytoplasma tritici*'. Int J Syst Evol Microbiol 105.

What is claimed is:

1. A method for detecting *Candidatus Liberibacter asiaticus* in a sample, the method comprising:

amplifying a target DNA comprising SEQ ID NO: 19 in the sample, wherein the amplifying comprises isothermal amplification;

contacting the amplified sample with a type V CRISPR/Cas effector protein, a guide RNA comprising a region that hybridizes with the target DNA, and a single stranded DNA (ssDNA) reporter oligonucleotide; and detecting a signal produced by cleavage of the ssDNA reporter oligonucleotide, wherein the method provides attomolar sensitivity of detection.

2. The method of claim 1, wherein the guide RNA comprises SEQ ID NO: 7.

3. The method of claim 1, wherein the type V CRISPR/Cas effector protein is a Cas12a protein.

4. The method of claim 1, comprising contacting the sample with a precursor guide RNA array, wherein the type V CRISPR/Cas effector protein cleaves the precursor guide RNA array to produce the guide RNA and at least one additional guide RNA.

5. The method of claim 1, wherein the sample comprises a plant cell or plant cell lysate.

6. The method of claim 5, wherein the plant cell or plant cell lysate is a *Citrus* cell or cell lysate.

7. The method of claim 1, wherein the ssDNA reporter oligonucleotide comprises a fluorescence-emitting dye pair.

8. The method of claim 1, wherein the isothermal amplification is recombinase polymerase amplification (RPA).

9. The method of claim 1, amplified with the primer pair of SEQ ID NOs: 1 and 2.

* * * * *

SEQUENCE LISTING

```
Sequence total quantity: 21
SEQ ID NO: 1             moltype = DNA  length = 30
FEATURE                  Location/Qualifiers
source                   1..30
                         mol_type = other DNA
                         organism = synthetic construct
SEQUENCE: 1
catcatgcga gatgaatcac tgcatctcaa                                   30

SEQ ID NO: 2             moltype = DNA  length = 28
FEATURE                  Location/Qualifiers
source                   1..28
                         mol_type = other DNA
                         organism = synthetic construct
SEQUENCE: 2
accgatttgg tgacaacgac gattggcg                                     28

SEQ ID NO: 3             moltype = DNA  length = 30
FEATURE                  Location/Qualifiers
source                   1..30
                         mol_type = other DNA
                         organism = synthetic construct
SEQUENCE: 3
ccgatttggt gacaacgacg attggcgatg                                   30

SEQ ID NO: 4             moltype = DNA  length = 30
FEATURE                  Location/Qualifiers
source                   1..30
                         mol_type = other DNA
                         organism = synthetic construct
SEQUENCE: 4
acgacgattg gcgatgaact gcatatattg                                   30

SEQ ID NO: 5             moltype = DNA  length = 18
FEATURE                  Location/Qualifiers
```

```
source                  1..18
                        mol_type = other DNA
                        organism = synthetic construct
SEQUENCE: 5
taatacgact cactatag                                                18

SEQ ID NO: 6            moltype = DNA  length = 59
FEATURE                 Location/Qualifiers
source                  1..59
                        mol_type = other DNA
                        organism = synthetic construct
SEQUENCE: 6
tcgaaatcgc ctatgcacat atctacactt agtagaaatt actatagtga gtcgtatta   59

SEQ ID NO: 7            moltype = DNA  length = 20
FEATURE                 Location/Qualifiers
source                  1..20
                        mol_type = other DNA
                        organism = synthetic construct
SEQUENCE: 7
atgtgcatag gcgatttcga                                              20

SEQ ID NO: 8            moltype = DNA  length = 41
FEATURE                 Location/Qualifiers
source                  1..41
                        mol_type = other DNA
                        organism = synthetic construct
SEQUENCE: 8
taatttctac taagtgtaga tatgtgcata ggcgatttcg a                      41

SEQ ID NO: 9            moltype = DNA  length = 30
FEATURE                 Location/Qualifiers
source                  1..30
                        mol_type = other DNA
                        organism = synthetic construct
SEQUENCE: 9
tgataagcgt gaggtcggtg gttcaagtcc                                   30

SEQ ID NO: 10           moltype = DNA  length = 30
FEATURE                 Location/Qualifiers
source                  1..30
                        mol_type = other DNA
                        organism = synthetic construct
SEQUENCE: 10
tcttagtgcc aaggcatcca ctatatgccc                                   30

SEQ ID NO: 11           moltype = DNA  length = 30
FEATURE                 Location/Qualifiers
source                  1..30
                        mol_type = other DNA
                        organism = synthetic construct
SEQUENCE: 11
cgtgaggtcg gtggttcaag tccatttagg                                   30

SEQ ID NO: 12           moltype = DNA  length = 30
FEATURE                 Location/Qualifiers
source                  1..30
                        mol_type = other DNA
                        organism = synthetic construct
SEQUENCE: 12
cacgcctgat aagcgtgagg tcggtggttc                                   30

SEQ ID NO: 13           moltype = DNA  length = 30
FEATURE                 Location/Qualifiers
source                  1..30
                        mol_type = other DNA
                        organism = synthetic construct
SEQUENCE: 13
aggcatccac tatatgccct tacttccttc                                   30

SEQ ID NO: 14           moltype = DNA  length = 30
FEATURE                 Location/Qualifiers
source                  1..30
                        mol_type = other DNA
                        organism = synthetic construct
SEQUENCE: 14
ccaaggcatc cactatatgc ccttacttcc                                   30

SEQ ID NO: 15           moltype = DNA  length = 61
```

-continued

FEATURE Location/Qualifiers
source 1..61
mol_type = other DNA
organism = synthetic construct
SEQUENCE: 15
ggtcctgctt aagaagttct ttatctacac ttagtagaaa ttactatagt gagtcgtatt 60
a 61

SEQ ID NO: 16 moltype = DNA length = 21
FEATURE Location/Qualifiers
source 1..21
mol_type = other DNA
organism = synthetic construct
SEQUENCE: 16
aaagaacttc ttaagcagga c 21

SEQ ID NO: 17 moltype = DNA length = 42
FEATURE Location/Qualifiers
source 1..42
mol_type = other DNA
organism = synthetic construct
SEQUENCE: 17
taatttctac taagtgtaga taaagaactt cttaagcagg ac 42

SEQ ID NO: 18 moltype = DNA length = 21
FEATURE Location/Qualifiers
source 1..21
mol_type = other DNA
organism = synthetic construct
SEQUENCE: 18
taatttctac taagtgtaga t 21

SEQ ID NO: 19 moltype = DNA length = 247
FEATURE Location/Qualifiers
source 1..247
mol_type = other DNA
organism = synthetic construct
SEQUENCE: 19
catcatgcga gatgaatcac tgcatctcaa ttttggtatt gatgtcatca accaaattaa 60
aatcgaaaac ccccatcttt ggacaaaaga gttccaacaa aaaagtcgca ccatgctcca 120
tgaagctacc ctcctcgaaa tcgcctatgc acatgaaaca atgccaaaag ggttcgtggg 180
gttaaatgct ccctcatgtg aacaatatat gcagttcatc gccaatcgtc gttgtcacca 240
aatcggt 247

SEQ ID NO: 20 moltype = DNA length = 152
FEATURE Location/Qualifiers
source 1..152
mol_type = other DNA
organism = synthetic construct
SEQUENCE: 20
tgataagcgt gaggtcggtg gttcaagtcc atttaggccc accaaaaaaa ggtcctgctt 60
aagaagttct ttgaaaagta ggtaaacatg ctttaaaatt ttcataaagt tgaaggaagt 120
aagggcatat agtggatgcc ttggcactaa ga 152

SEQ ID NO: 21 moltype = AA length = 1228
FEATURE Location/Qualifiers
source 1..1228
mol_type = protein
note = Lachnospiraceae bacterium ND2006
organism = unidentified
SEQUENCE: 21
MSKLEKFTNC YSLSKTLRFK AIPVGKTQEN IDNKRLLVED EKRAEDYKGV KKLLDRYYLS 60
FINDVLHSIK LKNLNNYISL FRKKTRTEKE NKELENLEIN LRKEIAKAFK GNEGYKSLFK 120
KDIIETILPE FLDDKDEIAL VNSFNGFTTA FTGFFDNREN MFSEEAKSTS IAFRCINENL 180
TRYISNMDIF EKVDAIFDKH EVQEIKEKIL NSDYDVEDFF EGEFFNFVLT QEGIDVYNAI 240
IGGFVTESGE KIKGLNEYIN LYNQKTKQKL PKFKPLYKQV LSDRESLSFY GEGYTSDEEV 300
LEVFRNTLNK NSEIFSSIKK LEKLFKNFDE YSSAGIFVKN GPAISTISKD IFGEWNVIRD 360
KWNAEYDDIH LKKKAVVTEK YEDDRRKSFK KIGSFSLEQL QEYADADLSV VEKLKEIIIQ 420
KVDEIYKVYG SSEKLFDADF VLEKSLKKND AVVAIMKDLL DSVKSFENYI KAFFGEGKET 480
NRDESFYGDF VLAYDILLKV DHIYDAIRNY VTQKPYSKDK FKLYFQNPQF MGGWDKDKET 540
DYRATILRYG SKYYLAIMDK KYAKCLQKID KDDVNGNYEK INYKLLPGPN KMLPKVFFSK 600
KWMAYYNPSE DIQKIYKNGT FKKGDMFNLN DCHKLIDFFK DSISRYPKWS NAYDFNFSET 660
EKYKDIAGFY REVEEQGYKV SFESASKKEV DKLVEEGKLY MFQIYNKDFS DKSHGTPNLH 720
TMYFKLLFDE NNHGQIRLSG GAELFMRRAS LKKEELVVHP ANSPIANKNP DNPKKTTTLS 780
YDVYKDKRFS EDQYELHIPI AINKCPKNIF KINTEVRVLL KHDDNPYVIG IDRGERNLLY 840
IVVVDGKGNI VEQYSLNEII NNFNGIRIKT DYHSLLDKKE KERFEARQNW TSIENIKELK 900
AGYISQVVHK ICELVEKYDA VIALEDLNSG FKNSRVKVEK QVYQKFEKML IDKLNYMVDK 960
KSNPCATGGA LKGYQITNKF ESFKSMSTQN GFIFYIPAWL TSKIDPSTGF VNLLKTKYTS 1020
IADSKKFISS FDRIMYVPEE DLFEFALDYK NFSRTDADYI KKWKLYSYGN RIRIFRNPKK 1080

-continued

| | | | | | | |
|---|---|---|---|---|---|---|
| NNVFDWEEVC | LTSAYKELFN | KYGINYQQGD | IRALLCEQSD | KAFYSSFMAL | MSLMLQMRNS | 1140 |
| ITGRTDVDFL | ISPVKNSDGI | FYDSRNYEAQ | ENAILPKNAD | ANGAYNIARK | VLWAIGQFKK | 1200 |
| AEDEKLDKVK | IAISNKEWLE | YAQTSVKH | | | | 1228 |